United States Patent
Benning et al.

(10) Patent No.: US 10,392,629 B2
(45) Date of Patent: Aug. 27, 2019

(54) INCREASED CALORIC AND NUTRITIONAL CONTENT OF PLANT BIOMASS

(71) Applicant: Board of Trustees of Michigan State University, East Lansing, MI (US)

(72) Inventors: Christoph Benning, East Lansing, MI (US); Sanjaya, East Lansing, MI (US); Rachel Miller, Murrells Inlet, SC (US)

(73) Assignee: Board of Trustees of Michigan State University, East Lansing, MI (US)

( * ) Notice: Subject to any disclaimer, the term of this patent is extended or adjusted under 35 U.S.C. 154(b) by 631 days.

(21) Appl. No.: 14/598,953

(22) Filed: Jan. 16, 2015

(65) Prior Publication Data

US 2015/0203861 A1    Jul. 23, 2015

Related U.S. Application Data

(60) Provisional application No. 61/928,559, filed on Jan. 17, 2014.

(51) Int. Cl.
| | | |
|---|---|---|
| C12N 15/82 | (2006.01) | |
| C12N 9/10 | (2006.01) | |
| C10L 1/19 | (2006.01) | |
| C10G 32/00 | (2006.01) | |

(52) U.S. Cl.
CPC ......... *C12N 15/8247* (2013.01); *C10G 32/00* (2013.01); *C10L 1/19* (2013.01); *C12N 9/1029* (2013.01); *C12N 15/8261* (2013.01); *C10L 2200/0476* (2013.01); *C10L 2290/08* (2013.01); *C10L 2290/547* (2013.01); *C12Y 203/0102* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,695,411 A | 9/1987 | Stern et al. | |
| 4,940,838 A | 7/1990 | Schilperoort et al. | |
| 4,945,050 A | 7/1990 | Sanford et al. | |
| 4,965,188 A | 10/1990 | Mullis et al. | |
| 4,981,785 A | 1/1991 | Nayak | |
| 5,057,422 A | 10/1991 | Bol et al. | |
| 5,173,410 A | 12/1992 | Ahlquist | |
| 5,187,267 A | 2/1993 | Comai et al. | |
| 5,352,605 A | 10/1994 | Fraley et al. | |
| 5,358,691 A | 10/1994 | Clark et al. | |
| 5,451,513 A | 9/1995 | Maliga et al. | |
| 5,500,360 A | 3/1996 | Ahlquist et al. | |
| 5,501,967 A | 3/1996 | Offringa et al. | |
| 5,538,848 A | 7/1996 | Livak et al. | |
| 5,545,817 A | 8/1996 | McBride et al. | |
| 5,545,818 A | 8/1996 | McBride et al. | |
| 5,584,807 A | 12/1996 | McCabe | |
| 5,596,131 A | 1/1997 | Horn et al. | |
| 5,599,677 A | 2/1997 | Dowell et al. | |
| 5,639,606 A | 6/1997 | Willey | |
| 5,643,765 A | 7/1997 | Willey | |
| 5,672,480 A | 9/1997 | Dowell et al. | |
| 5,824,877 A | 10/1998 | Hinchee et al. | |
| 5,846,717 A | 12/1998 | Brow et al. | |
| 5,846,795 A | 12/1998 | Ahlquist et al. | |
| 5,866,330 A | 2/1999 | Kinzler et al. | |
| 5,866,785 A | 2/1999 | Donson et al. | |
| 5,876,978 A | 3/1999 | Willey et al. | |
| 5,885,530 A | 3/1999 | Babson et al. | |
| 5,965,794 A | 10/1999 | Turpen | |
| 5,977,438 A | 11/1999 | Turpen et al. | |
| 5,981,839 A | 11/1999 | Knauf et al. | |
| 5,981,840 A | 11/1999 | Zhao et al. | |
| 5,985,557 A | 11/1999 | Prudent et al. | |
| 5,994,069 A | 11/1999 | Hall et al. | |
| 6,001,567 A | 12/1999 | Brow et al. | |
| 6,051,757 A | 4/2000 | Barton et al. | |
| 6,090,543 A | 7/2000 | Prudent et al. | |
| 6,159,750 A | 12/2000 | Edmonds | |
| 7,122,367 B2 | 10/2006 | Milcamps et al. | |
| 7,429,473 B2 | 9/2008 | Milcamps et al. | |
| 7,511,189 B2 | 3/2009 | Zou et al. | |
| 8,362,318 B2 | 1/2013 | Benning | |

(Continued)

FOREIGN PATENT DOCUMENTS

DE    4317414 C1    4/1994
EP    0292435 A1    11/1988

(Continued)

OTHER PUBLICATIONS

Bach et al (Role of very-long-chain fatty acids in plant development, when chain length does matter. C. R. Biologies. 333: 361-370, 2010).*

Lardizabal et al (Expression of Umbelopsis ramanniana DGAT2A in Seed Increases Oil in Soybean. Plant Physiology, vol. 148, pp. 89-96, Sep. 2008).*

Ohlrogge et al (Lipid Biosynthesis. The Plant Cell, vol. 7, 957-970, Jul. 1995).*

Banilas et al (The olive DGAT2 gene is developmentally regulated and shares overlapping but distinct expression patterns with DGAT1. Journal of Experimental Botany, vol. 62, No. 2, pp. 521-532, 2011).*

Sanjaya et al (Altered Lipid Composition and Enhanced Nutritional Value of *Arabidopsis* Leaves following Introduction of an Algal Diacylglycerol Acyltransferase 2. The Plant Cell, vol. 25: 677-693, Feb. 2013).*

(Continued)

*Primary Examiner* — Medina A Ibrahim
*Assistant Examiner* — Wayne Zhong
(74) *Attorney, Agent, or Firm* — Schwegman Lundberg & Woessner, P.A.

(57) ABSTRACT

As described herein, plants expressing algal Diacylglycerol Acyltransferase Type Two (DGTT) from heterologous nucleic acids can alter acyl carbon partitioning in plant vegetative tissues and increase acyl-CoA-dependent triacylglycerol synthesis, thereby increasing the lipid content of the plants' tissues.

16 Claims, 38 Drawing Sheets

Specification includes a Sequence Listing.

(56) References Cited

U.S. PATENT DOCUMENTS

| | | | |
|---|---|---|---|
| 9,062,331 | B2 | 6/2015 | Benning et al. |
| 9,328,335 | B2 | 5/2016 | Durrett et al. |
| 2007/0028329 | A1 | 2/2007 | Milcamps et al. |
| 2007/0204370 | A1 | 8/2007 | Mietkiewska et al. |
| 2007/0231819 | A1 | 10/2007 | Lawrence et al. |
| 2010/0317073 | A1 | 12/2010 | Sayre et al. |
| 2011/0061130 | A1* | 3/2011 | Zou ...................... C12N 9/1029 800/281 |
| 2013/0116462 | A1 | 5/2013 | Durrett et al. |
| 2013/0212736 | A1 | 8/2013 | Benning et al. |

FOREIGN PATENT DOCUMENTS

| | | | |
|---|---|---|---|
| EP | 0332581 | A2 | 9/1989 |
| WO | WO-93/007278 | A1 | 4/1993 |
| WO | WO-93/18176 | A1 | 9/1993 |
| WO | WO-94/013822 | A2 | 6/1994 |
| WO | WO-95/14098 | A1 | 5/1995 |
| WO | WO-95/16783 | A1 | 6/1995 |
| WO | WO-2011/082253 | A2 | 7/2011 |
| WO | WO-2011156520 | A2 * | 12/2011 ............... C08L 91/00 |

OTHER PUBLICATIONS

"U.S. Appl. No. 12/639,304, Interview Summary dated Sep. 18, 2012", 1 pg.
"U.S. Appl. No. 12/639,304, Non-Final Office Action dated Mar. 15, 2012", 15 pgs.
"U.S. Appl. No. 12/639,304, Notice of Allowance dated Sep. 18, 2012", 8 pgs.
"U.S. Appl. No. 12/639,304, Response filed Jan. 31, 2012 to Restriction Requirement dated Jan. 3, 2012", 4 pgs.
"U.S. Appl. No. 12/639,304, Response filed Jun. 5, 2012 to Non-Final Office Action dated Mar. 15, 2012", 13 pgs.
"U.S. Appl. No. 12/639,304, Restriction Requirement dated Jan. 3, 2012", 6 pgs.
"U.S. Appl. No. 13/519,660, Non Final Office Action dated Jul. 2, 2015", 20 pgs.
"U.S. Appl. No. 13/519,660, Notice of Allowance dated Dec. 24, 2015", 10 pgs.
"U.S. Appl. No. 13/519,660, Preliminary Amendment filed Jun. 28, 2012", 13 pgs.
"U.S. Appl. No. 13/519,660, PTO Response to Rule 312 Communication dated Apr. 5, 2016", 2 pgs.
"U.S. Appl. No. 13/519,660, Response filed May 26, 2015 to Restricticon Requirement dated Feb. 27, 2015", 20 pgs.
"U.S. Appl. No. 13/519,660, Response filed Oct. 1, 2015 to Non Final Office Action dated Jul. 2, 2015", 24 pgs.
"U.S. Appl. No. 13/519,660, Restriction Requirement dated Feb. 27, 2015", 14 pgs.
"U.S. Appl. No. 13/519,660, Supplemental Preliminary Amendment filed Jun. 25, 2013", 15 pgs.
"U.S. Appl. No. 13/719,868, Non Final Office Action dated Sep. 25, 2014", 7 pgs.
"U.S. Appl. No. 13/719,868, Notice of Allowance dated Feb. 17, 2015", 5 pgs.
"U.S. Appl. No. 13/719,868, Preliminary Amendment filed Apr. 30, 2013", 7 pgs.
"U.S. Appl. No. 13/719,868, Preliminary Amendment filed Dec. 19, 2012", 3 pgs.
"U.S. Appl. No. 13/719,868, Response filed Dec. 16, 2014 to Non Final Office Action dated Sep. 25, 2014", 6 pgs.
"U.S. Appl. No. 13/719,868, Supplemental Preliminary Amendment filed May 1, 2013", 3 pgs.
"International Application Serial No. PCT/US2010/062407, International Preliminary Report on Patentability dated Jul. 4, 2012", 7 pgs.
"International Application Serial No. PCT/US2010/062407, International Search Report dated Aug. 2, 2011", 5 pgs.
"International Application Serial No. PCT/US2010/062407, Invitation to pay additional fees dated Jun. 6, 2011", 2 pgs.
"International Application Serial No. PCT/US2010/062407, Written Opinion dated Aug. 2, 2011", 6 pgs.
"UniProt Direct Submission. B9SSQ4_RICCO", [online]. © 2002-2012 UniProt Consortium [retrieved on Jun. 27, 2012]. Retrieved from the Internet: <URL: http://www.uniprot.org/uniproVB9SSQ4>, (Apr. 18, 2012), 3 pgs.
"UniProt Direct Submission. D6NSS8_EUOAL", [online]. © 2002-2012 UniProt Consortium [retrieved on Jun. 27, 2012]. Retrieved from the Internet: <URL: http://www.uniprot.org/uniproVD6NSS8>, (Nov. 16, 2011), 3 pgs.
Adams, M. D., et al., "Rapid cDNA sequencing (expressed sequence tags) from a directionally cloned human infant brain cDNA library", Nat. Genet., 4(4), (1993), 373-380.
Ballas, N., et al., "Efficient functioning of plant promoters and poly( A) sites in Xenopus oocytes", Nucleic Acids Res., 17(19), (1989), 7891-7903.
Baud, S., et al., "An integrated overview of seed development in Arabidopsis thaliana ecotype WS", Plant Physiol. Biochem., 40(2), (2002), 151-160.
Bauer, D., et al., "Identification of differentially expressed mRNA species by an Improved display technique (DDRT-PCR)", Nucleic Acids Res., 21(18), (1993), 4272-4280.
Beachy, R. N., et al., "Accumulation and assembly of soybean β-conglycinin in seeds of transformed petunia plants", EMBO J., 4(12), (1985), 3047-3053.
Bertioli, D. J., et al., "An analysis of differential display shows a strong bias towards high copy number mRNAs", Nucleic Acids Res. 23(21), (1995), 4520-4523.
Bevan, M., et al., "A chimaeric antibiotic resistance gene as a selectable marker for plant cell transformation", Nature, 304(5922), (1983), 184-187.
Bligh, E. G., et al., "A Rapid Method of Total Lipid Extraction and Purification", Canadian Journal of Biochemistry and Physiology., 37(8), (1959), 911-917.
Blochlinger, K., et al., "Hygromycin B Phosphotransferase as a Selectable Marker for DNA Transfer Experiments with Higher Eucaryotic Cells", Mol. Cell. Biol., 4(12), (1984), 2929-2931.
Bourouis, M., et al., "Vectors containing a prokaryotic dihydrofolate reductase gene transform Drosophila cells to methotrexate-resistance", The EMBO Journal, 2(7), (1983), 1099-1104.
Bouvier-Nave, P., et al., "Expression in Yeast and Tobacco of Plant cDNAs Encoding Acyl CoA Diacylglycerol Acyltransferase", Eur. J. Biochem. 267(1), (2000), 85-96.
Burgal, J., et al., "Metabolic engineering of hydroxy fatty acid production in plants: RcDGAT2 drives dramatic increases in ricinoleate levels in seed oil", Plant Biotechnology Journal, 6(8), (2008), 819-831.
Callis, J., et al., "Introns Increase Gene Expression in Cultured Maize Cells", Genes and Development, 1(10), (1987), 1183-1200.
Casas, A. M., et al., "Transgenic sorghum plants via microprojectile bombardment", Proc. Natl. Acad. Sci. USA, 90(23), (1993), 11212-11216.
Chamberlin, M., et al., "New RNA polymerase from Escherichia coli infected with Bacteriophage T7", Nature, 228(5268), (1970), 227-231.
Chao, W. S., et al., "Leucine Aminopeptidase RNAs, Proteins, and Activities Increase in Response to Water Deficit, Salinity, and the Wound Signals Systemin, Methyl Jasmonate, and Abscisic Acid.", Plant Physiol , 120(4), (1999), 979-992.
Chen, Q., "Biosynthesis of Phytosterol Esters: Identification of a Sterol O-Acyltransferase in Arabidopsis", Plant Physiol., 145, (2007), 974-984.
Christou, P., et al., "Production of Transgenic Rice (Oryza sativa L.) Plants from Agronomically Important Indica and Japonica Varieties via Electric Discharge Particle Acceleration of Exogenous DNA into Immature Zygotic Embryos", Nature Biotechnology, 9(10), (1991), 957-962.
Christou, P., et al., "Stable Transformation of Soybean Callus by DNA-Coated Gold Particles", Plant Physiol., 87(3), (1988), 671-674.

(56) References Cited

OTHER PUBLICATIONS

Crossway, A., et al., "Integration of foreign DNA following microinjection of tobacco mesophyll protoplasts", Mol. Gen. Genet., 202(2), (1986), 179-185.
Crossway, A., et al., "Micromanipulation Techniques in Plant Biotechnology.", BioTechniques, 4(4), (1986), 320-334.
Dahlqvist, A., et al., "Phospholipid diacylglycerol acyltransferase: An enzyme that catalyzes the acyl-CoA-independent formation of triacylglycerol in yeast and plants", Proc. Natl. Acad. Sci. USA, 97(12), (2000), 6487-6492.
Datta, S. K., et al., "Genetically Engineered Fertile Indica-Rice Recovered from Protoplasts", Nat. Biotechnol.8(8), (1990), 736-740.
Dehesh, K., et al., "Production of high levels of 8:0 and 10:0 fatty acids in transgenic canola by overexpression of Ch FatB2, a thioesterase cDNA from *Cuphea hookeriana*", The Plant Journal, 9(2), (1996), 167-172.
Dehesh, K., et al., "Two Novel Thioesterases are Key Determinants of the Bimodal Distribution of Acyl Chain Length of *Cuphea palustris* Seed Oil", Plant Physiology, 110(1), (1996), 203-210.
Derisi, Joseph, et al., "Use of a cDNA microarray to analyse gene expression patters in human cancer", Nature Genetics, vol. 14, (Dec. 1996), 457-460.
Durrett, T. P, et al., "A distinct DGAT with sn-3 acetyltransferase activity that synthesizes unusual, reduced-viscosity oils in *uonymus* and transgenic seeds.", Proc Natl Acad Sci U S A., 107(20), (May 18, 2010), 9464-9.
Durrett, T. P., et al., "Plant triacylglycerols as feedstocks for the production of biofuels", The Plant Journal, 54(4), (2008), 593-607.
Dyer, J. D., et al., "Development and potential of genetically engineered oilseeds", Seed Sci. Res., 15, (2005), 255-267.
Fraley, R. T., et al., "Liposome-mediated delivery of tobacco mosaic virus RNA into tobacco protoplasts: A sensitive assay for monitoring lipolipo-some-protoplast interactions", Proc. Nat!. Acad. Sci., USA, 79, (1982), 1859-1863.
Friedberg, "Automated protein function prediction—the genomic challenge", Brief. Bioinformatics 7, (2006), 225-242.
Fromm, M. E., et al., "Expression of genes transferred into monocot and dicot plant cells by electroporation", Proc. Nat. Acad. Sci. USA, 82(17), (1985), 5824-5828.
Fromm, M. E., et al., "Inheritance and Expression of Chimeric Genes in the Progeny of Transgenic Maize Plants", Nature Biotechnology, 8(9), (1990), 833-839.
Garbarino, J. E., et al., "Isolation of a ubiquitin-ribosomal protein gene (ubi3) from potato and expression of its promoter in transgenic plants.", Plant Mol. Biol., 24(1), (1994), 119-127.
Gordon-Kamm, W. J., et al., "Transformation of Maize Cells and Regeneration of Fertile Transgenic Plants", The Plant Cell, 2(7), (1990), 603-618.
Guerineau, F., et al., "Effect of deletions in the cauliflower mosaic virus polyadenylation sequence on the choice of the polyadenylation sites in tobacco protoplasts.", Mol. Gen. Genet., 262(1-2), (1991), 141-144.
Guo, H. H., et al., "Protein tolerance to random amino acid change", Proc. Natl. Acad. Sci. USA, 101, (2004), 9205-9210.
Habu, Y., et al., "Amplified Restriction Fragment Length Polymorphism-based mRNA Fingerprinting Using a Single Restriction Enzyme That Recognizes a 4-bp Sequence", Biochem Biophys Res Commun., 234(2), (1997), 516-521.
Hayashimoto, A., et al., "A Polyethylene Glycol-Mediated Protoplast Transformation System for Production of Fertile Transgenic Rice Plants.", Plant Physiol., 93(3), (1990), 857-863.
He, X., et al., "Cloning and Characterization of a cDNA Encoding Diacylglycerol Acyltransferase from Castor Bean", Lipids, 39(4), (2004), 311-318.
He, X., et al., "Regulation of Diacylglycerol Acyltransferase in Developing Seeds of Castor", Lipids, 39(9), (2004), 865-871.
Hedrick, S. M., et al., "Sequence Relationships Between Putative T-cell Receptor Polypeptides and Immunoglobulins", Nature, 308(5955), (1984), 153-158.

Hill, M., et al., "Biolistic introduction of a synthetic Bt gene into elite maize.", Euphytica, 85(1-3), (1995), 119-123.
Hill, Margaret A, et al., "Functional Analysis of Conserved Histidines in ADP-Glucose Pyrophosphorylase from *Escherichia coli*", Biochem Biophys Res Commun., 244(2), (Mar. 17, 1998), 573-577.
Hinchee, M. A., et al., "Production of Transgenic Soybean Plants Using Agrobacterium-Mediated DNA Transfer", Nature Biotechnology, 6, (1988), 915-922.
Hobbs, D. H., et al., "Cloning of a cDNA encoding diacylglycerol acyltransferase from *Arabidopsis thaliana* and its functional expression", FEBS Lett., 452(3), (1999), 145-149.
Ichihara, K., et al., "Diacylglycerol Acyltransferase in Maturing Safflower Seeds: Its Influences on the Fatty Acid Composition of Triacylglycerol and on the Rate of Triacylglycerol Synthesis", Biochem Biophys. Acta, 958(1), (1988), 125-129.
Ishida, Y., et al., "High efficiency transformation of maize (*Zea mays* L.) mediated by *Agrobacterium tumefaciens*", Nature Biotechnology, 14(6), (1996), 745-750.
Ito, T., et al., "Fluorescent Differential Display Arbitrarily Primed RT-PCR Fingerprinting on an Automated DNA Sequencer", FEBS Lett., 351(2), (1994), 231-236.
J. Sambrook, et al., "Molecular Cloning: A Laboratory Manual", 2nd Ed., Cold Spring Harbor Laboratory Press, NY, (1989), pp. 16.6-16.8.
J. Sambrook, et al., "Molecular Cloning: A Laboratory Manual", Cold Spring Harbor Press, NY, (1989), pp. 9.31-9.58.
J. Sambrook, et al., "Molecular Cloning: A Laboratory Manual", Cold Spring Harbor Press, NY, (1989), pp. 7.39-7.52.
Jahne, A., et al., "Regeneration of Transgenic, Microspore-Derived, Fertile Barley", Theor. Appl. Genet., 89(4), (1994), 525-533.
Jako, C, et al., "Seed-Specific Over-Expression of an *Arabidopsis* CDNA Encoding a Diacylglycerol Acyltransferase Enhances Seed Oil Content and Seed Weight", Plant Physiology, 126(2), (2001), 861-874.
Jaworski, J., et al., "Industrial Oils from Transgenic Plants", Curr. Opin. Plant Biol., 6(2), (2003), 178-184.
Joshi, C. P., et al., "Putative polyadenylation signals in nuclear genes of higher plants: a compilation and analysis", Nucleic Acid Res., 15(23), (1987), 9627-9640.
Kacian, D. L., et al., "A Replicating RNA Molecule Suitable for a Detailed Analysis of Extracellular Evolution and Replication", Proc. Natl. Acad. Sci. USA, 69(10), (1972), 3038-3042.
Kalscheuer, R., et al., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1", J. Biol. Chem., 278(10), (2003), 8075-8082.
Katavic, V., et al., "Alteration of Seed Fatty Acid Composition by an Ethyl Methanesulfonate-Induced Mutation in *Arabidopsis thaliana* Affecting Diacylglycerol Acyltransferase Activity", Plant Physiol., 108(1), (1995), 399-409.
Kennedy, E. P., "Biosynthesis of Complex Lipids", Federation Proceedings., 20, (1961), 934-940.
King, A., "Cuticular wax biosynthesis in petunia petals: cloning and characterization of an alcohol-acyltransferase that synthesizes wax-esters", Planta, 226(2), (2007), 381-394.
Klaus, D., et al., "Increased fatty acid production in potato by engineering of acetyl-CoA carboxylase", Planta, 219, (2004), 389-396.
Klein, T. M., et al., "Factors Influencing Gene Delivery into *Zea mays* Cells by High Velocity Microprojectiles", Nature Biotechnology, 6(5), (1988), 559-563.
Klein, T. M., et al., "Genetic Transformation of Maize Cells by Particle Bombardment", Plant Physiology, 91(1), (1989), 440-444.
Klein, T. M., et al., "Transfer of Foreign Genes into Intact Maize Cells with High-Velocity Microprojectiles", Proc. Nat. Acad. Sci. USA, 85, (1988), 4305-4309.
Knothe, G., et al., "Kinematic viscosity of biodiesel fuel components and related compounds. Influence of compound structure and comparison to petrodiesel fuel components", Fuel, 84(9), (Jun. 2005), 1059-1065.
Knudsen, S., et al., "Transformation of the developing barley endosperm by particle bombardment.", Planta. 185, (1991), 330-336.

(56) References Cited

OTHER PUBLICATIONS

Koziel, M. G., et al., "Field Performance of Elite Transgenic Maize Plants Expressing as Insecticidal Protein Derived from *Bacillus thuringiensis*", Nature Biotechnology, 11(2), (1993), 194-200.

Koziel, M. G., et al., "Transgenic Maize for the Control of European Corn Borer and Other Maize Insect Pests", Ann. N Y Acad. Sci. 792(1), (1996), 164-171.

Krens, F. A., et al., "In vitro transformation of plant protoplasts with Ti-plasmid DNA.", Nature, 296, (1982), 72-74.

Kroon, J. T., et al., "Identification and functional expression of a type 2 acyl-CoA:diacylglycerol acyltransferase (DGAT2) in developing castor bean seeds which has high homology to the major triglyceride biosynthetic enzyme of fungi and animals", Phytochemistry, 67(23), (2006), 2541-2549.

Kunst, L., et al., "Fatty acid elongation in developing seeds of *Arabidopsis thaliana*", Plant Physiol. Biochem., 30(4), (1992), 425-434.

Lardizabal, K. D., et al., "DGAT1 is a new Diacylglycerol Acyltransferase Gene Family—Purification, Cloning and Expression in Insect Cells of two Polypeptides from Mortierella Ramanniana with Diacylglycerol Acyltransferase Activity", J. Biol. Chem., 276(42), (2001), 38862-38869.

Lardizabal, K. D., et al., "Purification of a Jojoba Embryo Wax Synthase, Cloning of its cDNA, and Production of High Levels of Wax in Seeds of Transgenic *Arabidopsis*", Plant Physiol., 122(3), (2000), 645-655.

Li, F., et al., "Identification of the Wax Ester Synthase/Acyl-Coenzyme A:Diacylglycerol Acyltransferase WSD1 Required for Stem Wax Ester Biosynthesis in *Arabidopsis*", Plant Physiology, 148(1), (2008), 97-107.

Liang, P., et al., "Differential Display of Eukaryotic Messenger RNA by Means of the Polymerase Chain Reaction", Science, 257(5072), (1992), 967-971.

Liang, P., et al., "Distribution and cloning of eukaryotic mRNAs by means of differential display: refinements and optimization", Nucleic Acids Research, 21 (14), (1993), 3269-3275.

Maniatis, T., et al., "Regulation of Inducible and Tissue-Specific Gene Expression.", Science, 236(4806), (1987), 1237-1245.

McCabe, D. E., et al., "Stable Transformation of Soybean (*Glycine max*) by Particle Acceleration", Nature Biotechnology, 6(8), (Aug. 1988), 923-926.

Mietiewska, E., et al., "Seed-Specific Heterologous Expression of a Nasturtium FAE Gene in *Arabidopsis* Results in a DramaticIncrease in the Proportion of Erucic Acid", Plant Physiol., 136(1), (2004), 2665-2675.

Milcamps, A., et al., "Isolation of a Gene-Encoding a 1,2 Diacylglycerol-sn-Acetyl-CoA Acetyltransferase from Developing Seeds of *Euonymus alatus*", J. Biol. Chem. 280(7), (2005), 5370-5377.

Millar, A. A., et al., "Very-long-chain fatty acid biosynthesis is controlled through the expression and specificity of the condensing enzyme", Plant J., 12(1), (1997), 121-131.

Mogen, B. D., et al., "Upstream sequences other than AAUAAA are required for efficient messenger RNA 3'-end formation in plants.", The Plant Cell, 2(12), (1990), 1261-1272.

Munroe, D., et al., "Tales of poly( A): a review", Gene, 91(2), (1990), 151-158.

Murphy, D. J., "Production of novel oils in plants", Curr Opin Biotechnol., 10, (1999), 175-180.

Nehra, N. S., et al., "Self-fertile transgenic wheat plants regenerated from isolated scutellar tissues following microprojectile bombardment with two distinct gene constructs", The Plant Journal, 5(2), (1994), 285-297.

Nykiforuk, C. L., et al., "Characterization of cDNAs Encoding Diacylglycerol Acyltransferase from Cultures of *Brassica napus* and Sucrose-Mediated Induction of Enzyme Biosynthesis", Biochem. Biophys Acta, 1580(2-3), (2002), 95-109.

Odell, J., et al., "Identification of DNA Sequences Required for Activity of the Cauliflower Mosaic Virus 35S Promoter", Nature, 313, (1985), 810-812.

Ohlrogge, J., et al., "Lipid Biosynthesis", The Plant Cell, 7(7), (1995), 957-970.

Okubo, K., et al., "Large Scale cDNA Sequencing for Analysis of Quantitative and Qualitative Aspects of Gene Expression", Nat. Genet., 2(3), (1992), 173-179.

Paszkowski, J., et al., "Direct Gene Transfer to Plants", The EMBO Journal, 3(12), (1984), 2717-2722.

Pillai, M. G., et al., "Biosynthesis of Triacylglycerol Molecular Species in an Oleaginous Fungus, *Mortierella ramanniana* var. *angulispora*", J. Biochem, 132(1), (2002), 121-126.

Proudfoot, N. J., "Poly(A) signals", Cell, 64, (1991), 671-674.

Riggs, C. D., et al., "Stable transformation of tobacco by electroporation: evidence for plasmid concatenation", Proc. Nat!. Acad. Sci. USA, 83(15), (1986), 5602-5606.

Rosenberg, A. H., et al., "Vectors for selective expression of cloned DNAs by T7 RNA Polymerase", Gene, 56 (1), (1987), 125-135.

Routaboul, C, et al., "Proposal for a new UVA protection factor: use of an in vitro model of immediate pigment darkening.", European Journal of Dermatology, 12(5), (Sep.-Oct. 2002), 439-44.

Routaboul, J. M., et al., "The TAG1 locus of *Arabidopsis* encodes for a diacylglycerol acyltransferase", Plant Physiol. Bioch., 37(11), (1999), 831-840.

Saha, S., et al., "Cytosolic Triacylglycerol Biosynthetic Pathway in Oilseeds. Molecular Cloning and Expression of Peanut Cytosolic Diacylglycerol Acyltransferase", Plant Physiology, 141(4), (2006), 1533-1543.

Sandager, L., et al., "Storage Lipid Synthesis Is Non-essential in Yeast", J. of Biological Chem., 277(8), (2002), 6478-6482.

Sanfacon, H., et al., "A dissection of the cauliflower mosaic virus polyadenylation signal", Genes Dev., 5, (1991), 141-149.

Sanford, J. C., et al., "Delivery of Substances into Cells and Tissues Using a Particle Bombardment Process", Particulate Sci. Technol., 5(1), (1987), 27-37.

Schell, J., "Transgenic Plants as Tools to Study the Molecular Organization of Plant Genes", Science, 237(4819), (1987), 1176-1183.

Schena, Mark, "Quantitative Monitoring of Gene Expression Patterns with a Complementary DNA Microarray", Science, 270(5235), (1995), 467-470.

Shanklin, J., et al., "Desaturation and Related Modifications of Fatty Acids", Annual Review Plant Physiol. Plant Mol. Biol., 49, (1998), 611-641.

Shih, Giles, "Multiple lysophosphatidic acid acyltransferases in *Neisseria meningitidis*", Molecular Microbiology (1999) 32(5), 942-952, (1999), 942-952.

Shimamoto, K., et al., "Fertile transgenic rice plants regenerated from transformed protoplasts", Nature, 338(6212), (1989), 274-276.

Shimkets, R. A., et al., "Gene Expression Analysis by Transcript Profiling Coupled to a Gene Database Query", Nat.Biotechnol. 17(8), (1999), 798-803.

Shockey, J. M., et al., "Tung Tree DGAT1 and DGAT2 Have Nonredundant Functions in Triacylglycerol Biosynthesis and are Localized to Different Subdomains of the Endoplasmic Reticulum", The Plant Cell, 18(9), (2006), 2294-2313.

Singh, S. P., et al., "Metabolic Engineering of New Fatty Acids in Plants", Curr Opin. Plant Biol., 8(2), (2005), 197-203.

Smith, S. J., "Obesity resistance and multiple mechanisms of triglyceride synthesis in mice lacking Dgat", Nat. Genet., 25(1), (2000), 87-90.

Somers, D. A., et al., "Fertile, Transgenic Oat Plants.", Nature Biotechnology, 10(12), (1992), 1589-1594.

Song, K., et al., "A Method for Examining Expression of Homologous Genes in Plant Polyploids", Plant Mol Biol. 26(4), (1994), 1065-1071.

Spencer, T. M., et al., "Bialaphos selection of stable tranformants from maize cell culture", Theoretical and Applied Genetics 79(5), (1990), 625-631.

Stahl, U., et al., "Cloning and Functional Characterization of a Phospholipid Diacylglycerol Acyltransferase from *Arabidopsis*", Plant Physiol., 135, (2004), 1324-1335.

Staub, J. M., et al., "Accumulation of D1 polypeptide in tobacco plastids is regulated via the untranslated region of the psbA mRNA.", EMBO J., 12(2), (1993), 601-606.

(56) References Cited

OTHER PUBLICATIONS

Staub, J. M., et al., "Long Regions of Homologous DNA are Incorporated into the Tobacco Plastid Genome by Transformation.", The Plant Cell, 4(1), (1992), 4-39.

Stone, B., et al., "Targeted RNA fingerprinting: the cloning of differentially-expressed cDNA fragments enriched for members of the zinc finger gene family", Nucleic Acids Res. 22(13), (1994), 2612-2618.

Stone, S. J., "Lipopenia and Skin Barrier Abnormalities in DGAT2-deficient Mice", J. Biol. Chem., 279(12), (2004), 11767-11776.

Svab, Z., et al., "High-frequency plastid transformation in tobacco by selection for a chimeric aadA gene.", Proc. Nat!. Acad. Sci. USA,. 90(3), (1993), 913-917.

Svab, Z., et al., "Stable transformation of plastids in higher plants", Proc. Nat!. Acad. Sci. USA, 87, (1990), 8526-8530.

Thelen, J J., et al., "Metabolic Engineering of Fatty Acid Biosynthesis in Plants.", Metabolic Engineering, 4(1), (2002), 12-21.

Torbert, K. A., et al., "Use of paromomycin as a selective agent for oat transformation", Plant Cell Reports, 14, (1995), 635-640.

Umbeck, P., et al., "Genetically transformed cotton (*Gossypium hirsutum* L.) plants.", Nature Biotechnology, 5, (1987), 263-266.

Vasil, V., et al., "Rapid Production of Transgenic Wheat Plants by Direct Bombardment of Cultured immature Embryos", Nature Biotechnology, 11, (1993), 1553-1558.

Velculescu, V. E., et al., "Serial Analysis of Gene Expression", Science, 270(5235), (1995), 484-487.

Vieira, J., et al., "The pUC plasmids, an M13mp7-derived system for insertion mutagenesis and sequencing with synthetic universal primers", Gene 19(3), (1982), 259-268.

Vogel, G., et al., "Cholinephosphotransferase and Diacylglycerol Acyltransferase—Substrate Specificities at a Key Branchpoint in Seed Lipid Metabolism", Plant Physiol. 110, (1996), 923-931.

Voss, S. D., et al., "The Role of Enhancers in the Regulation of Cell-Type-Specific Transcriptional Control", Trends Biochem. Sci., 11, (1986), 287-289.

Wan, Y., et al., "Generation of Large Numbers of Independently Transformed Fertile Barley Plants", Plant Physiol., 104, (1994), 37-48.

Wang, N., et al., "Assessment of FAE1 polymorphisms in three *Brassica* species using EcoTILLING and their association with differences in seed erucic acid contents", BMC Plant Biology, 10: 137, (2010), 1-11.

Wang, X., et al., "Direct Sequencing of DNA Isolated from mRNA Differential Display", Biotechniques 18(3), (1995), 448-453.

Weeks, J. T., et al., "Rapid Production of Multiple Independent Lines of Fertile Transgenic Wheat (*Triticum aestivum*)", Plant Physiol., 102, (1993), 1077-1084.

Weising, K., et al., "Foreign Genes in Plants: Transfer, Structure, Expression and Applications", Annu. Rev. Genet. 22, (1988), 421-477.

White, J., et al., "A cassette containing the bar gene of *Streptomyces hygroscopicus:* a selectable marker for plant transformation", Nucleic Acids Research, 18(4), (1990), p. 1062.

Wu, D. Y., et al., "The Ligation Amplification Reaction (LAR)—Amplification of Specific DNA Sequences Using Sequential Rounds of Template-Dependent Ligation", Genomics, 4(4), (1989), 560-569.

Yen, C.-L. E., et al., "Thematic Review Series: Glycerolipids. DGAT enzymes and triacylglycerol biosynthesis", J. Lipid Res., 49, (2008), 2283-2301.

Zhang, L., et al., "Gene Expression Profiles in Normal and Cancer Cells", Science 276, (1997), 560-569.

Zhang, M., et al., "DGAT1 and PDAT1 Acyltransferases Have Overlapping Functions in *Arabidopsis* Triacylglycerol Biosynthesis and Are Essential for Normal Pollen and Seed Development", Plant Cell, 21(12), (2009), 3885-3901.

Zou, J., et al., "Modification of Seed Oil Content and Acyl Composition in the Brassicaceae by Expression of a Yeast sn-2 Acyltransferase Gene", Plant Cell, 9(6), (1997), 909-923.

Zou, J., et al., "The *Arabidopsis thaliana* TAG1 mutant has a mutation in a diacylglycerol acyltransferase gene", Plant J. 19(6), (1999), 645-653.

\* cited by examiner

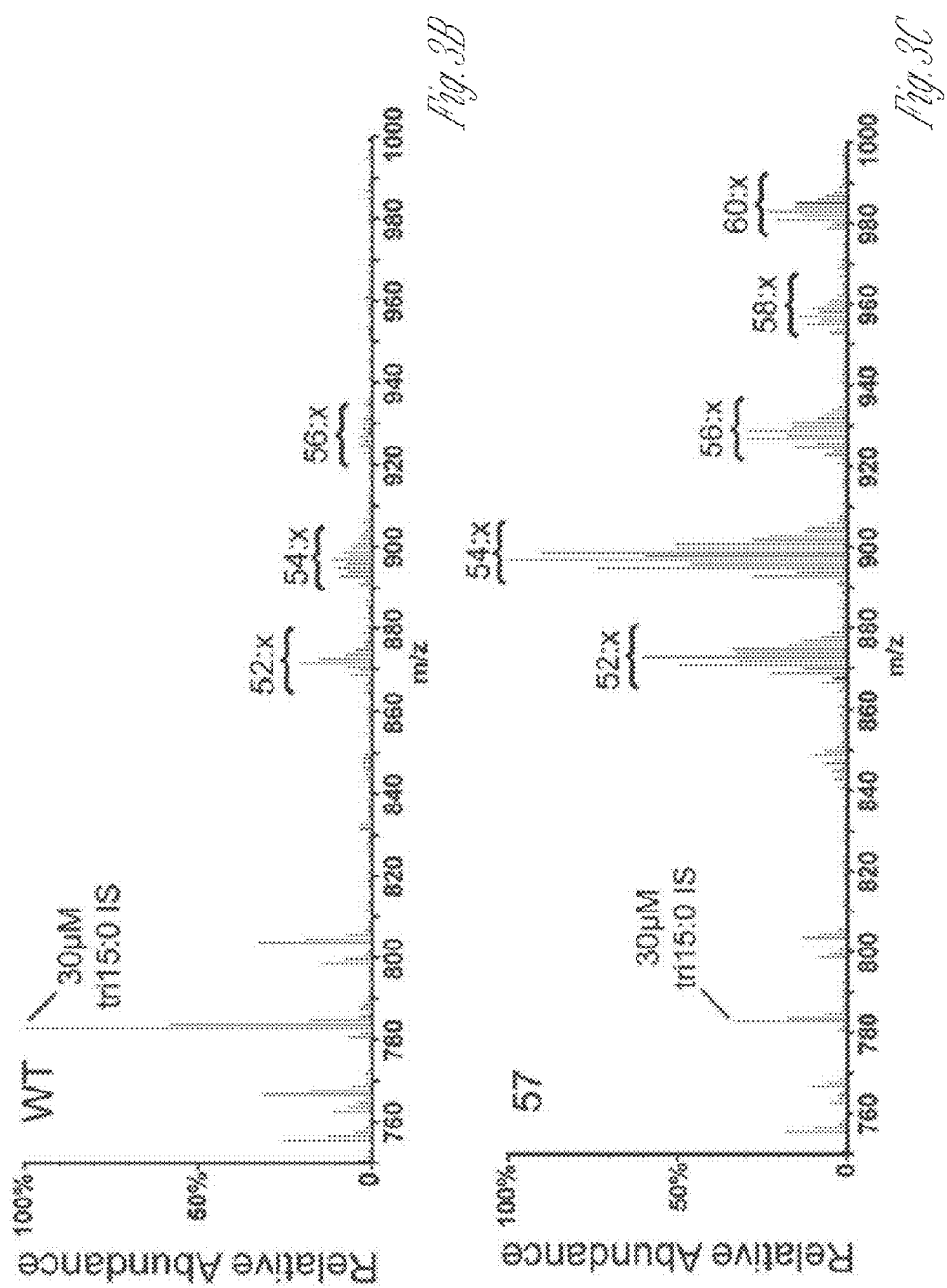

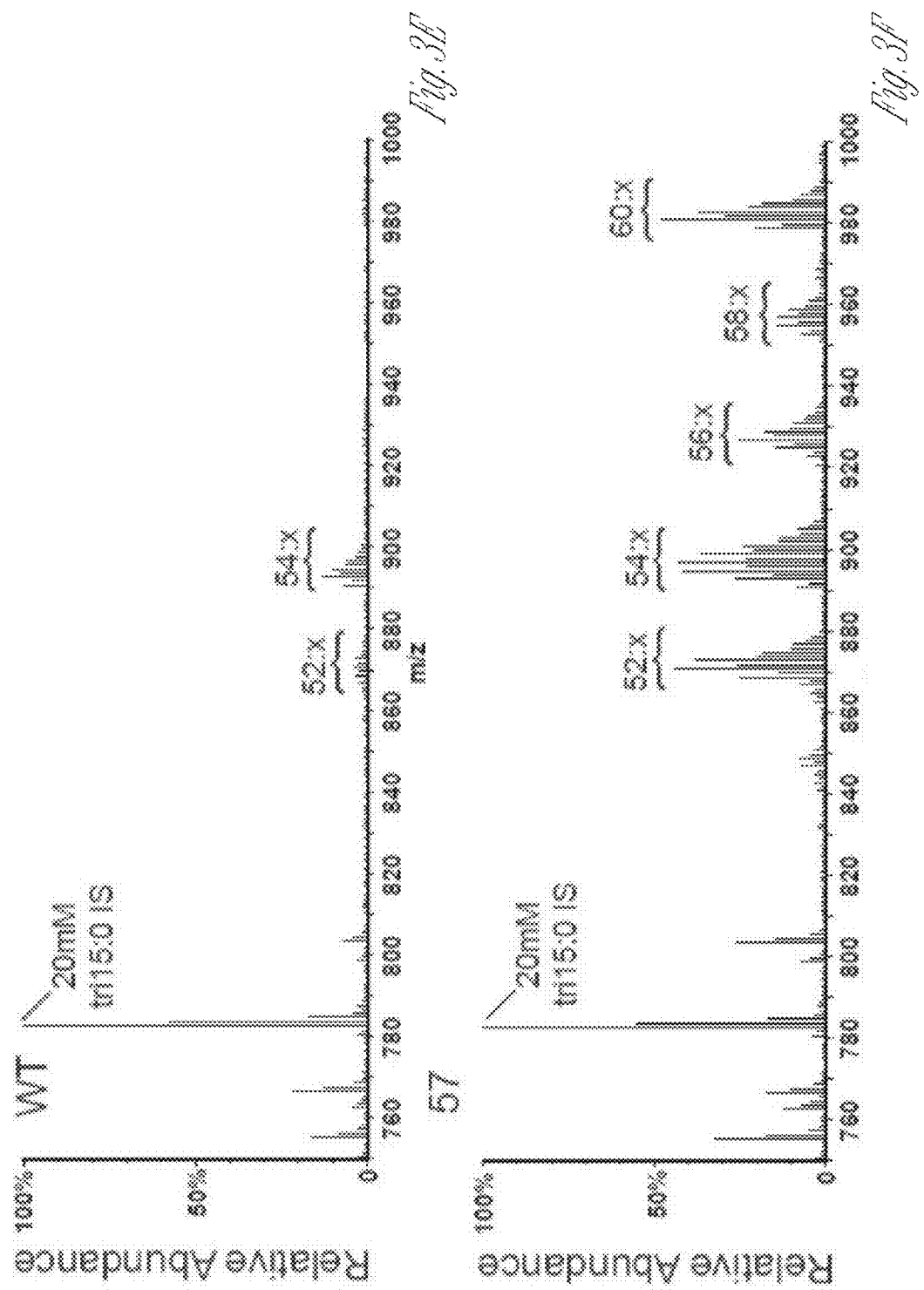

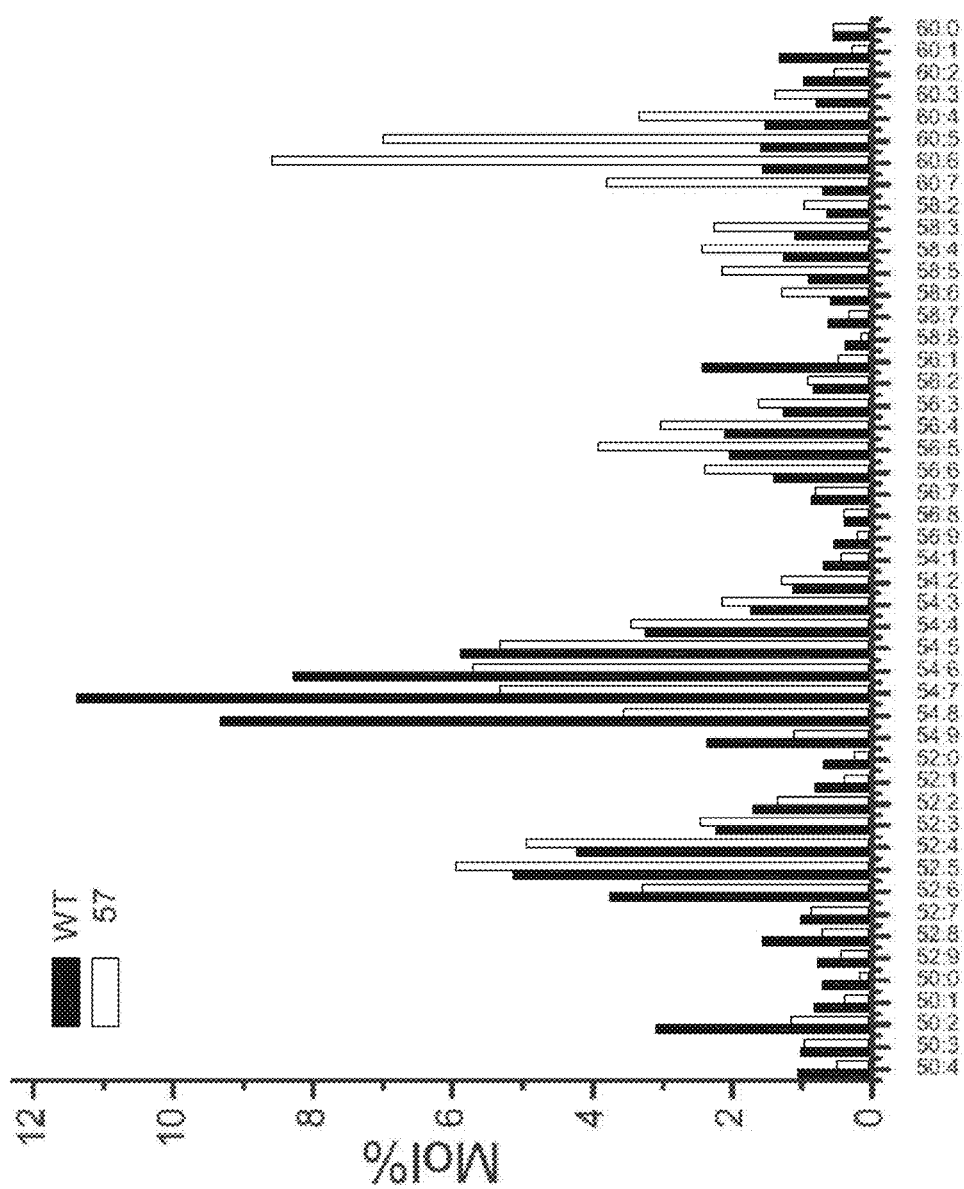

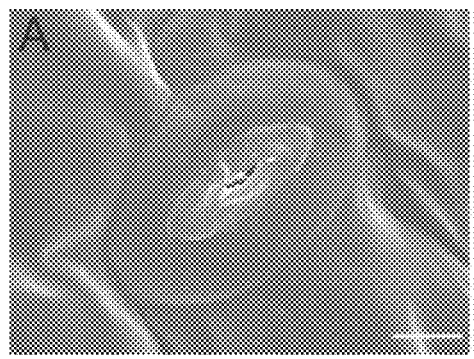
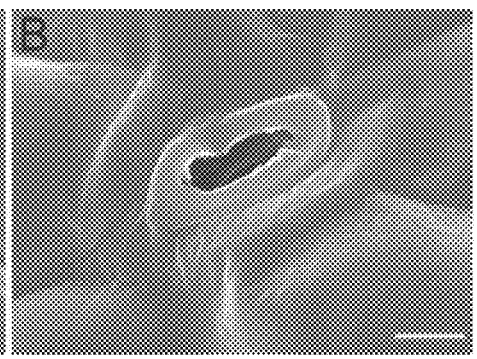
Fig. 6A        Fig. 6B
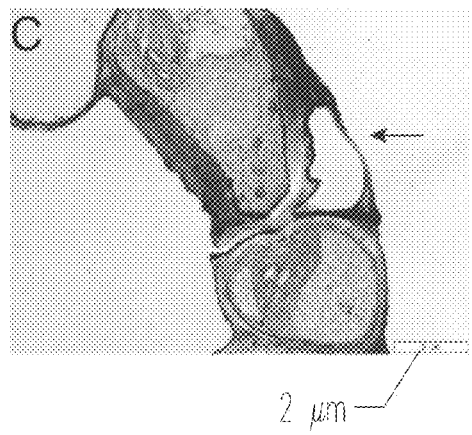# 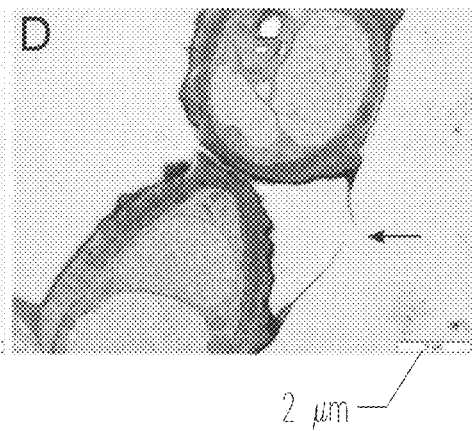
Fig. 6C        Fig. 6D

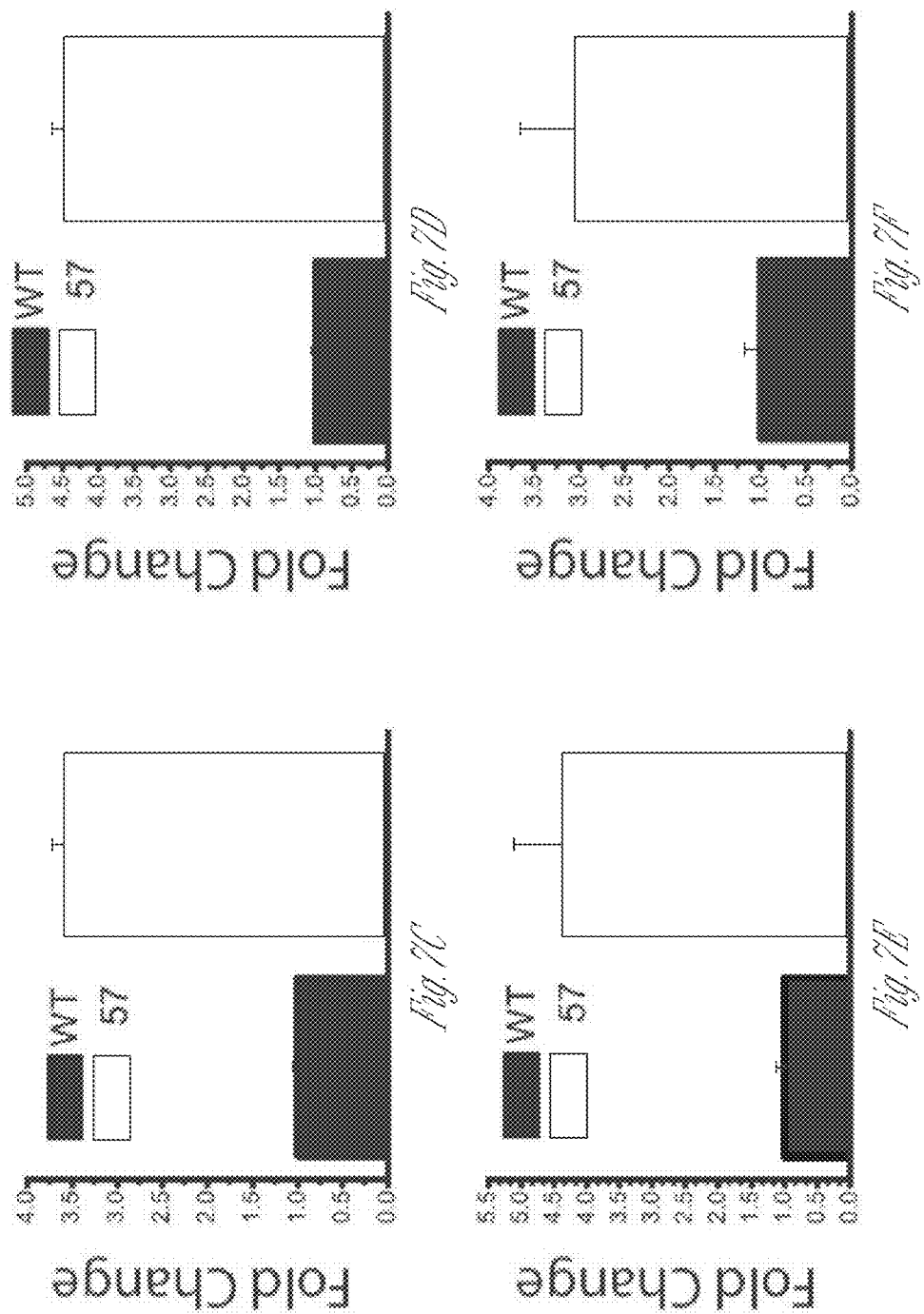

INCREASED CALORIC AND NUTRITIONAL CONTENT OF PLANT BIOMASS

This application claims benefit of priority to the filing date of U.S. Provisional Application Ser. No. 61/928,559, filed Jan. 17, 2014, the contents of which are specifically incorporated herein by reference in their entity.

GOVERNMENT FUNDING

This invention was made with government support under DE-FCO2-07ER64494, DE-FG02-91ER20021, DE-FG02-98ER20305 awarded by the U.S. Department of Energy and FA9550-11-1-0264 awarded by the U.S. Air Force Office of Scientific Research. The government has certain rights in the invention.

BACKGROUND

Oil produced by plants is one of the most energy-rich forms of reduced carbon available from nature. As crude oil supply declined, plant oils are gaining increasing interest as substitutes for petroleum-derived and non-renewable fuels. As one example, Hu et al., describes the use of microalgal triacylglycerols (TAGs) as feedstocks for biofuel production (Hu et al., The Plant J., 54(4):621-639 (2008).

One of the biggest challenges in using plant oils is the limited growing areas available for plants whose oil is designated for the biofuel industry along with finite supplies of fertilizers, pesticides, and resources for growing these plants and processing their oils. Thus, compositions and methods are needed for increasing the amount of harvestable amount of plant oils from plants per acre for decreasing the cost per liter of plant oil. Further, compositions and methods are needed for growing oil crop plants for increasing the amount of harvestable oil in plants destined as sources of biofuel.

SUMMARY

As described herein, expression of Diacylglycerol Acyltransferase Type Two (DGTT) enzymes from nucleic acid constructs can alter acyl carbon partitioning in plant vegetative tissues. Such expression can increase acyl-CoA-dependent triacylglycerol synthesis and thereby increase the lipid content and nutritional value of leaves and other vegetative tissues. For example, the DGTT enzymes can be DGTT2 or DGTT3 enzymes.

Thus, plant cells, plant seeds, and plants are described herein that have a nucleic acid construct that includes a nucleic acid encoding a polypeptide with at least 80% sequence identity with an amino acid sequence selected from the group of SEQ ID NO:1, 3 5, and 7, that is operably linked to a heterologous promoter operable in at least one plant tissue.

Also described herein is method that includes:
(a) transfecting a plant tissue or plant cell with a nucleic acid construct that includes a nucleic acid encoding a polypeptide with at least 40% sequence identity with an amino acid sequence selected from the group of SEQ ID NO:1, 3 5, and 7, that is operably linked to a heterologous promoter operable in at least one plant tissue; and
(b) growing the tissue or the cell into a whole plant.

In addition a method is described herein that includes:
(a) growing a plant from a seed with a nucleic acid construct that includes a nucleic acid encoding a polypeptide with at least 40% sequence identity with an amino acid sequence selected from the group of SEQ ID NO:1, 3 5, and 7, that is operably linked to a heterologous promoter operable in at least one plant tissue; and (b) harvesting lipid or oil from the plant or a portion of the plant.

DESCRIPTION OF THE FIGURES

FIG. 1A schematically illustrates a phylogenetic tree of *Chlamydomonas* DGTT1-5, compared to DGAT2s from other species: *Arabidopsis thaliana* (NP_566952.1), *Ostreococcus tauri* (XP_003083539.1), *Saccharomyces cerevisiae* (NP_014888.1), *Ricinus communis* (DQ923084.1), and *Vernicia fordii* (DQ356682.1). FIG. 1B shows schematic diagrams of the predicted structures of DGTT1, DGTT2, DGTT3, DGTT4 and DGTT1-5. The boxes indicate predicted transmembrane domains (TM), and the larger boxes indicate the conserved enzymatic domain (DAGAT). FIG. 1C graphically illustrates triacylglycerol (TAG) levels of yeast transformants with DGTT1, DGTT2, DGTT3, DGTT4, or DGTT1-5 expression cassettes. Electrospray ionization mass spectrometry (ESI-MS) quantification of TAG levels extracted from transformed yeast. The total amount of TAG was normalized based on the dry weight of the yeast. Tritridecanoin (tri13:0) and tripentadecanoin (tri15:0) TAGs were added as internal standards (n=4; average±SD). H1266 indicates the empty vector control.

FIG. 2A shows an autoradiograph of $[1-^{14}C]$-16:0-acyl-CoA radiolabeled lipids obtained from microsomes of DGTT yeast transformants after separation on a TLC plate. FIG. 2B shows an autoradiograph of $[1-^{14}C]$-18:0-acyl-CoA radiolabeled lipids separated on a TLC plate. Signals representing triacylglycerol (TAG), free fatty acids (FFA), and diacylglycerol (DAG) are indicated. H1266 indicates the empty vector control. FIG. 2C graphically illustrates competition of unlabeled acyl-CoA with 1.725 nmol of $[1-^{14}C]$-16:0-acyl-CoA in each competition reaction. Competitors consisting of 1.725 nmol of unlabeled 16:0-acyl-CoA, 18:1-acyl-CoA, or 22:1-acyl-CoA were added to the respective reactions and compared with a no-competitor control (0). The newly-synthesized $^{14}C$-labeled TAGs were separated and quantified by scintillation counting. The results were normalized by subtracting the background (in dpm), and then dividing all the results by the no-competitor control (n=3; average±SD). FIG. 2D shows images illustrating the phenotypes of 10-12-day-old seedlings of wild type (WT) and DGTT2 transgenic lines (14, 22, 46, 52, and 57) after growth on ½ MS medium supplemented with 1% sucrose. FIG. 2E graphically illustrates hypocotyl length of 10-12-day-old seedlings of wild type (WT) and DGTT2 transgenic lines (14, 22, 46, 52, 57) after growth on ½ MS medium supplemented with 1% sucrose. FIG. 2F graphically illustrates the chlorophyll content of WT and DGTT2 transgenic lines (14, 22, 46, 52, 57) grown on ½ MS medium supplemented with 1% sucrose. Chlorophyll was extracted from 15-day-old seedlings with 80% acetone, and its concentration determined spectrophotometrically, *t-test significant at $p<0.05$ or **$p<0.01$ versus wild type (n=3; average±SD). FIG. 2G graphically illustrates quantification of DGTT2 mRNA by qRT-PCR in 15-day-old seedlings of WT and DGTT2 transgenic lines (14, 22, 46, 52, 57) grown on ½ MS medium supplemented with 1% sucrose (n=3; average±SD).

FIG. 3A-3G illustrate that DGTT2 leads to the accumulation of TAG with very long chain fatty acids (VLCFA) in *Arabidopsis* seedlings (15-day-old) and soil grown plants (6-week-old). FIG. 3A graphically illustrates the quantity of TAGs as detected by ESI-MS quantification of TAGs in neutral lipid extracts of wild type and homozygous transgenic (14, 22, 46, 52, 57) seedlings and soil grown plants (n=4; average±SD). See website plantmetabolism.cns.msu.edu/Symposium.aspx. FIG. 3B graphically illustrates the relative abundance of various TAGs as detected by positive-ion ESI mass spectral analysis of neutral lipid extracts from wild-type seedlings. Tritridecanoin (tri13:0) and tripentadecanoin (tri15:0) TAGs were added as internal standard. FIG. 3C graphically illustrates the relative abundance of various TAGs as detected by positive-ion ESI ion mass spectral analysis of neutral lipid extracts from transgenic line 57 seedlings. Tritridecanoin (tri13:0) and tripentadecanoin (tri15:0) TAGs were added as internal standards. FIG. 3D illustrates the relative abundance of various TAGs as detected by ESI-MS analysis of neutral lipid extracts of line 57. Shown are the daughter fragment ions from TAGs with [M+NH4]$^+$ adducts with m/z values of 929, 957 and 983. The m/z values were rounded up to the nearest nominal mass. FIG. 3E-3G graphically illustrates the relative abundance of long and very long chain fatty acids (VLCFA) in soil grown plants (6-week-old) by ESI-MS/MS. FIG. 3E illustrates the relative abundance of various TAGs as detected by positive-ion ESI mass spectra of neutral lipid extracts from wild type seedlings (n=4; average±SD). FIG. 3F illustrates the relative abundance of various TAGs as detected by positive-ion ESI mass spectra of neutral lipid extracts from homozygous DGTT2 line 57 seedlings (n=4; average±SD). Tritridecanoin (tri13:0) and tripentadecanoin (tri15:0) TAGs were added as internal standards. FIG. 3G illustrates the relative abundance of various TAGs as detected by ESI-MS$^2$ analysis of neutral lipid extracts of line 57. Shown are the daughter fragment peaks from TAGs with [M+NH4]$^+$ adducts with m/z values of 929, 957 and 983. The m/z values indicated in the spectra were rounded up to the nearest nominal mass.

FIG. 4A-4I shows that oil droplets are abundant in leaves of DGTT2 transgenic line 57. FIG. 4A shows a confocal fluorescence image of line 57 leaf mesophyll cells illustrating that oil droplets (arrows, lighter spots) are present. The size bar is equivalent to 5 μm. FIG. 4B shows a confocal fluorescence image of line 57 leaf mesophyll cells showing chloroplasts (grey). The size bar is equivalent to 5 μm. FIG. 4C shows a confocal fluorescence image of line 57 leaf mesophyll cells showing both chloroplasts (grey) and oil droplets (lighter spots). The size bar is equivalent to 5 μm. FIG. 4D-4F shows confocal fluorescence images of wild type leaf samples from of the same age as line 57 (6 week-old, soil-grown). The size bar is equivalent to 5 μm. FIG. 4G shows a TEM image of the first leaf pair from a 6-week-old wild type seedling. Starch granules (S) are indicated. The size bar is equivalent to 500 μm. FIG. 4H shows a TEM image of the first leaf pair from 6-week-old transgenic line 57 seedling. Oil droplets (OD), and chloroplasts (CH) are indicated. The size bar is equivalent to 500 μm. FIG. 4I graphically illustrates the mole percentage of long and very long chain fatty acids in 6-week-old soil grown DGTT2 line 57 and wild-type plants as detected by ESI-MS/MS.

FIG. 5A-5G illustrates the effect of DGTT2 on cuticular wax production in *Arabidopsis*. FIG. 5A shows a transmission electron micrograph of a wild type leaf epidermal section. FIG. 5B shows a transmission electron micrograph of DGTT2 transgenic line 57 leaf epidermal section. Oil droplets (OD) were only present in the transgenic line. The arrows point at the cuticle, CT, showing a layer of osmium dense material. The cell wall (CW) is indicated. The size bar is equivalent to 200 nm. FIG. 5C shows a scanning electron micrograph of wild type leaves. FIG. 5D shows a scanning electron micrograph of transgenic line 57 leaves. Rod-like wax crystals are observed on the surface of wild type plants (FIG. 5C), but are much less abundant on the surface of cells of the transgenic line (FIG. 5D). The size bar is equivalent to 5 μm. FIG. 5E graphically illustrates the leaf epicuticular wax profile of wild-type plants and transgenic lines as indicated. The number of carbons in the respective compounds is indicated, the symbol * indicates significance at $p<0.05$ while the symbol ** indicates significance at $p<0.01$ compared with wild type by one-way ANOVA with post hoc Dunnett's test (n=3; average±SD). FIG. 5F graphically illustrates the total fatty acid content (TAG in nmoles/mg dry weight) of soil-grown 6-week-old leaves from wild type and homozygous transgenic plants expressing DGTT2 as detected with a gas chromatography flame ionization detector (GC-FID). FIG. 5G graphically illustrates the leaf fatty composition (mole percentage) of wild type and DGTT2 transgenic lines 22 and 57. *t-test significant at $p<0.05$ or $p<0.01$ or *$p<0.001$ versus wild type (n=3; average±SD).

FIG. 6A-6I illustrates the effect of DGTT2 on cutin and related phenotypes in *Arabidopsis*. FIG. 6A shows SEM images of stomata from the adaxial surface of wild type leaves. The size bar is equivalent to 5 μm. FIG. 6B shows SEM images of stomata from the adaxial surface of line 57 leaves. The size bar is equivalent to 5 μm. FIG. 6C shows a TEM image of a section of wild type leaf guard cells. The arrow indicates the cuticular ledge in the guard cells. The size bar is equivalent to 2 μm. FIG. 6D shows a TEM image of a section of line 57 leaf guard cells. The arrow indicates the cuticular ledge in the guard cells. The size bar is equivalent to 2 μm. FIG. 6E graphically illustrates the leaf cutin monomer content profile of wild type and DGTT2 transgenic lines 14, 22, and 57. The symbol * indicates significance at $p<0.001$ compared with wild type by one-way ANOVA with post hoc Dunnett's test (n=4; average±SD). FIGS. 6F-6I illustrate the abundance of sphingolipids in leaves of wild type and line 57 plants. FIG. 6F shows the relative abundances of individual ceramide (Cer) molecular species containing t18:1 long chain bases in wild type and line 57. FIG. 6G shows the relative abundances of individual ceramide (Cer) molecular species containing dl 8:1 long chain bases in wild type and line 57. FIG. 6H illustrates the distribution of total glycosyl inositolphosphoceramide (GIPC) species containing d18:0, d18:1, t18:0, and t18:1 long chain bases, as determined by high resolution/accurate mass MS. FIG. 6I illustrates the relative abundances of individual glucosylceramide (GlcCer) molecular species containing dl 8:1 long chain bases in wild type and line 57, t-test significant at $p<0.01$ versus wild type (n=3; average±SD).

FIG. 7A-7F illustrates sphingolipid molecular species in *Arabidopsis* as detected by high resolution/accurate mass spectrometry. FIG. 7A graphically illustrates the relative abundances of individual glycosyl inositolphosphoceramide (GIPC) molecular species containing t18:1 long chain bases in wild type and line 57 plant leaves, *t-test significant at $p<0.05$ or $p<0.01$ or *$p<0.001$ versus wild type (n=3; average±SD). FIG. 7B graphically illustrates the relative abundances of individual glucosylceramide (GlcCer) molecular species containing t18:1 long chain bases in wild type and line 57 leaves, *t-test significant at p<0.05 or p<0.01 or *p<0.001 versus wild type (n=3; average±SD). FIG. 7C-7F graphically illustrates relative gene expression levels in 6-week-old wild type and line 57 leaves of different genes in three independent experiments carried out with three independent mRNA preparations (n=3; average±SD). FIG. 7C shows WSD1 (wax ester synthase and diacylglycerol acyltransferase, At5g37300) expression levels in 6-week-old wild type and line 57 plants. FIG. 7D shows HXXXD-type acyl-transferase (At1g65450) in 6-week-old wild type and line 57 plants. FIG. 7E shows Qua-Quine Starch (QQS, At3g30720) expression in 6-week-old wild type and line 57 plants. FIG. 7F shows cytosolic beta-amylase (At4g15210) expression in 6-week-old wild type and line 57. Three independent experiments carried out with three independent mRNA preparations (n=3; average±SD).

FIG. 8A-8G illustrates the growth and starch content of wild type and DGTT2 transgenic line 57. FIG. 8A graphically illustrates the dry weight of the aerial parts of *Arabidopsis* plants was measured on a weekly basis for a period of 8 weeks. Each time point represents the average value of at least six individual plants. Square symbols represent wild type biomass, and round symbols represent transgenic line 57 biomass, *t-test significant at p<0.05 or p<0.01 or *p<0.001 versus wild type (n=6; average±SD). FIG. 8B illustrates the leaf starch content of 6-week-old of wild type (WT) and line 57 plants, t-test significant at p<0.01 versus wild type (n=5; average±SD). FIG. 8C graphically illustrates the type and amount of individual leaf glycerolipids of 15-day-old DGTT2 transgenic (22 and 57) and wild type plants. Measured lipids were: monogalactosyl-diacylglycerol (MGDG), phosphatidylglycerol (PG), digalactosyl-diacylglycerol (DGDG), sulfoquinovosyl-diacylglycerol (SQDG), phosphatidylinositol (PI), phosphatidylethanolamine (PE), and phosphatidylcholine (PC). FIG. 8D illustrates the MGDG fatty acid composition of transgenic lines and wild type leaves. FIG. 8E illustrates the DGDG fatty acid composition of transgenic lines and wild type leaves. MGDG and DGDG isolated in FIG. 8C was subjected to fatty acid methyl ester quantification. FIG. 8F illustrates the fatty acid content (mole percentage) of wild type and DGTT2 transgenic lines 22 and 57. FIG. 8G illustrates the fatty acid composition of wild type and DGTT2 transgenic lines 22 and 57. *t-test significant at p<0.05 or p<0.01 or *p<0.001 versus wild type (n=3; average±SD).

FIG. 9A shows photographs of representative wild-type and DGTT2 transgenic plants at the end of *Spodoptera exigua* feeding trial. FIG. 9B shows photographs of representative *Spodoptera exigua* larvae grown on wild-type and DGTT2 transgenic plants at the end of feeding trial. FIG. 9C graphically illustrates the average fresh weight of insects, **t-test significant at p<0.01 versus wild type hosts (n=95; average±SD). FIG. 9D graphically illustrates JA-Ile accumulation in leaf tissue collected from undamaged control plants and those damaged during 14 day of insect feeding (n=5; average±SD). FIG. 9E-9I graphically illustrates the glycerolipid composition of DGTT2 transgenic lines 22 and 57, compared to wild type plants (6-week-old plants). FIG. 9E graphically illustrates the total content of individual leaf glycerolipids of 6-week-old DGTT2 transgenic lines and wild type plants grown on soil. Measured lipids are monogalactosyldiacylglycerol (MGDG), phosphatidylglycerol (PG), digalactosyldiacylglycerol (DGDG), sulfoquinovosyldiacylglycerol (SQDG), phosphatidylethanolamine (PE), phosphatidylinositol (PI) and phosphatidylcholine (PC). FIG. 9F graphically illustrates the MGDG fatty acid composition of wild type and DGTT2 transgenic lines. FIG. 9G graphically illustrates the DGDG fatty acid composition of wild type and DGTT2 transgenic lines. MGDG and DGDG were subjected to fatty acid methyl ester quantification. FIG. 9H graphically illustrates the total fatty acid content of wild type (WT) and DGTT2 transgenic lines 22 and 57. FIG. 9I graphically illustrates the fatty acid composition of wild type (WT) and DGTT2 transgenic lines 22 and 57. *t-test significant at p<0.05 or p<0.01 or *p<0.001 versus wild type (n=3; average±SD).

FIG. 10A shows a schematic overview of altered diversion of acyl-CoAs groups from other pathways by DGTT2 in *Arabidopsis* leaves. The dashed arrows (labeled DGTT2) represent the activity of DGTT2 in channeling acyl-CoAs from wax/cutin/sphingolipids to the synthesis of TAGs with VLCFAs in the transgenic lines. The following abbreviations were used: CW, cell wall; PM, plasma membrane; ER, endoplasmic reticulum; G3P, glycerol-3-phosphate; LPA, lyso-phosphatidic acid; LPC, lysophosphatidylcholine; PC, phosphatidylcholine; PA, phosphatidic acid; DAG, diacylglycerol; TAG, triacylglycerol; FAE, fatty acid elongation; FAS, fatty acid synthesis. FIG. 10B graphically illustrates the total amount of diacylglycerol (DAG) of 6-week-old wild-type and DGTT2 transgenic plants grown on soil. FIG. 10C graphically illustrates the total amount of phosphatidic acid (PA) of 6-week-old wild-type plants and DGTT2 transgenic lines grown on soil. FIG. 10D graphically illustrates the DAG fatty acid composition of leaves of wild type and DGTT2 transgenic lines. FIG. 10E graphically illustrates the phosphatidic acid (PA) fatty acid composition of leaves of wild type and DGTT2 transgenic lines. (n=3; average±SD).

DETAILED DESCRIPTION

Figure 1A:
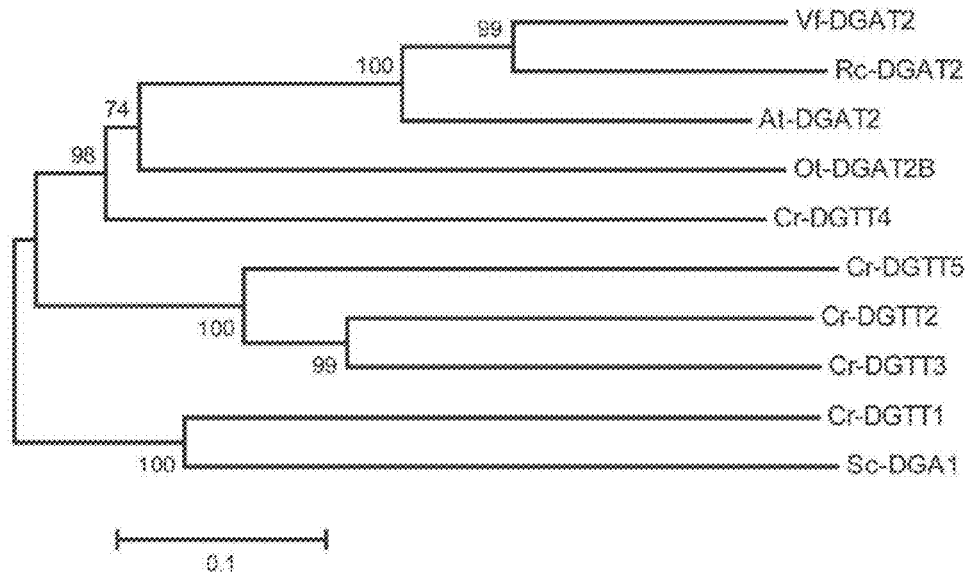
FIG. 1A-1C illustrate the relationship, structures identified, and yeast expression of *Chlamydomonas* type 2 Diacylglycerol Acyltransferase Type Two (DGTT) enzymes.

As described herein, algal Diacylglycerol Acyltransferase Type Two (DGTT) enzymes can alter acyl carbon partitioning in plant vegetative tissues. Expression of such enzymes can increase acyl-CoA-dependent triacylglycerol synthesis and thereby increase the lipid content and nutritional value of the plants' tissues. For example, the lipid content of plant tissues such as leaves can be increased by expression of heterologous nucleic acids that express algal Diacylglycerol Acyltransferase Type Two (DGTT) enzymes.

Diacylglycerol Acyltransferase Type Two (DGTT)

Diacylglycerol acyltransferase type two (DGTT) enzymes can catalyze the transfer of fatty acyl group and formation of triacylglycerols (TAGs) from diacylglycerol and acyl-CoA substrates.

As illustrated herein, expression of DGTT enzymes from the photosynthetic green alga *Chlamydomonas reinhardtii* in *Arabidopsis* plants increased TAG content in vegetative tissues by altering the acyl carbon partitioning through a broad range of acyl-CoA substrates. The gain in energy density of the transgenic leaves was evident, for example, from the gain in weight of caterpillar larvae that were allowed to feed on them.

Sequences for diacylglycerol acyltransferase enzymes and nucleic acids encoding such enzymes are available from the National Center for Biotechnology Information (NCBI) database (see, e.g., the website at ncbi.nlm.nih.gov).

For example, a sequence of a protein from *Chlamydomonas reinhardtii* that the inventors have now identified as being a DGTT1 enzyme is available from the NCBI database as accession number XP_001702848.1 (GI: 159489727), and is provided below as SEQ ID NO:1.

```
  1 MQSKRCAELA SGALWPMDRD QMRDRDPWKL RDRAISQAWV
 41 WPLLIGTLLY VQSTTLTIAF LLWHIWKVMA SYFPGARLIK
 81 TADLDPAGRY IFVSHPHGVI AISDWLAFAT EALGFSKLFP
121 GLDLRCATLA SNFWVPGLRE YILSHGMCGV GRDTLARVLT
161 GKPGRAVVLV VGGASEALLA AEGTYDLVLR NRKGFVRLAL
201 QTGASLVPVL SYGETDTFHT YIPPPCSRAA AVMKVLKQVF
241 GFSTPLCWGT GLFGGWGMLA LQVPLTVVVG APIQVDKVSS
281 PTEAEVAALH KTYTEALQKL WDDTVDKYGK GVKRPLAIVQ
```

A nucleic acid encoding the *Chlamydomonas reinhardtii* DGTT1 enzyme with SEQ ID NO:1 is available from the NCBI database with accession number XM_001702796.1 (GI:159489726), and provided below as SEQ ID NO:2.

```
  1 ATGCAAAGTA AGCGTTGTGC AGAGCTGGCC TCTGGGGCTC
 41 TGTGGCCCAT GGACCGCGAC CAGATGCGCG ACCGCGACCC
 81 ATGGAAGCTG CGCGACCGAG CTATAAGCCA AGCATGGGTG
121 TGGCCTCTGC TCATCGGCAC ATTGCTTTAC GTGCAGAGCA
161 CCACGCTCAC AATTGCCTTC CTGCTGTGGC ATATCTGGAA
201 GGTTATGGCC TCTTACTTCC CCGGCGCCCG CCTGATTAAG
241 ACCGCCGACC TGGATCCGGC TGGCCGCTAT ATATTCGTGA
281 GCCACCCGCA CGGCGTCATC GCCATTTCCG ACTGGCTGGC
321 ATTTGCCACA GAGGCGCTGG GCTTCTCCAA ACTGTTCCCA
361 GGCCTGGACC TGCGCTGCGC CACGCTGGCT TCAAACTTCT
401 GGGTGCCTGG TTTGCGTGAG TACATCCTAT CGCACGGCAT
441 GTGCGGCGTG GGGCGAGACA CTCTGGCGCG CGTGCTGACA
481 GGAAAGCCGG GCCGTGCGGT TGTGTTGGTG GTGGGCGGCG
521 CGTCTGAGGC GCTGTTGGCG GCGGAGGGAA CTTATGACCT
561 GGTGCTGCGC AACCGCAAGG GCTTTGTGCG CCTGGCGCTG
601 CAGACCGGCG CCAGTCTGGT GCCGGTGCTG TCGTACGGTG
641 AGACAGACAC CTTCCACACC TACATCCCGC CGCCCTGCAG
681 CCGGGCGCC GCGGTCATGA AGGTGCTGAA GCAGGTGTTT
721 GGCTTCTCCA CGCCCCTGTG CTGGGGCACC GGACTGTTCG
761 GGGGCTGGGG CATGCTAGCG CTGCAGGTGC CGCTCACTGT
801 GGTGGTGGGG GCACCCATAC AGGTGGACAA GGTGTCCAGT
841 CCCACGGAGG CTGAGGTGGC GGCGCTGCAT AAGACCTACA
881 CGGAGGCACT GCAGAAGCTG TGGGATGACA CAGTGGACAA
921 GTACGGCAAG GGTGTCAAGC GGCCGCTGGC CATCGTGCAA
961 TG
```

One example of a sequence of a protein from *Chlamydomonas reinhardtii* that the inventors have now identified as being a DGTT2 enzyme is available from the NCBI database as accession number XP_001694904.1 (GI: 159473565), and provided below as SEQ ID NO:3.

```
  1 MAIDKAPTNV RIWSDGVTEK GKQSIFSSLV AMLTLFIYCG
 41 WMHVLLALVI LSFWYRWALV TVLLLYSTLL LPPKPVLWGP
 61 VCRSWIFQTW REYFKFSYVF DEVLDSKKKY IFAEFPHGVF
121 PMGPLIGATE CQIMFPGFDI FGLAANVVFT VPFWRHFVAW
161 LGSVPATTRD FKRVLKQGSV AVIVGGIAEM YMQSPTKEQI
201 MLKDRKGFVR VAVEEGVDGG IVPVYHFGNS QVLDFGPQAM
241 ASVSRRLRAA LGFLYGVAYL PLPRRRNIYM VCGKPVPVTR
281 TARDDPKFEE VVDATHAAVM AALQEAYDRH KTEYGWADRP
321 LVIS
```

A nucleic acid encoding the *Chlamydomonas reinhardtii* DGTT2 enzyme with SEQ ID NO:3 is available from the NCBI database with accession number XM_001694852.1 (GI:159473564) with the following sequence (SEQ ID NO:4).

```
  1 GGATTTGCAA CTTTCGATAT AGTTACGATT TGCGTGGGAC
 41 CGCCCCATTC ACCTAAGAAG CGGGCCTATT GGCCGCCCCA
 81 CCCGCTGGTA AATTGCGAGT GGGGCGCGCG TCCTAGCTGG
121 ATTTAGGCCA TCTGTTTTTG ATTAAAATTG CAAGTCCGTG
161 TGTCGCGCTC CCCTAAACGT TGGCGCGCCA TAATGGCGAT
201 TGATAAAGCA CCGACAAATG TGCGAATTTG GAGCGATGGC
241 GTCACGGAGA AGGGCAAGCA AAGCATCTTC TCATCGCTGG
281 TGGCTATGTT GACGCTCTTC ATCTACTGTG GCTGGATGCA
321 TGTGCTGCTG GCGCTTGTGA TCCTGTCCTT CTGGTACCGC
361 TGGGCGCTGG TGACGGTGCT GCTGCTGTAC TCCACCCTGC
401 TGCTGCCGCC TAAGCCGGTG CTGTGGGGAC CGGTCTGTCG
441 CTCCTGGATC TTCCAGACCT GGCGGGAGTA CTTCAAGTTC
481 TCTTACGTGT TTGATGAGGT GCTGGACTCG AAGAAGAAGT
521 ACATCTTCGC GGAGTTCCCG CACGGTGTCT TCCCCATGGG
561 CCCACTCATT GGCGCCACAG AATGCCAGAT CATGTTTCCC
601 GGCTTTGACA TCTTCGGGCT GGCGGCGAAT GTGGTGTTCA
641 CGGTCCCCTT CTGGCGGCAT TTCGTGGCGT GGCTGGGCTC
681 CGTGCCGGCC ACCACACGCG ACTTCAAGCG GGTGCTGAAG
721 CAAGGAAGCG TGGCGGTCAT CGTGGGAGGC ATCGCAGAGA
761 TGTACATGCA GAGCCCCACG AAGGAGCAGA TCATGTTGAA
801 GGACCGCAAG GGCTTTGTTC GTGTGGCGGT GGAGGAGGGC
841 GTGGATGGCG GCATCGTGCC GGTCTACCAC TTTGGCAACT
881 CTCAGGTGCT GGACTTCGGC CCCCAGGCCA TGGCCAGTGT
921 GCACCGCCCG CTGCGTGCGG CCCTGGGCTT CCTGTACGGA
```

```
 961 GTGGCCTACC TGCCCCTGCC CAGGCGCCGC AACATTTACA
1001 TGGTGTGCGG CAAGCCCGTT CCCGTCACGC GCACCGCCCG
1041 CGACGACCCC AAGTTTGAGG AGGTGGTTGA CGCCACTCAC
1081 GCCGCTGTGA TGGCGGCCCT GCAGGAGGCC TACGACCGCC
1121 ACAAGACCGA GTACGGCTGG GCCGACCGAC CGCTGGTCAT
1161 CAAGGAAGCG GGCGGCGGTT GAATGGCTGG GATCTGTTGC
1201 TGGTGCTGAT TTGTAAGTGT GGCTTGGCGC AATACAGGCG
1241 GCGGCAGCAG TGGCGGCGGC AGCACCCAGG GTAGCAGGAG
1281 CTGCGCAGCC GAAAGTGAAG GCGCTGGGAG AGTTGTGCGT
1321 GC
```

One example of a sequence of a protein from *Chlamydomonas reinhardtii* that the inventors have now identified as being a DGTT3 enzyme is available from the NCBI database as accession number XP_001691447.1 (GI: 159466500), and provided below as SEQ ID NO:5.

```
  1 MAGGKSNGTG AADAHVRTSH LTLKAGEDPP PNVRIYSDGI
 41 KPDARQNLLV QILAGITMSI YVGFMNYFML LVVLSYWSRI
 81 CRYVVLALLG TLALPCKPVL WPAFNKLWIF KTWRHYFHYS
121 FLIEEPLDPN KRYIFVEFPH GAFPIGPIVA GTLMQTLFPH
161 MMIYSVAASV VFYIPFWRHF ITWIGSVPAT PGNFKRLLKK
201 GSVAVVVGGI AEMYMGNKKK ERIKLVGRRG FARIALEEQV
241 DGIVCVYYFG QSQVLDFGPS WLADFSRRMR TSFGYLTGWM
281 GLPVPRPIPI YMVNGKPIPV PKVARDSPEF DKEVDKLLDA
321 TITELGEMYN RHRGEYGWGD RPLSIE
```

A nucleic acid encoding the *Chlamydomonas reinhardtii* DGTT3 enzyme with SEQ ID NO:5 is available from the NCBI database with accession number XM_001691395.1 GI:159466499) with the following sequence (SEQ ID NO:6).

```
   1 GCTTACCAAT ACTGTTTGCA ATCGTATACG TGCGGCGCAG
  41 CGTGCGGGAT ACGTCCCATA ACACCACTG CATAATCCGC
  81 GTTAGCCAAC GAGCTTCCCC AGCGCCCCCG CGCGTGCACT
 121 GGCGGCTTTC GGCACTAGCC AAGCCTTTAG GCGTAGACTG
 161 GGCGCCTGAG GCGCGGACAC ACAGCCGCAC CGAGACGTTG
 201 AGCGTTTCAT CCGAGCTCAC TCACGCGCAT CGCCGGCGGG
 241 ACACTGCGCA CGGAGCCCGC GCGCGGACAC ACCTGGGCCC
 281 CTGCACGAAG GGCCGCCGCG AGACGGAAGC AGATGGCAGG
 321 TGGAAAGTCA AACGGCACGG GCGCGGCGGA CGCGCACGTG
 361 CGTACCTCGC ACTTGACCCT GAAAGCTGGG GAGGACCCGC
 401 CCCCGAATGT TCGCATCTAC AGTGACGGCA TCAAGCCGGA
 441 CGCGCGGCAG AACCTGCTTG TTCAGATCCT GGCCGGCATC
 481 ACGATGTCGA TTTATGTAGG CTTCATGAAC TATTTCATGC
 521 TGCTGGTGGT GCTCTCCTAC TGGAGCCGCA TCTGCCGCTA
 561 TGTGGTCCTG GCGCTGCTAG GCACACTGGC GCTGCCCTGC
 601 AAGCCCGTGC TGTGGCCTGC CTTCAACAAG CTGTGGATCT
 641 TCAAGACCTG GCGTCACTAC TTCCACTACA GTTTCCTGAT
 681 TGAGGAGCCG CTTGACCCCA ACAAGCGCTA CATCTTTGTC
 721 GAGGACCCGC ACGGCGCGTT CCCCATTGGT CCCATCGTGG
 761 CGGGCACGCT CATGCAGACT CTGTTCCCGC ACATGATGAT
 801 CTACAGCGTG GCCGCCTCCG TCGTGTTCTA CATCCCCTTC
 841 TGGCGCCATT TCATCACGTG GATCGGCTCG GTGCCCGCAA
 881 CGCCCGGCAA CTTCAAGCGG CTGCTGAAGA AGGGCAGTGT
 921 GGCGGTGGTG GTGGGCGGCA TTGCCGAGAT GTACATGGGC
 961 AACAAGAAGA AGGAGCGCAT TAAGCTAGTG GGCCGCCGCG
1001 GCTTCGCACG CATCGCGCTG GAGGAGCAGG TGGACGGCAT
1041 TGTGTGCGTG TACTACTTCG GTCAGAGCCA AGTGCTGGAC
1081 TTCGGGCCCT CCTGGCTGGC GGACTTTAGC CGCCGCATGC
1121 GCACCAGCTT CGGCTACCTC ACGGGATGGA TGGGGCTGCC
1161 GGTGCCGCGG CCCATCCCCA TCTACATGGT GAATGGGAAG
1201 CCCATCCCGG TGCCCAAGGT GGCTCGTGAC TCGCCCGAGT
1241 TCGACAAGGA GGTGGATAAG CTGCTTGACG CCACCATCAC
1281 GGAGCTGGGC GAGATGTACA ACAGGCACAG AGGCGAGTAC
1321 GGCTGGGGCG ACCGCCCGCT GTCCATCGAG TAGATGCCCA
1361 ACAAGTGGAT TGGCACAGTG GTGCCCTTGA AATGGCATGG
1401 CCAGAGTGAA AGCGGGATGG ATCGTTGGAG ATGGTTATGG
1441 AGGGGAGGAA GGAATATCTT GAAAAGGCCA CGCGGATGGG
1481 TTCGTGAGGC ATGCAGGGCC TTTCGGGTTG GATGGGGGTC
1521 GCACTAGTCG CACGTGCCGC GTGGGCACGT GTGTGCCGTA
1561 AACCTTTTAT GGTATGGTGT GTCAAGACTA GTCTAGACGT
1601 ACCGATGGCT ATATGGTAGC TCAGCTATGC GAAAAGCTGC
1641 GAAACGGGCT GGCATTGCCT TTGGGTGAAC GTGCAAGTGT
1681 TGTGTTTAGA TGCAAGGCAG GTGGATGCAG TTGTAGGTGT
1721 AGCAGACCTT TACATCAGCA CAGTTGGCTA GATAGGTCGC
1761 GTCAGCCAAG GAGGGAGCTC TGCGTTTGAT TGGGTTGATG
1801 CTGCCAGCAG GCGGCATTAA AATGGACGTG GCAAGGGAGC
1841 AATAGAGCCT TTGAAAGAAT GCCATATCCT GAAGACACAC
1881 GTGCATGACG CAAGGGTCCC GTTGCTGAGC TCCTGACTTG
1921 ATCATCCCTT GGATGCTGTC ACGCAATGTG CTTCAA
```

One example of a sequence of a protein from *Chlamydomonas reinhardtii* that the inventors have now identified as being a DGTT4 enzyme is provided below as SEQ ID NO:7.

```
  1 MPLAKLRNVV LEYAAIAIYV SAIYTSVVLL PSALALFYLF

41 GATSPSAWLL LAAFLALTFT PLQLTTGALS ERFVQFSVAR

81 AAAYFPTRVV VTDPEAFRTD RGYLFGFCPH SALPIALPIA

121 FATTSPLLPK ELRGRTHGLA SSVCFSAPIV RQLYWWLGVR

161 PATRQSISGL LRARKVAVLV PGGVQEVLNM EHGKEVAYLS

201 SRTGFVRLAV QHGAPLVPVW AFGQTRAYSW FRPGPPLVPT

241 WLVERISRAA GAVPIGMFGQ YGTPMPHREP LTIVVGRPIP

281 VPELAPGQLE PEPEVLAALL KRFTDDLQAL YDKHKAQFGK

321 GEELVIM
```

Although the DGTT enzymes can be any of the DGTT enzymes described herein, in some embodiments the DGTT enzymes can be DGTT2 or DGTT3 enzymes.

Related Nucleic Acids or Polypeptides

The nucleic acids, polypeptides, plants, and seeds can also have sequences related to any of the sequences described herein. For example, related nucleic acids can be isolated and identified by mutation of any of the SEQ ID NO:1-7 sequences and/or by hybridization to DNA and/or RNA isolated from other plant species using any of SEQ ID NO:2, 4, or 6 nucleic acids (or portions thereof) as probes.

In some embodiments, the related nucleic acids and proteins are identified by hybridization of any of SEQ ID NO: 2, 4, or 6 nucleic acids (or portions thereof) as probes under stringent hybridization conditions. The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides), and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal Biochem 138: 267-84 (1984)):

$$T_m = 81.5° C. + 16.6(\log M) + 0.41(\% \ GC) - 0.61(\% \ \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of SEQ ID NO:2, 4, or 6 nucleic acids.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, Laboratory Techniques in Biochemistry and Molecular Biology—Hybridization with Nucleic Acid Probes, part 1, chapter 2, "Overview of principles of hybridization and the strategy of nucleic acid probe assays," Elsevier, N.Y. (1993); and in Current Protocols in Molecular Biology, chapter 2, Ausubel, et al., eds, Greene Publishing and Wiley-Interscience, New York (1995).

For example, high stringency can be defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, the stringency of hybridization is actually determined by the wash conditions. Thus, wash conditions in 0.1×SSC, 0.1% SDS at 65° C. are a sufficient definition of stringent hybridization conditions.

Such selective hybridization substantially excludes non-target nucleic acids. Selectively hybridizing sequences typically have about at least 40% sequence identity, at least about 50% sequence identity, at least 55% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity or complementarity with any of the SEQ ID NO:2, 4, or 6 nucleic acids.

The nucleic acids of the invention include those with about 500 of the same nucleotides as any of SEQ ID NO:2, 4, or 6 nucleic acids, or about 600 of the same nucleotides, or about 700 of the same nucleotides, or about 800 of the same nucleotides, or about 900 of the same nucleotides, or about 1000 of the same nucleotides, or about 1100 of the same nucleotides, or about 1200 of the same nucleotides, or about 1300 of the same nucleotides, or about 500-1325 of the same nucleotides. The identical nucleotides or amino acids can be distributed throughout the nucleic acid, and need not be contiguous.

The polypeptides of the invention include those with about 50 of the same amino acids as any of SEQ ID NO:1, 3, 5, or 7 polypeptides, or about 60 of the same amino acids, or about 70 of the same amino acids, or about 80 of the same amino acids, or about 90 of the same amino acids, or about 100 of the same amino acids, or about 110 of the same amino acids, or about 120 of the same amino acids, or about 130 of the same amino acids, or about 140 of the same amino acids, or about 150 of the same amino acids, or about 50-80 of the same amino acids, or about 150-325 of the same amino acids as any of any of SEQ ID NO:1, 3, 5, or 7 polypeptides. The identical amino acids can be distributed throughout the nucleic acid, and need not be contiguous.

The polypeptides have about at least 40% sequence identity, at least about 50% sequence identity, at least 50% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity with any of the SEQ ID NO:1, 3, 5, or 7 polypeptides.

Note that if a value of a variable that is necessarily an integer, e.g., the number of nucleotides or amino acids in a nucleic acid or protein, is described as a range, e.g., is 90-99% sequence identity, what is meant is that the value can be any integer between 90 and 99 inclusive, i.e., 90-99% sequence identity means any of 90, 91, 92, 93, 94, 95, 96, 97, 98 or 99% sequence identity.

For example, the DGTT enzymes can be DGTT2 or DGTT3 enzymes, with DGTT2 sequences SEQ ID NO:3 and 4 (or at least 40% sequence identity therewith), or with DGTT3 sequences SEQ ID NO: 5 and 6 (or at least 40% sequence identity therewith).

Modified Plants Having Diacylglycerol Acyltransferase Type Two (DGTT)

In order to engineer plants with desired quantities of triacylglycerols, one of skill in the art can introduce diacylglycerol acyltransferase type two (DGTT) enzymes or nucleic acids encoding such enzymes into the plants. Any of the diacylglycerol acyltransferase type two (DGTT) nucleic acids, and related nucleic acid sequences, described herein can be incorporated into the expression cassettes, plants and seeds described herein.

In some embodiments, one of skill in the art could inject diacylglycerol acyltransferase type two (DGTT) enzymes or nucleic acids encoding such diacylglycerol acyltransferase type two (DGTT) enzymes into young plants, or into selected regions of plants. Alternatively, one of skill in the art can generate genetically-modified plants that contain nucleic acids encoding diacylglycerol acyltransferase type two (DGTT) within their somatic and/or germ cells. For example, any of the diacylglycerol acyltransferase type two (DGTT) nucleic acids described herein can be operably linked to a selected promoter (e.g., a heterologous promoter), to generate an expression cassette that can be used to generate transgenic plants and/or seeds. Examples of diacylglycerol acyltransferase type two (DGTT) coding regions that can be used in such expression cassettes include any of the following SEQ ID NOs: 1, 3, 5, 7, or any combination thereof. The expression cassettes can be introduced into plants to increase the triacylglycerols content of the plant's tissues.

To facilitate expression of a coding region of interest, an expression cassette can be made that encodes any of the diacylglycerol acyltransferase type two (DGTT) or related enzymes described herein. The genetic modifications involved can be accomplished by procedures available in the art. For example, one of skill in the art can prepare an expression cassette or expression vector that can express one or more encoded enzymes. In general, a nucleic acid segment encoding a diacylglycerol acyltransferase type two (DGTT) enzyme can be operably linked to a promoter, for example, by inserting the promoter nucleic acid segment upstream of a selected enzyme coding region.

Plant cells can be transformed by the expression cassettes or expression vector, and whole plants (and their seeds) can be generated from the plant cells that were successfully transformed with the diacylglycerol acyltransferase type two (DGTT) nucleic acids. Some procedures for making such genetically modified plants and their seeds are described in more detail below.

Heterologous Promoters: The diacylglycerol acyltransferase type two (DGTT) (or related) nucleic acids can be operably linked to a promoter, such as a heterologous promoter, which provides for expression of mRNA encoding the diacylglycerol acyltransferase type two (DGTT) enzymes. The heterologous promoter employed is typically a promoter functional in plants and/or seeds, and can be a promoter functional during plant growth and development. The heterologous promoter is a promoter that is not operably linked to diacylglycerol acyltransferase type two (DGTT) nucleic acids in nature. A diacylglycerol acyltransferase type two (DGTT) nucleic acid is operably linked to the promoter when the diacylglycerol acyltransferase type two (DGTT) nucleic acid is located downstream from the promoter, so that the promoter is configured to express the diacylglycerol acyltransferase type two (DGTT) enzymes.

Promoters regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs that is a DNA different from the native or homologous DNA generally associated with the promoter.

Promoter sequences can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, expression can be stimulated from an inducible promoter by factors such as alcohol, acetaldehyde, antibiotics (e.g., tetracycline), steroids, metals and other compounds. An environmentally inducible promoter can induce expression of a gene in response to environmental stimuli such as drought, cold, heat, longer exposure to light, or shorter exposure to light. A bacterial promoter such as the $P_{tac}$ promoter can be induced to vary levels of gene expression depending on the level of isothiopropylgalactoside added to the transformed cells. Steroid inducible promoters have also been employed in plants. Dexamethasone-inducible promoters are activated by introduction of dexamethasone to a cell, tissue, cell culture, or tissue culture. The alc promoter system from the filamentous fungi *Aspergillus nidulans* can be induced by alcohol (e.g., ethanol) or acetaldehyde (see, e.g., Schaarschmidt et al., Plant & Cell Physiol 45(11): 1566-77 (2004). The nopaline synthase (nos) promoter is inducible by hydrogen peroxide and/or methyl jasmonate (see, e.g., Sai & An, Plant Physiol. 109(4): 1191-97 (1995)).

Promoters can also provide for tissue specific or developmental regulation. In some embodiments, an isolated promoter sequence that is a strong promoter for heterologous DNAs is advantageous because it provides for a sufficient level of gene expression for easy detection and selection of transformed cells and provides for a high level of gene expression when desired.

Expression cassettes encoding a diacylglycerol acyltransferase type two (DGTT) enzyme can include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), Adh1 (Walker et al., *Proc. Natl. Acad. Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology*. 12:579-589 (1989)), GAL4/UAS (Brand & Perrimon, Development 118: 401-15 (1993); and/or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J*. 3:1671 (1971)) and the actin promoter from rice (McElroy et al., *The Plant Cell*. 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are available to those of skill in the art.

Alternatively, novel tissue specific promoter sequences may be employed for the expression of the diacylglycerol acyltransferase type two (DGTT) enzyme(s). cDNA clones from a particular tissue can be isolated and those clones that are expressed specifically in a tissue of interest are identified, for example, using Northern blotting, quantitative PCR and other available methods. In some embodiments, the gene isolated is not present in a high copy number, but is relatively abundant in specific tissues. The promoter and control elements of corresponding genomic clones can then be identified, isolated and utilized using techniques well known to those of skill in the art.

A diacylglycerol acyltransferase type two (DGTT) nucleic acid can be combined with a selected promoter by standard methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The diacylglycerol acyltransferase type two (DGTT) nucleic acids can be subcloned downstream from the promoter using restriction enzymes and positioned to ensure that the diacylglycerol acyltransferase type two (DGTT) DNA is inserted in proper orientation with respect to the promoter so that the DNA can be expressed. The diacylglycerol acyltransferase type two (DGTT) nucleic acid operably linked to a promoter can form an expression cassette, which can be subcloned into a plasmid or other vector (e.g., an expression vector).

In some embodiments, a cDNA encoding a protein with at least 60% sequence identity to any of SEQ ID NO:1, 3, 5, or 7 is isolated from a selected plant species, and operably linked to a heterologous promoter. The a cDNA encoding a protein can, for example, be a cDNA from an oleaginous plant, an *Arabidopsis* plant, corn, sugar beets, soybean, sugar cane, potato, grasses (e.g., miscanthus, switchgrass, and the like), rice, Diatoms, *Nannochloropsis*, a fresh water algal species, a marine algal species, a beet species, a grape species, an *Arabidopsis* species, a *Brassica* species, a *Brassica napus* plant, an algae species, an oilseed rape species, a sunflower, a soybean species, a flax species, an olive species, an alfalfa species, an oat species, a poplar, an aspen, a willow, and similar plant species. Species of algae from which the cDNA can be obtained from *Archaeplastidia, Rhizaria, Excavate, Chromista, Alveolata, Hetrokonts, Cryptophyta, Dinoflagellates, Haptophyta*, and any combination thereof.

In other embodiments, cDNA from other species that encode a diacylglycerol acyltransferase type two (DGTT) enzyme is isolated from selected plant tissues, or a nucleic acid encoding a mutant or modified diacylglycerol acyltransferase type two (DGTT) enzyme is prepared by available methods or as described herein. For example, the nucleic acid encoding a mutant or modified diacylglycerol acyltransferase type two (DGTT) protein can be any nucleic acid with a coding region that hybridizes to SEQ ID NO:1, 3, 5, or 7 that can promote expression of a diacylglycerol acyltransferase type two (DGTT) enzyme. Using restriction endonucleases, the entire coding sequence for the diacylglycerol acyltransferase type two (DGTT) can be subcloned downstream of the promoter in a 5' to 3' sense orientation.

Targeting Sequences: Additionally, expression cassettes can be constructed and employed to target the diacylglycerol acyltransferase type two (DGTT) to intracellular compartments within plant cells, or to target the diacylglycerol acyltransferase type two (DGTT) for extracellular secretion.

In general, the diacylglycerol acyltransferase type two (DGTT) operate intracellularly. Therefore, the diacylglycerol acyltransferase type two (DGTT) is preferably not directed to the extracellular environment. However, there may be instances where is it desirable to secrete or sequester the diacylglycerol acyltransferase type two (DGTT) within organelles or storage vesicles (e.g., to facilitate isolation and/or purification of the diacylglycerol acyltransferase type two (DGTT) enzyme. Therefore, the invention contemplates targeting the diacylglycerol acyltransferase type two (DGTT) enzymes to various intracellular and extracellular locations.

A nuclear localization signal or sequence is an amino acid sequences that 'tags' a protein for import into the cell nucleus by nuclear transport. A localization signal or sequence can be operably linked to the diacylglycerol acyltransferase type two (DGTT) sequence. Transit peptides act by facilitating the transport of proteins through intracellular membranes, e.g., vacuole, vesicle, plastid and mitochondrial membranes, whereas signal peptides direct proteins through the extracellular membrane. Polypeptides of interest can be operably linked to nuclear localization signals/sequences, to transit peptides or to signal peptides.

Targeting to selected intracellular regions can generally be achieved by joining a DNA sequence encoding a nuclear localization sequence, or a transit peptide or a signal peptide sequence to the coding sequence of the diacylglycerol acyltransferase type two (DGTT) or the related polypeptide of interest. The resultant nuclear localization sequence (or transit, or signal, peptide) will transport the diacylglycerol acyltransferase type two (DGTT) enzyme to a particular intracellular (or extracellular) destination. Such sequences (nuclear localization sequences, transit peptides or signal peptides) may be post-translationally removed by cellular enzymes. By facilitating transport of the protein into compartments inside or outside the cell, these sequences can increase the accumulation of a particular gene product in a particular location.

3' Sequences: The expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research*. 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology*. 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the diacylglycerol acyltransferase type two (DGTT) nucleic acids by standard methods.

Selectable and Screenable Marker Sequences: In order to improve identification of transformants, a selectable or screenable marker gene can be employed with the expressible diacylglycerol acyltransferase type two (DGTT) nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for the marker by chemical means, i.e., through the use of a selective agent (e.g., a herbicide, antibiotic, or the like), or whether marker is simply a trait that one can identify through observation or testing, i.e., by 'screening' (e.g., the R-locus trait). Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of marker proteins suitable for modification in this manner include extensin or hydroxyproline rich glycoprotein (HPRG). For example, the maize HPRG (Stiefel et al., *The Plant Cell*. 2:785-793 (1990)) is well characterized in terms of molecular biology, expression, and protein structure and therefore can readily be employed. However, any one of a variety of extensins and/or glycine-rich wall proteins (Keller et al., *EMBO J*. 8:1309-1314 (1989)) could be modified by the addition of an antigenic site to create a screenable marker.

Numerous other possible selectable and/or screenable marker genes will be apparent to those of skill in the art in addition to the one set forth herein. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with expression cassettes include, but are not limited to, a neo gene (Potrykus et al., Mol. Gen. Genet. 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology*. 6:915-922 (1988)) thus conferring glyphosate resistance; a nitrilase gene such as bxn from *Klebsiella ozaenae* which confers resistance to bromoxynil (Stalker et al., *Science*. 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

Another selectable marker gene capable of being used in for selection of transformants is the gene that encodes the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., *In: Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., Bio/technology 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the Cl and R alleles are introduced together.

The R gene regulatory regions can be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (e.g., antibiotic or herbicide resistance), unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to express the diacylglycerol acyltransferase type two (DGTT) of interest. For example, an expression cassette encoding a diacylglycerol acyltransferase type two (DGTT) can be screened to ascertain whether it can promote expression of a diacylglycerol acyltransferase type two enzyme by methods described herein or other available methods for detecting triacylglycerols. An expression cassette encoding other enzymes of interest can be screened to ascertain whether it can promote expression of the enzyme, for example, by immunological detection of the enzyme of interest, by detection of the activity of the enzyme, by hybridization or PCR detection of transcripts encoding the enzyme, or by other procedures available to those of skill in the art.

DNA Delivery of the DNA Molecules into Host Cells: The diacylglycerol acyltransferase type two (DGTT) nucleic acids can be introduced into host cells by a variety of methods. For example, a preselected cDNA encoding the selected diacylglycerol acyltransferase type two (DGTT) can be introduced into a recipient cell to create a transformed cell by available procedures. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells can be regenerated into transgenic plants, through the application of the techniques disclosed herein.

Another aspect of the invention is an isolated plant or plant cell that has at least one of the diacylglycerol acyltransferase type two (DGTT) nucleic acids, or related nucleic acids, introduced into the cell. The plant or plant cell can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons.

Suitable examples of plant species for the plant cells, plants and seeds include an oleaginous plant, an *Arabidopsis* plant, corn, sugar beets, soybean, sugar cane, potato, grasses (e.g., *miscanthus*, switchgrass, and the like), rice, a beet species, a grape species, an *Arabidopsis* species, a *Brassica* species, a *Brassica napus* plant, an algae species, an oilseed rape species, a sunflower, a soybean species, a flax species, an olive species, an alfalfa species, an oat species, a wheat species, a poplar, an aspen, a willow, and similar plant species. In some embodiments, the plant or cell is a monocotyledon plant or cell. For example, the plant or cell can be a maize plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; 5,472,869). For example, embryogenic cell lines derived from immature *Zea mays* embryos can be transformed by accelerated particle treatment as described by Gordon-Kamm et al. (*The Plant Cell*. 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but eliminate functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the diacylglycerol acyltransferase type two (DGTT) nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. For example, non-embryogenic Black Mexican Sweet maize cells can be bombarded with intact cells of the bacteria *E. coli* or *Agrobacterium tumefaciens* containing plasmids with either the β-glucuronidase or bar gene engineered for expression in maize. Bacteria can be inactivated by ethanol dehydration prior to bombardment. A low level of transient expression of the β-glucuronidase gene may be observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. The particles may increase the level of DNA delivery but may not be, in and of themselves, necessary to introduce DNA into plant cells.

An advantage of microprojectile bombardment, in addition to it being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of such techniques one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of a diacylglycerol acyltransferase type two (DGTT) nucleic acid into recipient cells by any of the methods discussed above, the transformed cells can be identified for further culturing and plant regeneration. As mentioned above, in order to improve the ability to identify transformants, one may employ a selectable or screenable marker gene in addition to the diacylglycerol acyltransferase type two (DGTT) nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the Cl and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soil-less plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the diacylglycerol acyltransferase type two (DGTT) nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced diacylglycerol acyltransferase type two (DGTT) nucleic acids, the plant is self-pollinated at least once in order to produce a homozygous backcross converted inbred containing the diacylglycerol acyltransferase type two (DGTT) nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the diacylglycerol acyltransferase type two (DGTT) nucleic acids (or the encoded enzyme). Transgenic plant and/or seed tissue can be analyzed for diacylglycerol acyltransferase type two (DGTT) expression using standard methods such as SDS polyacrylamide gel electrophoresis, liquid chromatography (e.g., HPLC) or other means of detecting a product of the diacylglycerol acyltransferase type two (DGTT) activity (e.g., increased triacylglycerols or heightened expression of a the diacylglycerol acyltransferase type two (DGTT) enzyme).

Once a transgenic seed expressing the diacylglycerol acyltransferase type two (DGTT) is identified, the seed can be used to develop true breeding plants. The true breeding plants are used to develop a line of plants that express the diacylglycerol acyltransferase type two (DGTT) or related enzymes described herein, while still maintaining other desirable functional agronomic traits. Adding the trait of increased diacylglycerol acyltransferase type two (DGTT) expression to the plant can be accomplished by back-crossing with this trait with plants that do not exhibit this trait and by studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of expression of the diacylglycerol acyltransferase type two (DGTT) in the plant. The resulting progeny are then crossed back to the parent that expresses the trait. The progeny from this cross will also segregate so that some of the progeny carry the trait and some do not. This back-crossing is repeated until an inbred line with the desirable functional agronomic traits, and with expression of the desired trait within the plant. Such expression of the increased expression of the diacylglycerol acyltransferase type two (DGTT) in plant can be expressed in a dominant fashion.

Subsequent to back-crossing, the new transgenic plants can be evaluated for expression of the diacylglycerol acyltransferase type two (DGTT) enzyme or mRNA. For example, when the diacylglycerol acyltransferase type two (DGTT) is expressed the weight percent of triacylglycerols within the plant or within selected tissues of the plant is increased. Detection of increased triacylglycerols can be done, for example, by staining plant tissues for triacylglycerols or by observing whether the plant tissue oil content is increased relative to a plant that does not contain the exogenously added diacylglycerol acyltransferase type two (DGTT). The new transgenic plants can also be evaluated for a battery of functional agronomic characteristics such as lodging, kernel hardness, yield, resistance to disease and insect pests, drought resistance, and/or herbicide resistance.

Plants that may be improved by these methods (incorporation of nucleic acids encoding the diacylglycerol acyltransferase type two (DGTT) enzymes) include but are not limited to fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and *eucalyptus*), oil and/or starch plants (canola, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues: To confirm the presence of the diacylglycerol acyltransferase type two (DGTT) nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced diacylglycerol acyltransferase type two (DGTT) nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the diacylglycerol acyltransferase type two (DGTT) nucleic acid in question, they do not provide information as to whether the preselected DNA segment is being expressed. Expression may be evaluated by specifically identifying the protein products of the introduced diacylglycerol acyltransferase type two (DGTT) nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the diacylglycerol acyltransferase type two (DGTT) enzyme such as evaluation by amino acid sequencing following purification. The Examples of this application also provide assay procedures for detecting and quantifying the diacylglycerol acyltransferase type two (DGTT) or its enzyme activities. Other procedures may be additionally used.

The expression of a gene product can also be determined by evaluating the phenotypic results of its expression. These assays also may take many forms including but not limited to analyzing changes in the chemical composition, morphology, or physiological properties of the plant.

Biofuel Manufacture

Lipids can be isolated from plants or plant tissues transformed by nucleic acids or nucleic acid constructs encoding diacylglycerol acyltransferase type two (DGTT) enzymes. Such lipids are useful for manufacture of biofuels.

Manufacture of biofuel can involve one or more steps such as tissue crushing, tissue sonication, tissue fractionation, cellular lysis, filtering, water removal, solvent extraction, removal of volatile components, titration to ascertain lipid (e.g, fatty acid) content, transesterification (e.g., conversion of acid moieties to alkyl esters), separation of desired lipid components from undesired lipid components, lipid fractionation, and combinations of such steps. Such steps can be performed in the order listed, or in any other order. For example, water and/or volatiles can be removed before and/or after transesterification.

A filtering step can involve particle removal. This process can include warming the lipid extract to maintain the lipid in liquid form and/or to reduce its viscosity. After warming up the liquid, it can be filtered. The filter can have pore sizes smaller than the particles to be removed but sufficient to pass the lipid(s).

Water can be removed by heating the lipid(s) and/or by use of one or more desiccants. For example, water can be removed by boiling the lipid(s) at 100° C.

Titration can be used to assess the amount of acid to be converted to ester. This process can involve dissolving the lipids in an alkanol solution containing an indicator. This solution can then titrated with alkali (e.g., KOH or NAOH) until the indicator shows that the pH of the solution is approximately neutral.

Transesterification can involve mixing the lipid(s) with sodium alkoxide (e.g., sodium methoxide). To generate sodium alkoxide (e.g., sodium methoxide), the selected alkanol (e.g., methanol) is mixed with sodium hydroxide to produce sodium alkoxide (e.g., sodium methoxide). In some instances, the quantity of alkanol used can be 20 percent of the lipid volume. The transesterification mixture can be heated and mixed to facilitate reaction. For example, the mixture can be heated to about 40 to 60° C., or about 45 to 55° C., with mixing.

The lipids can then be cooled, and separated if desired. After the cooling process, the biofuel is generally floating at the top while a heavier glycerin layer can be found at the bottom. The glycerin can be easily separated by allowing it to drain out from the bottom. The process can generate pure biofuel which can be used for various purposes. For example, pure purified lipids can be used as a fuel. Alternatively, the lipids can be mixed with petroleum (e.g., diesel, or heating oil), alcohol, or other fuel product and then used as a fuel (e.g., B20 fuel).

Definitions

As used herein, the terms "crop" and "crop plant" are used herein its broadest sense. The term includes, but is not limited to, any species of plant or alga edible by humans or used as a feed for animals or fish or marine animals, or consumed by humans, or used by humans, or viewed by humans (flowers) or any plant or alga used in industry or commerce or education, such as vegetable crop plants, fruit crop plants, fodder crop plants, fiber crop plants, wood-generating plants, and turf grass plants.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "expression" when used in reference to a nucleic acid sequence, such as a coding region or protein, refers to the process of converting genetic information encoded in a coding region into RNA (e.g., mRNA, rRNA, tRNA, or snRNA) through "transcription" of a gene or expression cassette (i.e., via the enzymatic action of an RNA polymerase), and into protein where applicable (as when a coding region encodes a protein), through "translation" of mRNA. Gene expression can be regulated at many stages in the process. "Up-regulation" or "activation" or "increased expression" refers to regulation that increases the production of gene expression products (i.e., RNA or protein), while "down-regulation" or "repression" or "decreased expression" refers to regulation that decreases production. Molecules (e.g., transcription factors) that are involved in up-regulation or down-regulation can also be called "activators" and "repressors," respectively.

As used herein, the term "heterologous" when used in reference to a gene, promoter, or nucleic acid refers to a gene, promoter, or nucleic acid that has been manipulated in some way. For example, a heterologous nucleic acid or a heterologous promoter includes a nucleic acid or promoter from one species that is introduced into another species. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous coding regions can be distinguished from endogenous plant coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, the terms "leaf" and "leaves" refer to a usually flat, green structure of a plant where photosynthesis and transpiration take place and attached to a stem or branch.

As used herein, a "native" nucleic acid or polypeptide means a DNA, RNA or amino acid sequence or segment that has not been manipulated in vitro, i.e., has not been isolated, purified, and/or amplified.

As used herein, the term "naturally linked" or "naturally located" when used in reference to the relative positions of nucleic acid sequences means that the nucleic acid sequences exist in nature in those positions.

As used herein, the terms "operably linked" or "in operable combination" or "in operable order" refers to the linkage of nucleic acids in such a manner that a nucleic acid molecule capable of directing the transcription of a given coding region and/or the synthesis of a desired protein molecule is produced. As used herein, the term also refers to the linkage of amino acid sequences in such a manner so that a functional protein is produced.

As used herein, the term "plant" is used in its broadest sense. It includes, but is not limited to, any species of grass (e.g. turf grass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, stomata, a seed, a tiller, a sprig, a stolon, a plug, a rhizome, a shoot, a stem, a leaf, a flower petal, a fruit, etc.

As used herein, the terms "protein," "polypeptide," "peptide," "encoded product," "amino acid sequence," are used interchangeably to refer to compounds comprising amino acids joined via peptide bonds and. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" and "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence can include post-translational modifications of the encoded and deduced amino acid sequence.

As used herein, "seed" refers to a ripened ovule, consisting of the embryo and a casing.

As used herein, "stem" refers to a main ascending axis of a plant.

As used herein, the term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like. Methods of transfection are described herein.

As used herein, the term "transgene" refers to a foreign gene (e.g., an expression cassette) that is placed into an organism by the process of transfection.

As used herein, the term "vector" refers to nucleic acid molecules that transfer DNA segment(s). Transfer can be into a cell, cell-to-cell, etc.

As used herein, the term "wild-type" when made in reference to a nucleic acid or gene refers to a functional nucleic acid or gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples illustrate how aspects of the invention have been developed and can be made and used.

EXAMPLE 1

Materials and Methods

This Example describes some of the materials and methods used in the development of the invention.

Phylogenetic Analysis The protein sequences for the *Chlamydomonas* DGTT1-5 genes were retrieved by sequence comparison with *Arabidopsis* DGAT2 using BLAST (Altschul et al., Nucleic Acids Res 25, 3389-3402 (1997)). Sequences of DGTT1-5 and other DGAT2 proteins were aligned using the ClustalW software in MEGA5 (Tamura et al., Mol Biol Evol 28, 2731-2739 (2011)). The alignment was then used to construct a phylogenetic tree using the Neighbor-Joining method in MEGA5, with the tree being tested by bootstrapping with 1000 replicates.

Plasmid Construction

*Chlamydomonas* strain dw15.1 (cw15, nitl, mt+), provided by Arthur Grossman, was grown under continuous light (~80 μm/m$^2$/s) and at 22° C. in liquid TAP media (Harris, E. H., THE CHLAMYDOMONAS SOURCE BOOK (New York: Academic Press, 1989) until mid-log phase, and then pelleted. Total RNA was extracted from the cells using Qiagen RNeasy Plant Mini kit (see website at qiagen.com). cDNA was synthesized with SuperScriptlll from Invitrogen (see website at invitrogen.com) and oligo-dT primers. The cDNA so manufactured was used as a template for PCR. The primers used are listed in Table 1. The amplified regions were digested with HindIII and SphI, for DGTT2 and DGTT4, and HindIII and XhoI, for DGTT3 and DGTT5. The amplified cDNA segments were then sub-cloned into the Invitrogen pYES2 vector to form pYES2-DGTT2-5 for expression in yeast.

DGTT2 cDNA was amplified from pYES2-DGTT2 by PCR using gene specific primers (see Table 1). A fragment of 975 by containing the complete open reading frame was digested with BamHI and EcoRI. This fragment was then placed between the CaMV 35S promoter and OCS terminator of vector p9-35S-OCS (DNA Cloning Service, Hamburg, Germany) to form 35S:DGTT2.

TABLE 1

Primers

| Name | Gene ID | | 5' Sequence 3' | SEQ ID NO |
|---|---|---|---|---|
| DGTT2-his | | F | GCGCAAGCTTAGCATGGGTCATCATCACCATCACCA TGCGATTGATAAAGCA | 8 |
| | | R | GCGCGCGCATGCTCAGCTGATGACCAGCGG | 9 |
| DGTT3-his | | F | GCGCGCAAGCTTAGCATGGGTCATCATCACCATCA CCATGCAGGTGGAAAGTCA | 10 |
| | | R | GCGCGCCTCGAGCTACTCGATGGACAGCGG | 11 |
| DGTT4-his | | F | GCGCGCAAGCTTAGCATGGGTCATCATCACCATCA CCATCCGCTCGCAAAGCTG | 12 |
| | | R | GCGCGCGCATGCCTACATTATGACCAGCTC | 13 |
| DGTT5-his | | F | GCGCGCAAGCTTAGCATGGGTCATCATCACCATCA CCATCCGCGGGATCCGCCGG | 14 |
| | | R | GCGCGCCTCGAGTCAGCACACCTCCAGCGG | 15 |
| p9-35S-DGTT2 | | F | CCTAggatccATGGCGATTGATAAAGC | 16 |
| | | R | CCCGgaattctAGCTGATGACCAG | 17 |
| Actin2 | At3g18780 | F | TGTGACAATGGTACCGGTATGG | 18 |
| | | R | GCCCTGGGAGCATCATCTC | 19 |

TABLE 1-continued

Primers

| Name | Gene ID | | 5' Sequence 3' | SEQ ID NO |
|---|---|---|---|---|
| DGTT2-QRT | | F | TTGATAAAGCACCGACAAATGTG | 20 |
| | | R | GATGCTTTGCTTGCCCTTCT | 21 |
| WSD1 | At5g37300 | F | ACCGATCGGCCTTTGTTG | 22 |
| | | R | TGGAGAATCTGGGAGCATTGA | 23 |
| QQS | At3g30720 | F | GGTTCATTTTGCCTCACACTTCT | 24 |
| | | R | CCCATGATATGACCCTCATTTTG | 25 |
| AtBY | AT4G15210 | F | GCAGCTTAAACGTCTCAAAGAAGA | 26 |
| | | R | CCCACCAAACATCGACCATAA | 27 |
| HXXXD | At1g65450 | F | TCTTCCGACCTAACAAGGAGTTTC | 28 |
| | | R | CCAACGCCTTTCTCAGCTTCT | 29 |

Yeast Expression

Yeast strain H1266 (are2Δlro1Δdga1Δ) (Sandager et al., J Biol Chem 277, 6478-6482 (2002)) was grown to mid-log phase in YPD media (Sherman, Methods in Enzymology 350, 3-41 (2002)) and transformed with the DGTT constructs, along with an empty pYES2 vector as a negative control, according to Gietz et al. (Yeast 11, 355-360 (1995)). The transformants were selected on SC media (Sherman, Methods in Enzymology 350, 3-41 (2002)) with 2% glucose and the uracil omitted (SC-U). Colonies were picked and grown overnight in SC-U+2% glucose, before being transferred to SC-U+2% galactose, 1% raffinose. After 48 hours, 30 mL of the cultures were collected and pelleted by centrifugation for 5 min at 3000×g. Lipids were extracted and analyzed as described below.

Microsome DGTT Assays

Transformed yeast colonies were picked and grown in SC-U+2% glucose overnight, and then transferred to SC-U+2% galactose, 1% raffinose. The cells were harvested after 12 hours, and the microsomes were prepared as described in Milcamps et al. (J Biol Chem 280, 5370-5377 (2005)). The total protein concentration was measured using Bio-Rad Protein Assay Dye Reagent (see website at bio-rad.com), by adding 900 μL of the reagent to 20 μL of BSA standards or microsome samples. 50 ng of microsome were added to a mix containing 100 mM Tris, 8 mM MgCl$_2$, 1 mg/mL BSA, 20% glycerol, 0.25 mg/mL DAG, and 1.725 nmol[1-$^{14}$C]-16:0-acyl-CoA or [1-$^{14}$C]-18:1-acyl-CoA (Moravek Biochemicals, see website at moravek.com/). The reaction was incubated at room temperature for one hour. The lipids were extracted with chloroform:methanol (1:1 v/v) and phase separated with 0.2 M H$_3$PO$_4$ and 1 M KCl. The organic layer was extracted and separated on a silica TLC plate using 80:20:1 (v/v/v) petroleum ether:ethyl ether:acetic acid as the solvent. The TLC plate was exposed to film for 72 hours to visualize the radiolabeled lipids.

For the competition assay, 1.725 nmol unlabeled 16:0-acyl-CoA, 18:1-acyl-CoA, or 22:1-acyl-CoA were added. The separated TAG bands were scraped from the plate, and counted in a scintillation counter to quantify the amount of radioactivity incorporated into the lipid.

Plant Material and Generation of Arabidopsis Transgenic Plants

Arabidopsis wild-type (Col2) seeds or transgenic seeds were surface sterilized and grown on ½ Murashige and Skoog (MS) (Physiol. Plant. 15, 473-497 (1962)) agar plates containing 1% sucrose in a growth chamber adjusted to 16 h light/8 h dark (100 μm/m$^2$/s) at 22° C. after 3 days of stratification at 4° C. Fifteen-day-old wild-type and transgenic plants were transferred onto soil and grown in a growth chamber at 16 h light/8 h dark (100 μm/m$^2$/s) and 22° C. The plants were harvested at six weeks for lipid and metabolic assays. Starch analysis was performed using a Megazyme kit as per the manufacturer's instructions (Megazyme, Wicklow, Ireland). For insect assays, transgenic and wild type were grown in a short-day growth chamber at 12 h light/12 h dark (100 μm/m$^2$/s) at 22° C. The binary vector containing DGTT2 was introduced into Agrobacterium strain GV3101 by electroporation. Arabidopsis was transformed using the flower-dip method (see, Clough & Bent, Plant J 16: 735-743 (1998). Transgenic plants (T$_1$) were selected on ½ MS agar plates containing 1% sucrose and 100 mg/L kanamycin. Wild type and homozygous transgenic seedlings were grown on the same shelf of the growth chamber when used for lipid, metabolite, and insect assays.

Lipid Isolation and Quantification

Soil grown 6-week-old and 15-day-old agar-grown (grown on ½ MS agar plates containing 1% sucrose) wild-type and transgenic Arabidopsis plants were freeze-dried. Neutral lipids were extracted from dried samples using chloroform:methanol (1:1, v/v) with 100 μM internal standard tri15:0 TAG and separated on a silica thin layer chromatography (TLC) plate, using a mixture of solvents consisting of petroleum ether:ethyl ether:acetic acid (80:20:1, by volume). TAG bands were isolated from the TLC plate after separation, dissolved in toluene with 10 μM tri13:0 TAG internal standard and assayed using ESI-MS as described by Durrett et al., Proc Natl Acad Sci USA 107, 9464-9469 (2010). To quantify the amount of TAG accumulating in yeast expressing the DGTT constructs, neutral lipids were extracted from the yeast pellets and submitted for ESI-MS, following the method described by Durrett et al. (2010).

Distinct lipid and TAG bands were scraped from the TLC plates and used to prepare fatty acid methyl esters (FAMEs) by acid-catalyzed transmethylation. Identification and quantification of FAMEs was performed as described by Xu et al., EMBO J 22, 2370-2379 (2003). The amounts of lipids were calculated based on the content of fatty acids measured by gas chromatography using C15:0 as an internal standard.

Microscopy

For oil droplet visualization and TEM, the leaf samples from 6-week-old soil grown transgenic and wild-type plants were used. Whole leaf samples for TEM were fixed in a mixture of 2.5% glutaraldehyde and 2.5% paraformaldehyde in 0.1 M cacodylate buffer at 4° C. for 24 hours, post-fixed in 1% osmium tetroxide and dehydrated in a graded acetone series. Samples were infiltrated and embedded in Spurr resin (Polysciences, see website at polysciences.com). Thin sections were imaged using a JEOL 100CX Transmission Electron Microscope (Japan) at a 100 kV accelerating voltage. Freshly harvested leaf samples were used for oil droplet visualization by confocal microscopy as described by Sanjaya et al. (Plant Biotechnol J 9: 874-883 (2011)). For SEM, leaves from 6-week-old transgenic line 57 and wild-type plants were plunge frozen in liquid nitrogen, freeze dried with an EMS750X Turbo Freeze Drier (Electron Microscopy Sciences, Hatfield, Pa., USA), and mounted on aluminum stubs using carbon tape (Ted Pella, Inc., Redding, Calif., USA). These samples were coated with gold (about 20 nm thickness) for 3.5 minutes in an Emscope Sputter Coater model SC 500 (Ashford, Kent, England) purged with argon gas and coated with osmium (about 10 nm thickness) in an NEOC-AT osmium coater (Meiwafosis Co., Ltd., Osaka, Japan) for 35 seconds. The samples were examined in a JEOL JSM-6400V (Lanthanum Hexaboride electron emitter) scanning electron microscope (JEOL Ltd, Tokyo, Japan). Digital images were acquired using Analysis Pro software version 3.2 (Olympus Soft Imaging Solution Crop., Munster, Germany) at the Center for Advanced Microscopy, Michigan State University.

Analysis and Quantification of Sphingolipid Classes

Leaves of soil-grown (6-week-old) plants were used for the extraction of sphingolipids, using methods described by Markham et al. (J Biol Chem 281, 22684-22694 (2006)). Sphingolipid identification and quantification from wild type and line 57 samples was performed by ESI-high resolution/accurate mass spectrometry operating in positive ion mode. All solvents used were high performance liquid chromatography (HPLC) grade, or the highest grade available. Isopropanol, methanol, and chloroform were purchased from Macron Chemical (St. Louis, Mo., USA). Hexane and HPLC water were from Fisher (Hampton, N.H., USA). Ammonium formate was purchased from Alfa Aesar (Ward Hill, Mass., USA). The sphingolipid internal standard mixture used for mass spectrometry analysis was Avanti Sphingolipid Mix II (Avanti Polar Lipids, Alabaster, Ala., USA). Around 30 µl aliquots of total lipid extract were dried under nitrogen and subjected to mild alkaline hydrolysis of glycerolipids by the addition of 500 µl of methanol, 250 µl of chloroform, and 75 µl of 1 M KOH. Samples were incubated for two hours at 37 degrees Celsius in a shaking water bath, then neutralized with 6 µl of glacial acetic acid (Merrill et al., Methods 36, 207-224 (2005)). For ceramide (Cer) and glucosylceramide (GlcCer) analysis, samples were re-extracted by a modified Folch method (Busik et al., Methods Mol Biol 579, 33-70 (2009)) and resuspended in 300 µl of isopropanol/methanol/chloroform (4:2:1 v/v/v). For glycosylinositol-phosphoceramide (GIPC) lipid analysis, dried samples were extracted into 300 µl of isopropanol/hexane/water (3:1:1 v/v/v) (Markham et al., J Biol Chem 281, 22684-22694 (2006)), centrifuged to remove particulates, and the supernatants saved for analysis. Samples were further diluted 30-fold in isopropanol/methanol/chloroform (4:2:1 v/v/v, for ceramide and glucosylceramide analysis) or isopropanol/hexane/water (3:1:1 v/v/v, for GIPC analysis) containing a final concentration of 20 mM ammonium formate and the sphingolipid internal standard mixture diluted to 100 nM of each sphingolipid species. Samples were centrifuged and loaded into Whatman Multichem 96-well plates (Sigma Aldrich, St. Louis, Mo., USA) sealed with Teflon UltraThin Sealing Tape (Analytical Sales and Services, Prompton Plains, N.J., USA).

Samples were directly infused into a Thermo Scientific model LTQ Orbitrap Velos high resolution/accurate mass spectrometer (San Jose, Calif.) using an Advion Triversa Nanomate nano-electrospray ionization (nESI) source (Advion Ithaca, N.Y.) with a spray voltage of 1.4 kV and a gas pressure of 0.3 psi. The ion source interface settings (inlet temperature of 100° C. and S-Lens value of 50%) were optimized to maximize the sensitivity for precursor ions while minimizing in-source fragmentation. High resolution mass spectra were acquired using the FT analyzer operating at 100,000 resolving power, across the range of m/z from 400-2000, and were signal averaged for 2 minutes. All mass spectra were recalibrated offline using XCalibur software (Thermo Scientific, San Jose, Calif., USA) and the exact masses of the sphingolipid internal standards d18:1/12:0 ceramide, d18:1/12:0 glucosyl/galactosyl ceramide, d18:1/12:0 sphingomyelin, and d18:1/12:0 lactosyl ceramide. Automated peak finding, correction for $^{13}$C isotope effects, and quantitation of lipid molecular species were performed using Lipid Mass Spectrum Analysis (LIMSA) software version 1.0 (Haimi et al., Analytical chemistry 78, 8324-8331 (2006)) linear fit algorithm. Sphingolipids were quantitated as the sum of their $[M+H]^+$ and $[M+NH_4]^+$ (when present) ion abundances against the d18:1/12:0 lactosyl ceramide internal standard. As no attempts were made to correct for differences in ionization efficiency among individual molecular species of ceramide, glucosyl ceramide, and GIPC lipids, as well as the lack of an ideal internal standard for quantitation of GIPC lipids, sphingolipid molecular species are presented only as a fraction of the total normalized abundance of each lipid class.

Surface Wax and Cutin Analysis

Rosette leaves of 6-week-old soil grown transgenic and wild-type plants were used for cutin and wax analysis, using slight modifications of methods described in Molina et al., Phytochemistry 67, 2597-2610 (2006); Kosma et al., Plant Physiol 151, 1918-1929 (2009). Briefly, surface waxes were extracted from leaves by a 30 second submersion in hexane. Internal standards pentadecanoic acid (C15:0), tricosanol (C23:0), and octacosane (C28:0) were added to the hexane extracts and the solvent was removed by evaporation under nitrogen gas. Dried extracts were derivatized with 100 µL each of pyridine and N, O-bis (trimethylsilyl trifluoroacetamide) (BSTFA). Excess pyridine and BSTFA were removed by evaporation with $N_2$ and samples were dissolved in heptane:toluene (1:1 v/v) for GC-MS analysis.

Thoroughly delipidated ground leaf tissues were used for cutin monomer analysis. Methyl heptadecanoate and pentadecalactone were used as internal standards. Base catalyzed transmethylation reactions (NaOMe/MeOH) consisted of 4.5% sodium methoxide (NaOMe) and 7.5% methyl acetate in methanol in a total volume of 6 mL.

Reaction mixtures were heated overnight (~16 h) at 60° C. then allowed to cool to room temperature. Reaction mixtures were acidified with glacial acetic acid to pH 4-5, 2-3 mL saline solution were added (0.5 M NaCl), and FAMEs were extracted with 7 mL $CH_2Cl_2$. The organic phase was washed twice with dilute saline solution (0.9% NaCl, w/v) and dried over anhydrous $Na_2SO_4$. Extracts were evaporated to dryness under $N_2$ and the product silylated to convert hydroxyl groups to their trimethylsilyl ethers using BSTFA and pyridine. Excess pyridine and BSTFA were evaporated under $N_2$ and samples were dissolved in heptane:toluene (1:1, v/v) for GC-MS analysis. GC-MS temperature programs were as follows: Wax: inlet 350° C., detector 320° C., oven 130° C. for 3 min then temperature increased at 5° C./min to 325° C., 325° C. for 10 min. Cutin: inlet 330° C., detector 320° C., oven 140° C. for 3 min then temperature increased at 5° C./min to 310° C. then held at 310° C. for 10 min.

Elemental Analysis

Rosette leaves of 6-week-old soil grown transgenic line 57 and wild-type plants were harvested at the end of the day and thoroughly freeze dried, ground into fine powder in a Retsch Mill at a frequency of 25 for 2 min and used to measure carbon, hydrogen, sulfur, nitrogen and ash content employing a commercial service (Elemental Analysis Inc., Lexington, Ky., USA). Protocols are listed on the website at elementalanalysis.com. Calculation of heating value (MJ/kg DW)=0.3491XC+1.1783XH+0.1005XS−0.0151XN−0.1034X0−0.0211Xash; X's entered as mass percentages (Guar & Reed, An atlas of thermal data for biomass and other fuels. NREL/TB-433-7965, UC Category: 1310, DE95009212, National Renewable laboratory, Golden Colo., USA (1995)).

Insect Feeding Assay and JA-Ile Quantification Using Mass Spectrometry

Insect feeding trials and JA-Ile analysis by LC-MS/MS were performed as described by Koo et al. (Front Plant Sci 3: 19 (2011)). *S. exigua* eggs (Benzon Research, see website at benzonresearch.com/) were hatched at 30° C. on artificial insect diet (Southland Products INC., Lake Village, Ark.) for 2 days and used for feeding experiments. Newly hatched neonates were allowed to grow on artificial diet for another 2 days before being transferred to 6-week-old plants. Ten larvae were reared per single pot, each of which contained two plants of the same genotype. A total of 14 pots were used for each genotype. Larvae were caged in each pot using an inverted clear plastic cup with an opening on the top covered with miracloth for air exchange. Plants with insects were grown in a growth chamber maintained at 2° C. under a 12-h light (100 $\mu m/m^2/s$) and 12-h dark cycle. Fresh weight of individual larvae was determined 14 days after the start of the feeding trial. For JA-Ile measurements, approximately 350 mg of leaf tissue was harvested from insect damaged and undamaged control plants at the end of the trial. Jasmonate extraction and JA-Ile quantification by LC-MS/MS were performed as previously described (Koo et al., Front Plant Sci 3: 19 (2011)).

Microarray and Data Analysis

Leaves from 6-week-old plants grown on soil at 22° C. under 16 h light/8 h dark (100 $\mu m/m^2/s$) were used for isolating total RNAs with the RNeasy plant mini kit (Qiagen). Subsequently, the total RNA samples were pretreated with RNase-free DNase I and cleaned with a Plant Total RNA isolation kit (Qiagen). Four biologically independent RNA samples from DGTT2 line 57 and wild type plants each were used for the microarray experiments. Probe preparation, hybridization to the 4-plex GeneChip *Arabidopsis* ATH1 Genome Arrays (NimbleGen, see website at nimblegen.com), and subsequent processing steps were performed according to the manufacturer's instructions (Gene Expression Center, University of Wisconsin). Arrays were scanned at 5 µm on an Axon4000B Scanner (Molecular Dynamics, Sunnyvale, Calif., USA). Microarray data were analyzed using Partek Genomics Suite software (2009; see website at partek.com). Microarray data were analyzed using Partek Genomics Suite software (2009; see website at partek.com. RMA normalization (Irizarry et al., Nucleic Acids Res 31, el5 (2003); Irizarry et al., Biostatistics 4, 249-264 (2003)) was performed by Partek upon data import, producing log 2-transformed intensity values. Probe set log-intensities had a bimodal distribution with a valley at about 9 (not shown). Such bimodality appears to be a common feature of oligonucleotide arrays, and the lower mode is thought to correspond to unexpressed genes (Irizarry et al., Biostatistics 4, 249-264 (2003); see website at stat.ethz.ch/pipermail/bioconductor/2006-June/013255.html). Therefore, probe sets whose maximal values across all arrays were less than 9 were taken to target genes that were not expressed at detectable levels in any of the samples and were therefore removed from further analysis. This decreased the number of probe sets in the analysis from 30,361 to 18,221.

The PCA plot of the filtered dataset did not show clear separation between wild type and transgenic plants (data not shown), indicating that the transgene expression did not have a strong effect on the global gene expression profile of the plants. Since the experiment was performed on 2 NimbleGen chips, with 4 arrays per chip (2 wild type and 2 transgenic each), two factor mixed model ANOVA analysis was employed to account for the effects of genotype and chip, the latter being a random effect. P values were calculated for the wild type vs. line 57 contrast. Multiple testing correction using the step-up FDR method identified only one gene with adjusted p value<0.05, encoding a transposable element. Therefore, putative hits were selected using the unadjusted p value threshold of 0.002 and fold change threshold on >2 or <−2. This identified 15 genes (see Table 2), several of which could be expected to be false positives.

TABLE 2

Elemental analysis of wild type and transgenic line 57.

| | Carbon (C) % | Hydrogen (H) % | Nitrogen (N) % | Oxygen (O) % | Sulfur (S) % | Ash % | Heating value (MJ/kg DW)* |
|---|---|---|---|---|---|---|---|
| WT | 36.01 ± 0.56 | 4.97 ± 0.17 | 6.28 ± 0.19 | 40.89 ± 0.10 | 1.37 ± 0.03 | 18.39 ± 0.31 | 13.85 ± 0.40 |
| 57 | 36.19 ± 0.37 | 5.09 ± 0.08 | 6.04 ± 0.29 | 40.46 ± 0.20 | 1.27 ± 0.14 | 17.67 ± 0.31 | 14.12 ± 0.23 |

*Heating value (MJ/kg dry biomass (DW)) = 0.3491XC + 1.1783XH + 0.1005XS − 0.0151XN − 0.1034XO − 0.0211Xash; X's entered as mass percentages (Guar and Reed, An Atlas of Thermal Data for Biomass and Other Fuels (Golden, CO: National Renewable Laboratory, 1995), (n = 3 average ± SD).

Q-RT PCR

Total RNA was extracted from 15-day-old and 6-week-old DGTT2 transgenic and wild-type plants. cDNA synthesis, q-RT PCR with gene specific primers (see Table 1) and data analysis was performed as described by Sanjaya et al., Plant Biotechnol J 9: 874-883 (2011).

Accession Numbers

The protein sequences used in the phylogenetic analysis were as follows DGTT1, XP_001702848.1; DGTT2, XP_001694904.1; DGTT3, XP_001691447.1; DGTT4, XP_001693189.1; DGTT5, XP_001701667.1; *Arabidopsis*

DGAT2, NP_566952.1; VfDGAT2, DQ356682.1; RcD-GAT2, DQ923084.1; ScDGA1, NP_014888.1; and OtDGAT2B, XP_003083539.1.

The microarray data set is deposited into GEO (see website at ncbi.nlm.nih.gov/geo) with accession number GSE38898.

EXAMPLE 2

Multiple Putative *Chlamydomonas* DGAT2 Isoforms

Amino acid sequence similarity to *Arabidopsis* DGAT2 was used to identify potential DGAT orthologs, using BLAST against Version 3 of the *Chlamydomonas* genome.

The BLAST search results returned five gene models with high sequence similarity to the *Arabidopsis* type-2 DGAT. These five candidates were named Diacylglycerol Acyltransferase Type Two (DGTT) 1-5 and compared to type-2 DGATs from *Arabidopsis thaliana, Ostreococcus tauri*, yeast (*Saccharomyces cerevisiae*), castor bean (*Ricinus communis*), and tung tree (*Vernicia fordii*).

When analyzed with MEGA5 (Tamura et al., Mol Biol Evol 28, 2731-2739 (2011)), DGTT1 was the most closely related to Sc-DGA1. DGTT2, DGTT3 and DGTT5 formed their own clade, as did the three land plant DGATs. Ot-DGAT2B and DGTT4 were both more similar to the land plant DGATs than to the other *Chlamydomonas* DGTTs (FIG. 1A; see sequence comparison below).

```
                                                          (SEQ ID NO: 30)
CrDGTT1   ---------- ---------- ----MQSKRC AELASGALWP (SEQ ID NO: 31)
CrDGTT2   ---------- ---------- ---MAIDKAP TNVRIWSDGV (SEQ ID NO: 32)
CrDGTT3   MAGGKSNGTG AADAHVRTSH LTLKAGEDPP PNVRIYSDGI (SEQ ID NO: 33)
CrDGTT4   ---------- ---------- ---------- ----------

(SEQ ID NO: 34)
CrDGTT5   ---------- --------MT PRDPPVPRPP PGVRQYTDGR (SEQ ID NO: 35)
AtDGAT2   ---------- ---------- ---MGGSREF RAEEH-----

(SEQ ID NO: 36)
VfDGAT2   ---------- ---------- ----MGMVEV KNEEE--VTI (SEQ ID NO: 37)
RcDGAT2   ---------- -MGEEANHNN NNNNNINSNDE KNEEKSNYTV (SEQ ID NO: 38)
ScDGA1    ---------- --------MS GTFNDIRRRK KEEGSPTAGI (SEQ ID NO: 39)
OtDGAT2B  ---------- ---------- ---------- ----------

CrDGTT1   MDRDQMRDRD PWKLRDR--- ---------- ----------

CrDGTT2   TEKGKQSIFS SLVAMLT--- ---------- ----------

CrDGTT3   KPDARQNLLV QILAGIT--- ---------- ----------

CrDGTT4   --MPLAKLRN VVLEYAA--- ---------- ----------

CrDGTT5   SASYVLPLPY RLLAQLT--- ---------- ----------

AtDGAT2   --------SN QFHSIIA--- ---------- ----------

VfDGAT2   FKSGEIYPTN IFQSVLA--- ---------- ----------

RcDGAT2   VNSRELYPTN IFHALLA--- ---------- ----------

ScDGA1    TERHENKSLS SIDKREQTLK PQLESCCPLA TPFERRLQTL

OtDGAT2B  -------MSR SIVDHGV--- ---------- ----------

CrDGTT1   ---------- --------AI SQAWVWPLLI G-------TL

CrDGTT2   -----LFIYC GWMHVLLALV I-LSFWYRWA ---------L

CrDGTT3   -----MSIYV GFMNYFMLLV V-LSYWSRIC ---------R

CrDGTT4   -----IAIYV SAIYTSVVLL PSALALFYLF GATSPSAWLL

CrDGTT5   -----LGLYV GFPYILLGLL LGTAAGSRAA ---------A

AtDGAT2   -----MAIWL GAIHFNVALV LCSLIFLPPS -----LSLMV
```

```
VfDGAT2      -----LAIWL GSFHFILFLV SSS-IFLPFS -----KFLLV

RcDGAT2      -----LSIWI GSIHFNLFLL FISYLFLSFP -----TFLLI

ScDGA1       AVAWHTSSFV LFSIFTLFAI STPALWVLAI P-------YM

OtDGAT2B     -----LLVWL GLFHALVVVV VVAIVALERR -----RAMTV

CrDGTT1      LYVQS----- -----TTLTI AFLLWHIWKV MASYFPGARL

CrDGTT2      VTVLLLYSTL LLPPKPVLWG PVCRSWIFQT WREYFKFSYV

CrDGTT3      YVVLALLGTL ALPCKPVLWP AFNKLWIFKT WRHYFHYSFL

CrDGTT4      LAAFLALTFT PLQLTTGALS ERFVQFSVAR AAAYFPTRVV

CrDGTT5      AALALTLGSL LVPAPPHIRQ GMLDSALFRL WRAYFNYSYA

AtDGAT2      LGLLSLFIFI PIDHRS-KYG RKLARYICKH ACNYFPVSLY

VfDGAT2      IGLLLFFMVI PINDRS-KLG QCLFSYISRH VCSYFPITLH

RcDGAT2      VGFFVVLMFI PIDEHS-KLG RRLCRYVCRH ACSHFPVTLH

ScDGA1       IYFFFDRSPA TGEVVNRYSL RFRSLPIWKW YCDYFP-ISL

OtDGAT2B     LAALMSLSVV PRRIRP-RWG VTLARAITRT AKSYFPCALT

CrDGTT1      IKTADLDP-- ---------- ---------- ----------

CrDGTT2      FDEVLDSKK- ---------- ---------- ----------

CrDGTT3      IEEPLDPNK- ---------- ---------- ----------

CrDGTT4      VTDPEAFRT- ---------- ---------- ----------

CrDGTT5      YDQLPDFNR- ---------- ---------- ----------

AtDGAT2      VEDYEAFQP- ---------- ---------- ----------

VfDGAT2      VEDINAFRS- ---------- ---------- ----------

RcDGAT2      VEDMNAFHS- ---------- ---------- ----------

ScDGA1       IKTVNLKPTF TLSKNKRVNE KNYKIRLWPT KYSINLKSNS

OtDGAT2B     FENEEAYLKG ARK------- ---------- ---------

CrDGTT1      ---------- AGRYIFVSHP HGVIAISDWL AFATEALGFS

CrDGTT2      ---------- --KYIFAEFP HGVFPMGPLI GATECQIMFP

CrDGTT3      ---------- --RYIFVEFP HGAFPIGPIV AGTLMQTLFP

CrDGTT4      ---------- DRGYLFGFCP HSALPIALPI AFATTSPLLP

CrDGTT5      ---------- --PHIFVNSP HGAFPLSQIL CISLSNIVWP

AtDGAT2      ---------- NRAYVFGYEP HSVLPIGV-V ALCDLTGFMP

VfDGAT2      ---------- DRAYVFGYEP HSVFPIGV-M ILS--LGLIP

RcDGAT2      ---------- DRAYVFGYEP HSVFPLGV-S VLSDHFAVLP

ScDGA1       TIDYRNQECT GPTYLFGYHP HGIGALGAFG AFATEGCNYS

OtDGAT2B     ---------- GVGRLVGLEP HGALPLSV-I AFADYFMFDE

CrDGTT1      --------KL FPGLDLRCAT LASNFWVPGL REYILSHGMC

CrDGTT2      ---------- --GFDIFGLA ANVVFTVPFW RHFVAWLGSV

CrDGTT3      ---------- --HMMIYSVA ASVVFYIPFW RHFITWIGSV

CrDGTT4      ---------K ELRGRTHGLA SSVCFSAPIV RQLYWWLGVR

CrDGTT5      ---------- --GFPVHSLA ASVLWYIPLW RHMKAALGAA

AtDGAT2      ---------- --IPNIKVLA SSAIFYTPFL RHIWTWLGLT

VfDGAT2      ---------- --LPNIKFLA SSAVFYTPFL RHIWSWCGLT
```

-continued

```
RcDGAT2     ---------- --LPKMKVLA SNAVFRTPVL RHIWTWCGLT
ScDGA1      --------KI FPGIPISLMT LVTQFHIPLY RDYLLALGIS
OtDGAT2B    DGIEARGMNH AASMNSRALA SGAIFHVPLV RHLWTWLGLE
CrDGTT1     GVGRDTLARV LTGKPGRAVV LVVGGASEAL LAAEGT----
CrDGTT2     PATTRDFKRV LKQ---GSVA VIVGGIAEMY MQSPTK----
CrDGTT3     PATPGNFKRL LKK---GSVA VIVGGIAEMY MGNKKK----
CrDGTT4     PATRQSISGL LRAR--KVAV LVPGGVQEVL NMEHGK----
CrDGTT5     PASRDNARML LRHR--GSVA VLAGGIAEMY TSSPSRAAAA
AtDGAT2     AASRKNFTSL LDSG--YSCV LVPGGVQETF HMQHDA----
VfDGAT2     PATRKNFVSL LSSG--YSCI LVPGGVQETF YMKQDS----
RcDGAT2     SATKKNFTAL LASG--YSCI VIPGGVQETF YMKHGS----
ScDGA1      SVSRKNALRT LSKN--QSIC IVVGGARESL LSSTNG----
OtDGAT2B    PISRRRMTSM LSDG--STCV IVPGGVAECM AMERGV----
CrDGTT1     ---------- ---------- ---------- ----------
CrDGTT2     ---------- ---------- ---------- ----------
CrDGTT3     ---------- ---------- ---------- ----------
CrDGTT4     ---------- ---------- ---------- ----------
CrDGTT5     TEPDEAAAAG GAIDTTEAAG ATGSSSTTTS PPQPKEQQRD
AtDGAT2     ---------- ---------- ---------- ----------
VfDGAT2     ---------- ---------- ---------- ----------
RcDGAT2     ---------- ---------- ---------- ----------
ScDGA1      ---------- ---------- ---------- ----------
OtDGAT2B    ---------- ---------- ---------- ----------
CrDGTT1     ---------- ---------- ---------- ------YDLV
CrDGTT2     ---------- ---------- ---------- ------EQIM
CrDGTT3     ---------- ---------- ---------- ------ERIK
CrDGTT4     ---------- ---------- ---------- ------EVAY
CrDGTT5     GEQRQGPRKG LKGLLKGPKD DPDPAAEEEQ GLGLAPERIK
AtDGAT2     ---------- ---------- ---------- ------ENVF
VfDGAT2     ---------- ---------- ---------- ------EIAF
RcDGAT2     ---------- ---------- ---------- ------EIAF
ScDGA1      ---------- ---------- ---------- ------TQLI
OtDGAT2B    ---------- ---------- ---------- ------ETLY
CrDGTT1     LRNRKGFVRL ALQTG-AS-L VPVLSYGETD TFHTYIPPPC
CrDGTT2     LKDRKGFVRV AVEEGVDGGI VPVYHFGNSQ VLDFG---PQ
CrDGTT3     LVGRRGFARI ALEEQVDG-I VCVYYFGQSQ VLDFG---PS
CrDGTT4     LSSRTGFVRL AVQHGAP--L VPVWAFGQTR AYSWFRPGPP
CrDGTT5     LLGRRGFVRL AVEMGVP--I VPIYHMGNSK ILTFG---PQ
AtDGAT2     LSRRRGFVRI AMEQGSP--L VPVFCFGQAR VYKWWKPDCD
VfDGAT2     LKARRGFIRI AMQTGTP--L VPVFCFGQMH TFKWWKPDGE
```

```
RcDGAT2      LKARRGFVRV  AMEMVKP--L  VPVFCFGQSN  VYKWWKPDGE

ScDGA1       LNKRKGFIKL  AIQTGNIN-L  VPVFAFGEVD  CYNVLSTKKD

OtDGAT2B     LKRRYGFVKI  AIQTGAA--L  VPAYTFGQTR  AYKYWRLGPP

CrDGTT1      SRAAAVMKVL  KQVFGFSTPL  CWGTGLFG-G  WGMLALQVPL

CrDGTT2      AMAS-----V  SRRLRAALGF  LYGVAYLP--  ---LPRRRNI

CrDGTT3      WLAD-----F  SRRMRTSFGY  LTGWMGLP--  ---VPRPIPI

CrDGTT4      LVPTWLVERI  SRAAGAVPIG  MFGQYGTP--  ---MPHREPL

CrDGTT5      SLQQ-----L  SRRLRMALGA  VFGVWGLP--  ---VPRPQPL

AtDGAT2      LYLK-----L  SRAIRFTPIC  FWGVFGSP--  ---LPCRQPM

VfDGAT2      LFMK-----I  ARAIKFTPTI  FWGVLGTP--  ---LPFKNPM

RcDGAT2      LFMK-----I  ARAIKFSPIV  FWGVLGSH--  ---LPLQRPM

ScDGA1       SVLGKMQLWF  KENFGFTIPI  FYARGLFNYD  FGLLPFRAPI

OtDGAT2B     LVPTSVANWF  SKTFSFAPMV  FWGKWFTP--  ---IPYATPL

CrDGTT1      TVVVGAPIQV  DK-----VSS  PTEAEVAALH  KTYTEALQKL

CrDGTT2      YMVCGKPVPV  TRT--ARDDP  KFEEVVDATH  AAVMAALQEA

CrDGTT3      YMVNGKPIPV  PKV--ARDSP  EFDKEVDKLL  DATITELGEM

CrDGTT4      TIVVGRPIPV  PELAPGQLEP  EPE-VLAALL  KRFTDDLQAL

CrDGTT5      MMCVGSPIPV  PYVDPAAEPE  RFEAVVAAVH  GQVVAAFQDL

AtDGAT2      HVVVGKPIEV  TKTL----KP  TDE-EIAKFH  GQYVEALRDL

VfDGAT2      HVVVGRPIEV  KQNP----QP  TAE-EVAEVQ  REFIASLKNL

RcDGAT2      HVVVGKPIEV  KQNP----QP  TVE-EVSEVQ  GQFVAALKDL

ScDGA1       NVVVGRPIYV  EKK----ITN  PPDDVVNHFH  DLYIAELKRL

OtDGAT2B     HTVVGELIET  TQND----NP  SRE-EVQAKL  DEFIVAMRSL

CrDGTT1      WDDTVDKYGK  GVKRPLAIVQ  *

CrDGTT2      YDRHKTEY--  GWADRPLVIS  *

CrDGTT3      YNRHRGEY--  GWGDRPLSIE  *

CrDGTT4      YDKHKAQFGK  GEELVIM*--  -

CrDGTT5      YNRYRVQYGC  GWERRPLEVC  -

AtDGAT2      FERHKSRVGY  -DLELKIL--  -

VfDGAT2      FERHKARVGY  SDLKLEIF--  -

RcDGAT2      FERHKARVGY  ADLTLEIL--  -

ScDGA1       YYENREKYG-  VPDAELKIVG  *

OtDGAT2B     YDRHKSAHGY  ADVDLVVC--  -
```

Figure 1B:
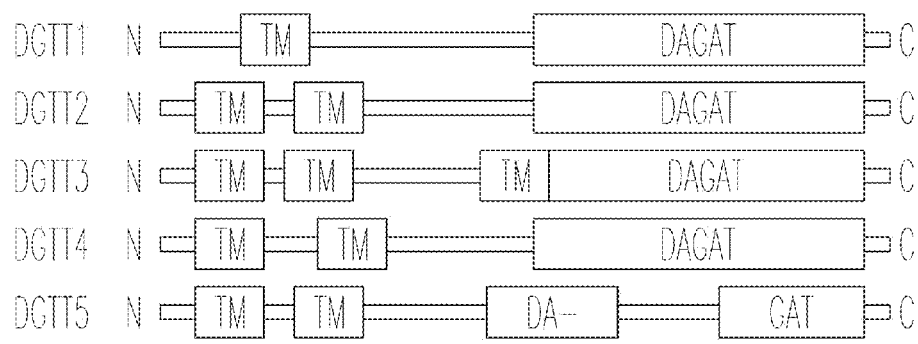

Structural analysis of the gene model-translated protein sequences was performed in silico using the TMHMM Server 2.0 (see website at cbs.dtu.dk/services/TMHMM/) to predict transmembrane sequences. All five candidates had 1-3 transmembrane domains in the N-terminal half of the protein, consistent with other type-2 DGATs. SignalP V3.0 (see website at cbs.dtu.dk/services/SignalP/) and TargetP V1.1 (website at cbs.dtu.dk/services/TargetP/) failed to identify potential cellular localization signals. Searching against the NCBI Conserved Domain Database revealed a DAGAT domain in the C-terminal half of all five candidates, although DGTT5 had an apparent disruption in its domain (FIG. 1B).

EXAMPLE 3

Expression of DGTT Constructs in Yeast

Figure 1C:
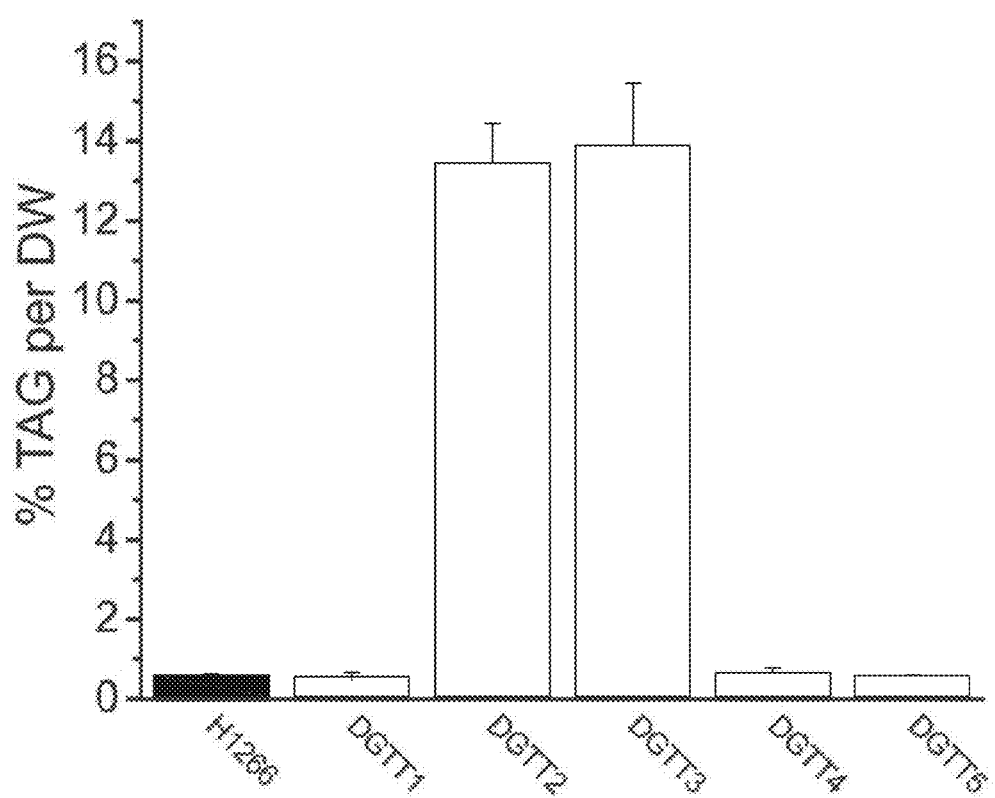

To test the function of the predicted DGTT genes, the coding sequences of DGTT2-5 were isolated and expressed in yeast strain H1266, a triple knockout mutant for DGA1, LRO1, and ARE2 (Sandager et al., J Biol Chem 277, 6478-6482 (2002)). This strain has very little native DGAT activity, providing a suitable background for testing the Chlamydomonas DGAT2 candidates. The inventors were unable to isolate a DGTT1 cDNA based on the available gene model. The presence of the DGTT2-5 proteins was confirmed in yeast by immunoblotting. To quantify the amount of TAG produced, electrospray ionization mass spectrometry (ESI-MS) was performed on lipid extracts from the transgenic yeast (FIG. 1C). Both DGTT2-producing and DGTT3-producing yeast accumulated considerable levels of TAG (13.4 and 13.9% per dry weight (DW), respectively) compared to the empty vector control (0.5% per DW). Both DGTT4-producing and DGTT5-producing strains showed TAG levels equivalent to the empty vector (0.6 and 0.5% per DW, respectively), indicating that these may not have DGAT activity, or lack appropriate co-factors or substrates in yeast necessary for proper DGAT activity.

EXAMPLE 4

In Vitro Activity of Recombinant Proteins

Figure 2A:
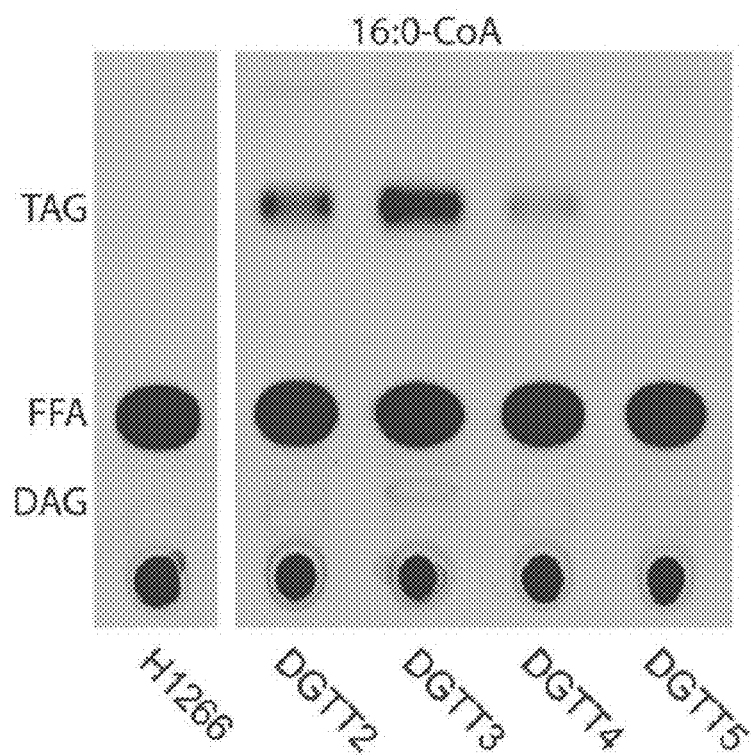
FIG. 2A-2G illustrates DGTT activity in transgenic yeast microsomes and that overexpression of DGTT2 affects the seedling phenotype.
Figure 2B:
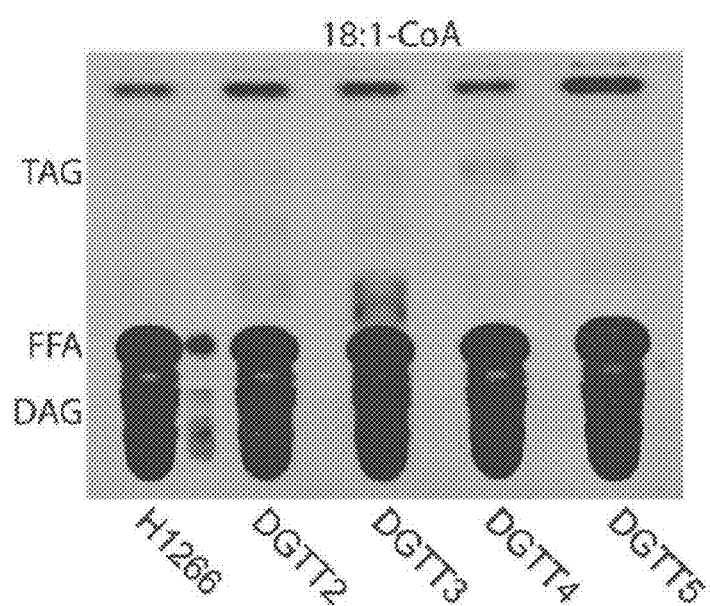

The substrate preference of the DGTT proteins was estimated in an in vitro reaction with isolated microsomes. DGTT-containing microsomes were incubated with radiolabeled palmitoyl-CoA (16:0) and oleoyl-CoA (18:1), along with dioleoyl DAG. The level of activity was estimated from their incorporation of radiolabel into isolated TAGs. Comparison of the results using the two different substrate acyl-CoAs suggested an apparent difference in substrate specificity, with DGTT2 and DGTT3 preferring 16:0-CoA and DGTT4 preferring 18:1-CoA (FIGS. 2A and 2B). These assays also confirmed that DGTT5 has essentially no activity under these assay conditions. This result, in conjunction with the apparent lack of expression of its gene in Chlamydomonas and disruption in the DAGAT domain, indicates that DGTT5 is a non-active pseudogene.

Although DGTT2 and DGTT3 belong to the same clade, following nitrogen-deprivation the level of DGTT2 transcripts remained unchanged, whereas DGTT3 transcript levels increased (Miller et al. Plant Physiol 154, 1737-1752 (2010); Boyle et al., J Biol Chem 287(19): 15811-15825 (2012)). When expressed in yeast, DGTT2 activity in vitro was higher than that of the other isoforms.

Figure 2C:
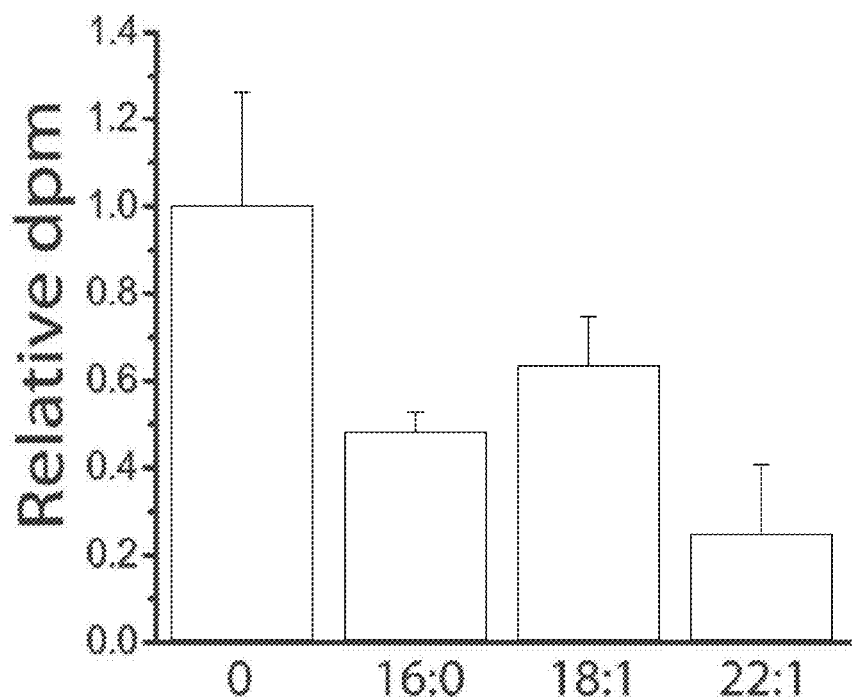

Based on the observed activity levels, the inventors focused on the characterization of the DGTT2 enzyme as a potential tool for the manipulation of cytosolic acyl-CoAs in vegetative tissues of plants, the primary goal of this study. A microsome-based competition assay was used to further probe the substrate specificity of DGTT2. When incubated with equimolar amounts of $^{14}$C-labeled and unlabeled 16:0-CoA, the radioactivity in the TAG band was reduced to ~50% compared to the reactions with only $^{14}$C-labeled 16:0-CoA (FIG. 2C). When incubated with equal moles of unlabeled 18:1-CoA, the decrease was only about 40%. However, when incubated with equal moles of unlabeled 22:1-CoA, the decrease was ~75%.

Together, these data indicated that DGTT2 is able to incorporate varying acyl-CoA species into TAG, perhaps preferring very long chain acyl groups, which is relevant for the interpretation of lipid data for the transgenic plants described below.

EXAMPLE 5

Different Roles for Different DGATs

High-throughput transcript profiling of Chlamydomonas under nitrogen-deprivation showed that the expression levels and patterns of the five putative DGAT2-encoding genes varied considerably. DGTT1 was the most highly regulated, being strongly up-regulated following nitrogen-deprivation. Based on the sequence analysis, DGTT2 and DGTT3 are the most similar. Additionally, they showed near-identical results in yeast assays. Although DGTT3 did show a change in expression during nitrogen-deprivation, the overall change was less than two-fold, which was statistically insignificant. For these reasons, it was assumed that their activity in Arabidopsis would also be similar. The results for either one of the two isoforms were representative of both.

Structural analysis of the DGAT2 candidates indicates that they are similar but not identical to previously identified DGAT2 proteins. The absence of predicted signal or targeting sequences may be explained by the fact that the programs were trained on land plant signal sequences, which could hinder the detection of such sequences in Chlamydomonas. Given the absence of obvious organellar targeting sequences, the most likely location is the endoplasmic reticulum (ER) membrane, which is the main site of TAG synthesis in plants (Lung and Weselake, Lipids 41, 1073-1088 (2006)). Recently, however, the existence of a separate TAG assembly pathway in chloroplasts has been suggested (Fan et al., 2011; Goodson et al., 2011). It seems possible that some of the DGAT2 proteins are preferentially associated with the endoplasmic reticulum, whereas other DGAT2 proteins are targeted preferentially to the chloroplast envelope by mechanisms that would not require classic targeting sequences.

Biochemically, DGTT2 possesses broad substrate specificity and is able to incorporate varying acyl-CoA species into TAG in vitro. However, it is unclear what the natural substrate of DGTT2 may be in Chlamydomonas. Both Ostreococcus DGAT2B and yeast Dga1 also have broad substrate specificity, in contrast to the more substrate specific type 2 DGATs found in land plants (Wagner et al., 2010). These, along with the relative abundance of type 2 DGATs in other green algae, suggest a more distinct role for these enzymes in algae, compared to plants. This difference may be related to the different roles and regulation of TAG synthesis, as microalgae produce oil in response to environmental stresses, whereas land plants produce oil primarily during seed development.

EXAMPLE 6

Production of DGTT2 in Arabidopsis Affects Seedling Growth

To explore DGTT2 as a tool to manipulate acyl-CoA pools in plants and to engineer TAGs in vegetative tissues, the full length DGTT2 coding sequence was expressed in Arabidopsis under the control of the heterologous constitutive 35S cauliflower mosaic virus (CaMV) promoter, 35S: DGTT2. Five homozygous lines, 14, 22, 46, 52 and 57, were carried forward to the $T_4$ generation and used for detailed analysis.

Figure 2D:
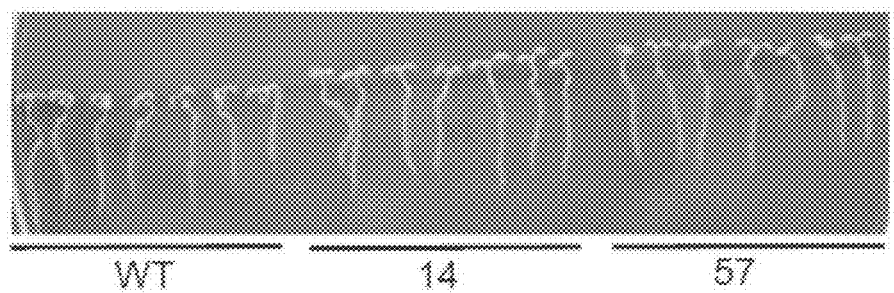
Figure 2E:
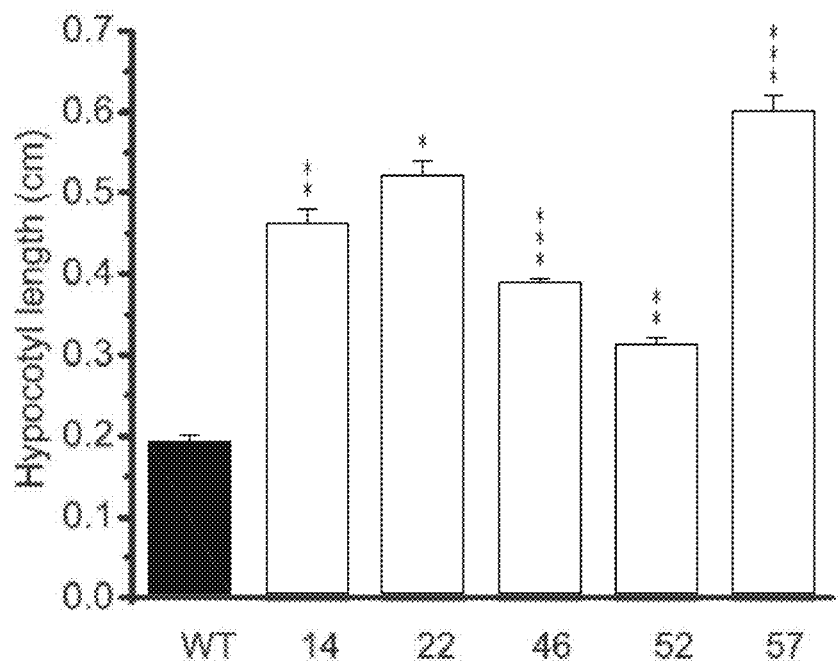
Figure 2F:
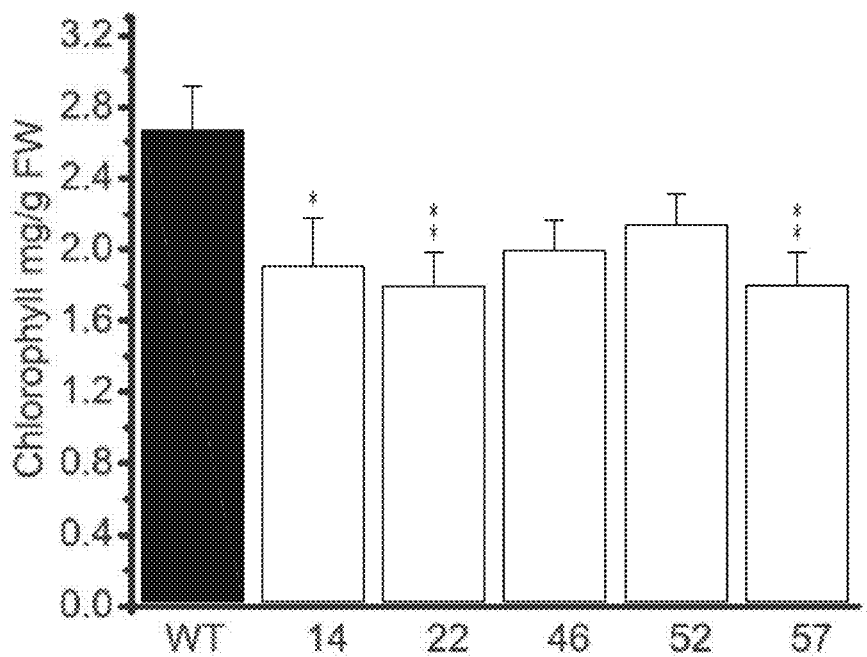

The hypocotyls of the DGTT2 transgenic 10-to-12-day-old seedlings grown on MS agar plates supplemented with 1% sucrose were strikingly more elongated than those of control plants (FIG. 2D-2E). The DGTT2 transgenic plants were also slightly pale in color. Consistent with the pale green phenotype, the total chlorophyll content in the DGTT2 transgenic lines was 28-30% lower (FIG. 2F). On soil, all transgenic lines followed wild-type growth and development patterns. To determine the abundance of DGTT2 mRNA in the seedlings of DGTT2 over-expressors, mRNA from 15-day-old plantlets was quantified using q-RT-PCR. The normalized expression of DGTT2 relative to ACTIN2

(ratio of DGTT2/ACTIN2) in the DGTT2 transgenic plants ranged from 2 to 7 in the independent transgenic lines tested (see FIG. 2G), while no transcripts were detected in the wild type.

EXAMPLE 7

DGTT2 Production Causes Accumulation of TAGs with VLCFAs

Figure 2G:
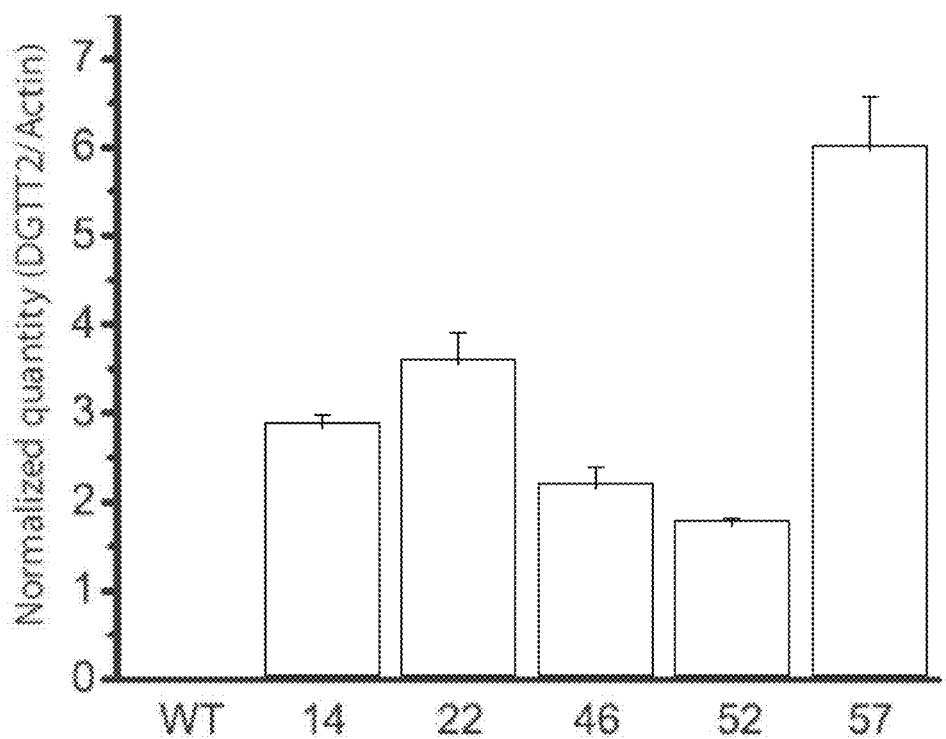
Figure 3A:
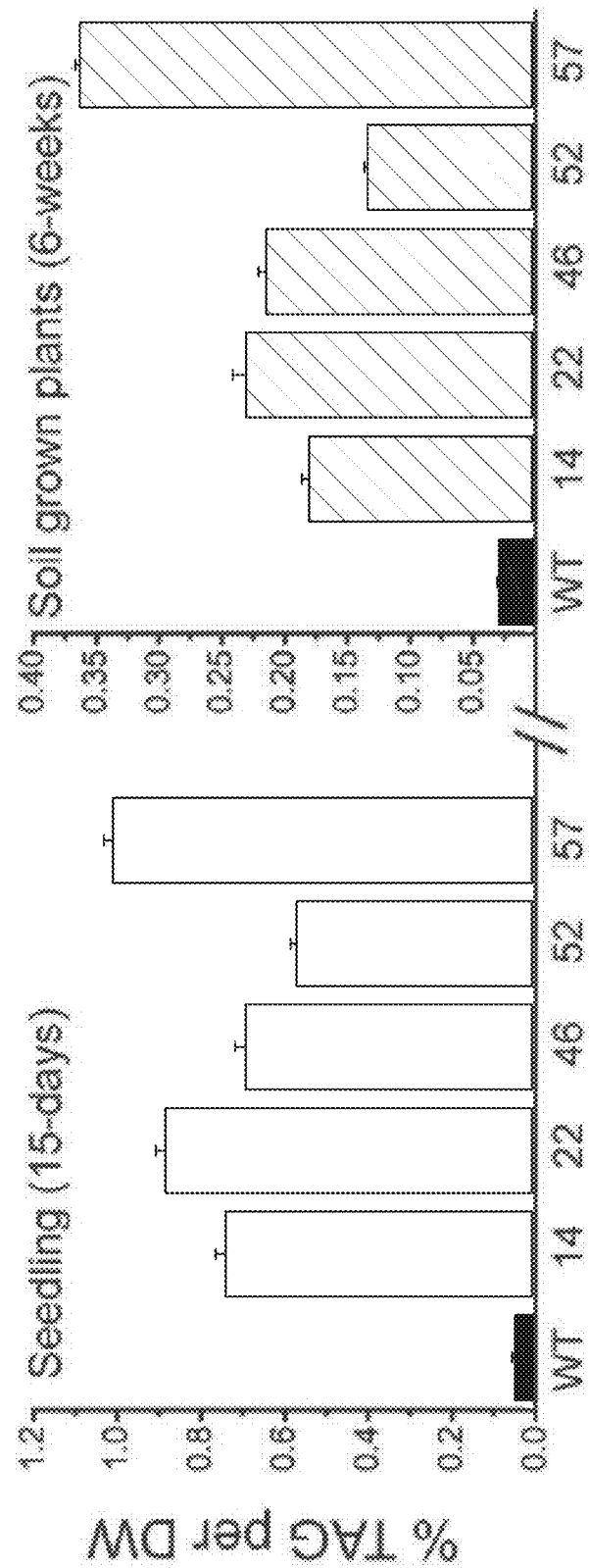
Figure 3D:
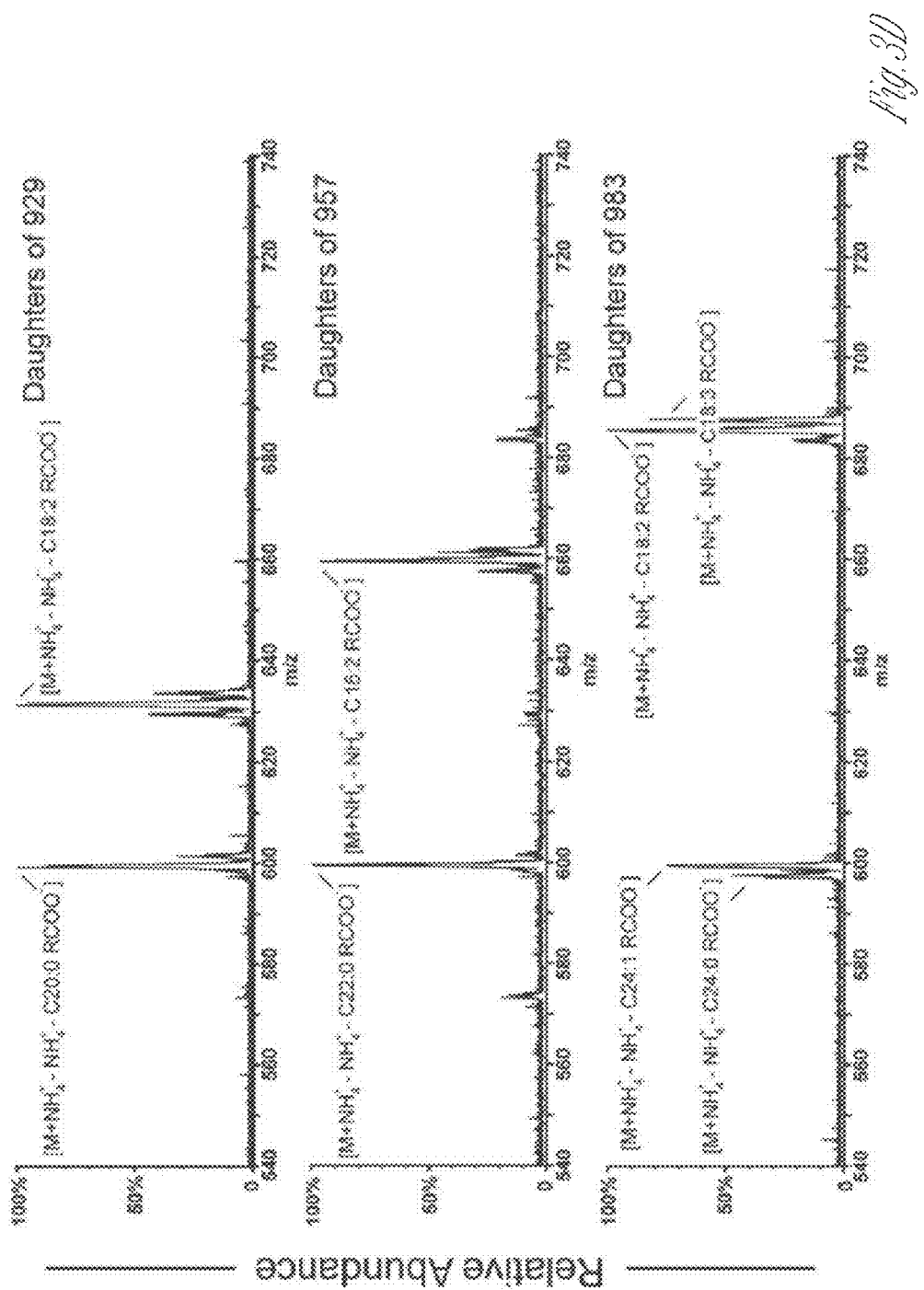
Figure 3C:
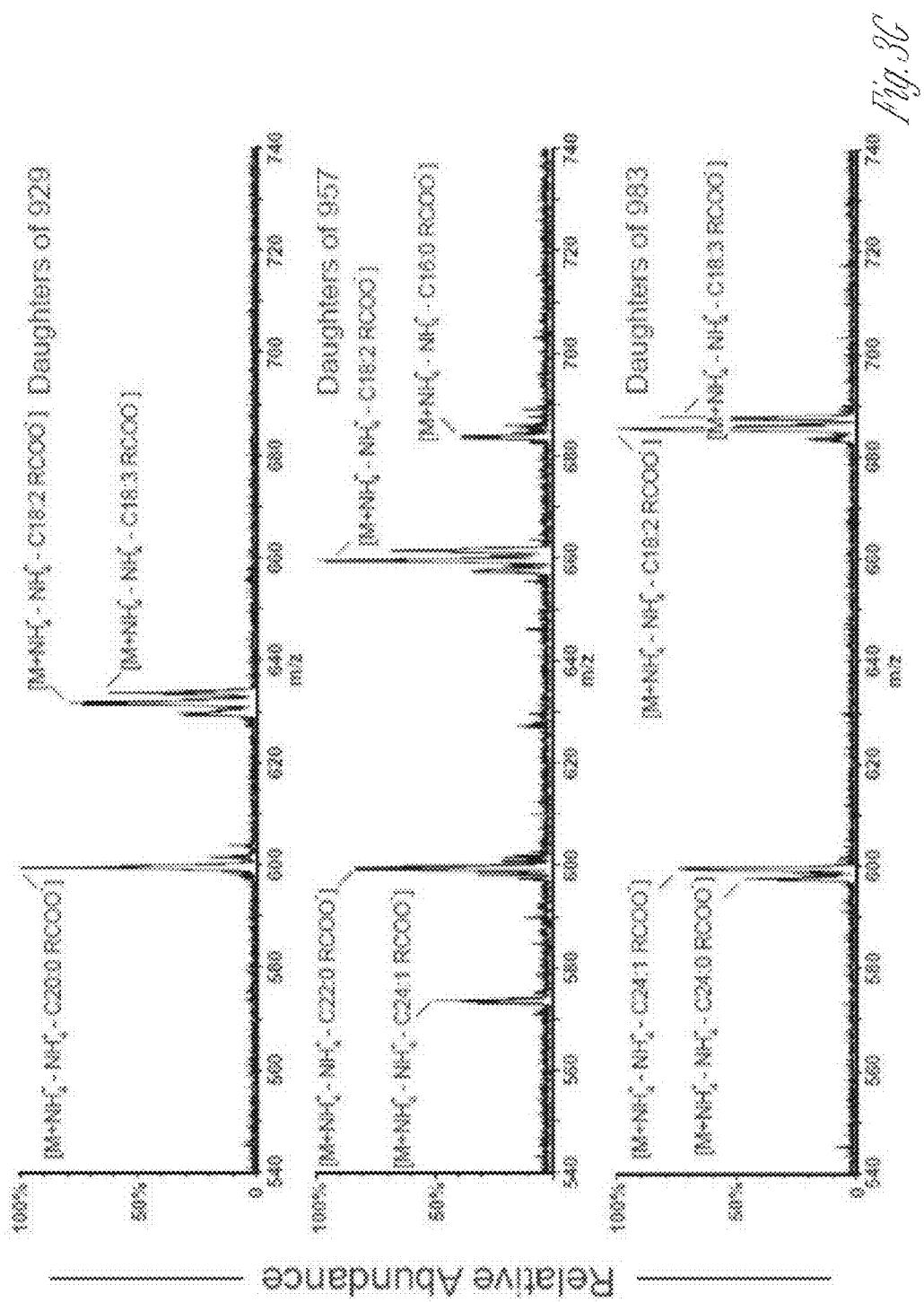

To determine the effect of DGTT2 production on the accumulation of TAG, 15-day-old whole seedlings were analyzed by ESI-MS. The TAG levels in 15-day seedlings of transgenic lines were increased up to 22-fold and 25-fold (FIG. 3A). Lines 22 and 57 contained 0.88% and 1.00% TAG per dry weight, respectively, compared to 0.04% TAG per dry weight in the wild type. The increase in TAG levels correlated well with the relative abundance of DGTT2 transcript in each line (FIG. 2G). Comparison of ESI-MS spectra of neutral lipid extracts from the wild type and transgenic line 57 showed an abundance of TAG molecular species containing VLCFAs in the transgenic line (FIG. 3B-3C). The presence of long and very long chain fatty acid-containing TAG molecular species in the seedling extracts of line 57 was further confirmed by ESI-MS/MS (FIG. 3D), which produced product ions with masses consistent with the loss of VLCFAs. These spectra were consistent with each TAG molecule containing only one VLCFA.

Figure 4A:
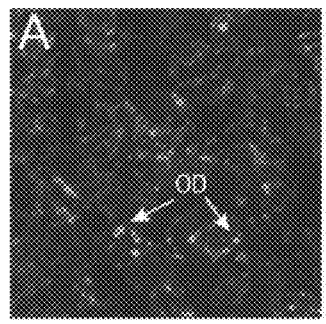
Figure 4B:
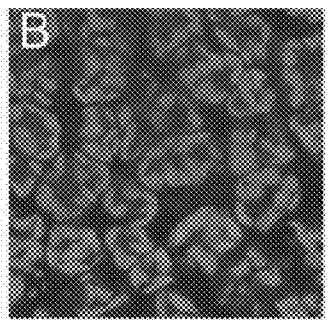
Figure 4C:
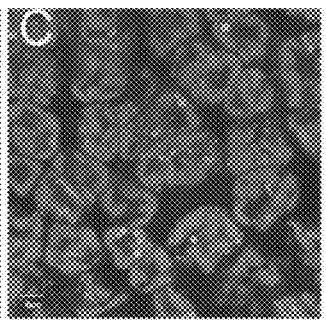
Figure 5A:
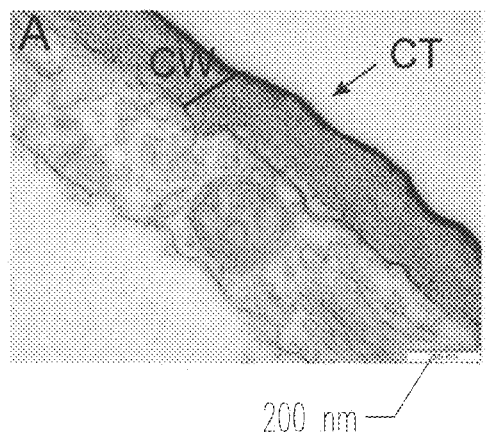
Figure 5B:
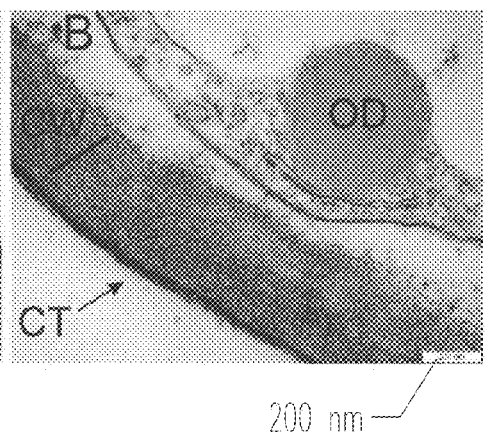
Figure 5C:
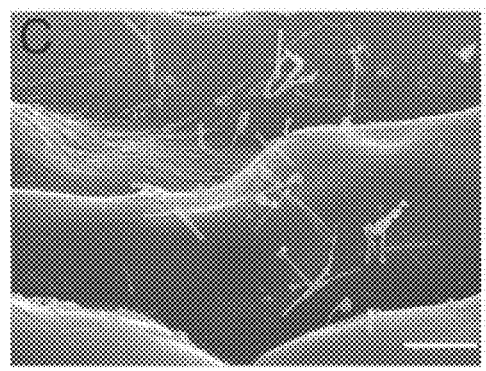
Figure 5D:
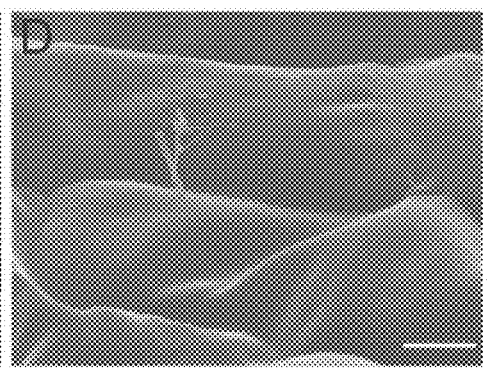
Figure 5E:
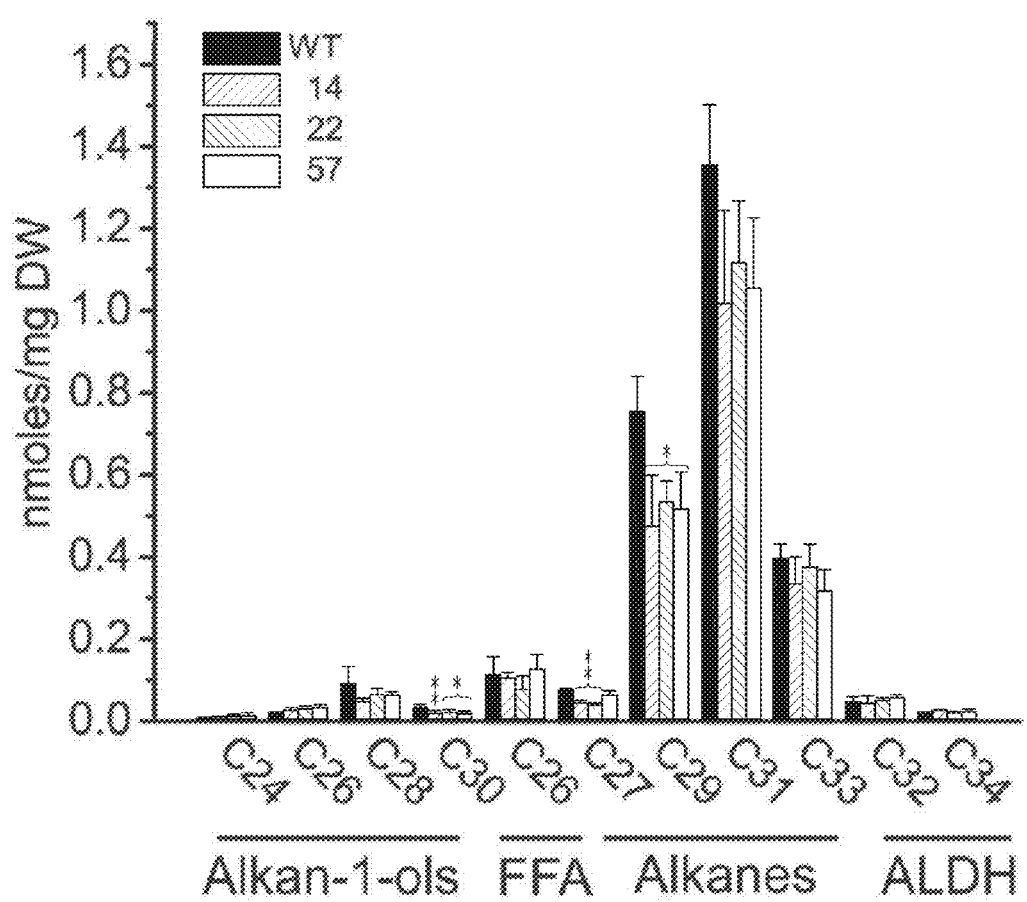
Figure 5F:
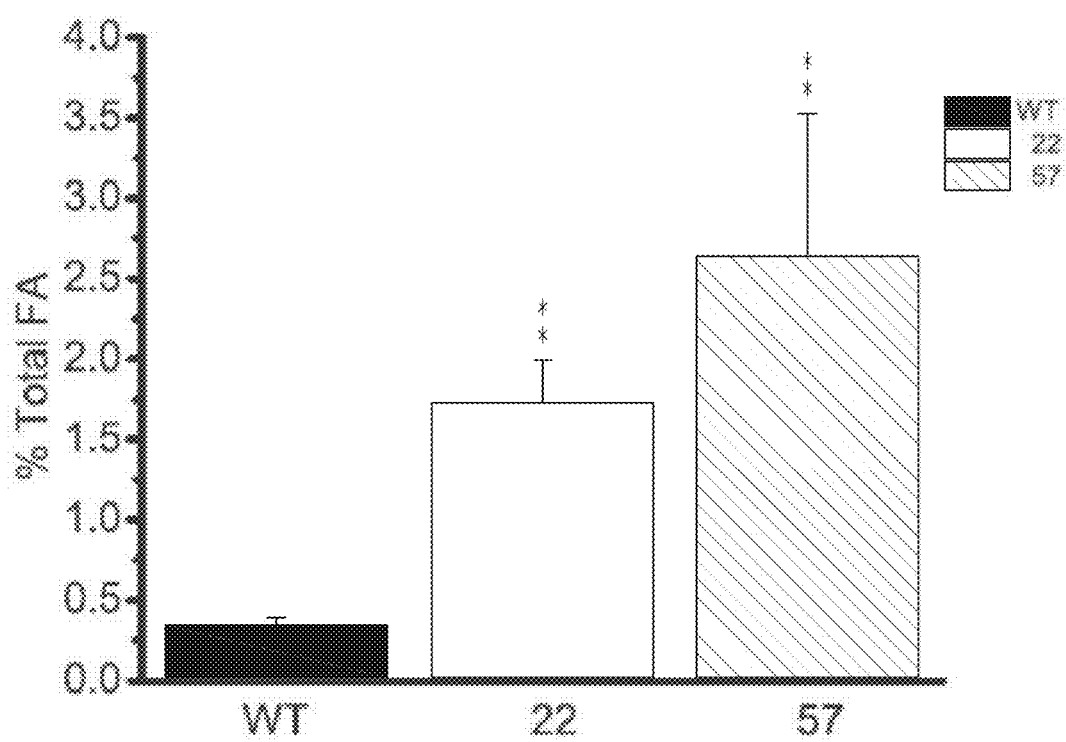
Figure 5C:
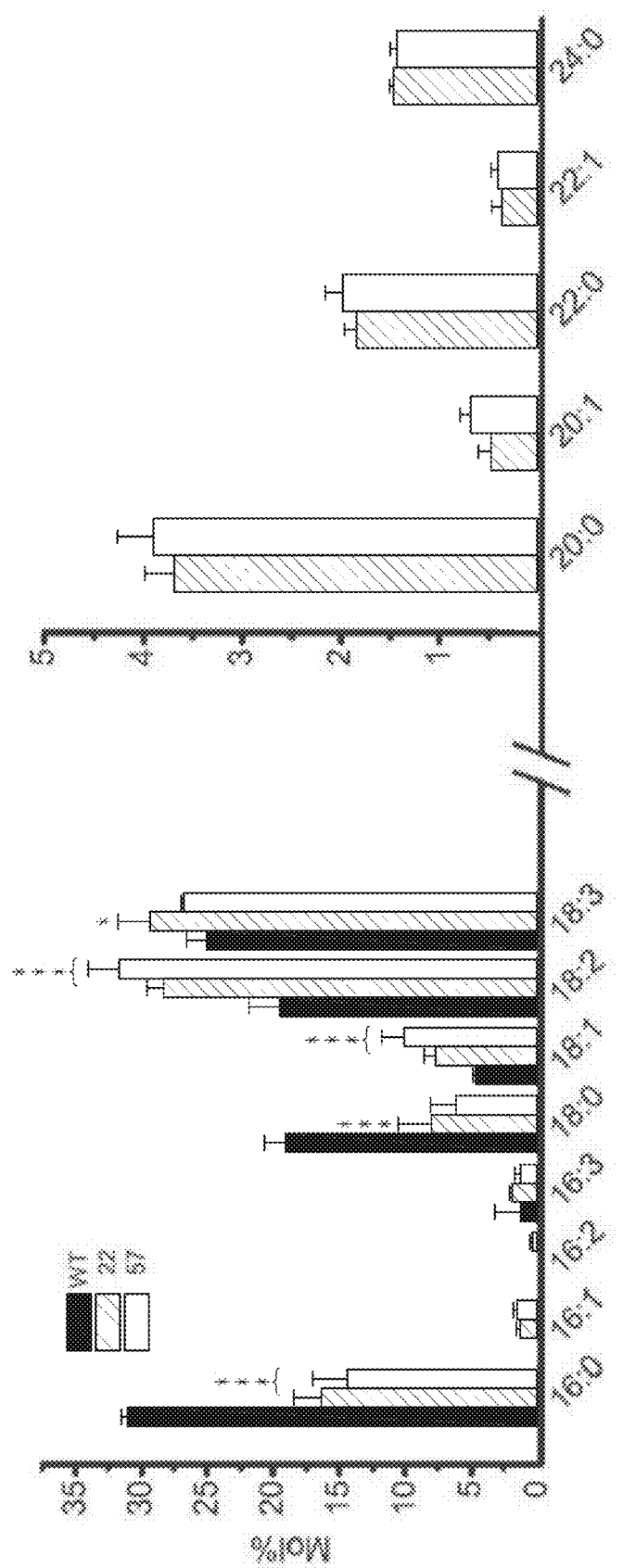

ESI-MS was also used to analyze the TAG content in the leaves of 6-week-old soil-grown plants before bolting. As shown in FIG. 3A, TAG levels in transgenic lines 22 and 57 were 0.23 and 0.36% of dry weight, a 11- and 18-fold increase relative to wild-type plants (0.02% TAG per DW), respectively. These increases were lower than those observed with young seedlings and may reflect turnover of TAG in more mature leaves. The ESI-MS spectrum of neutral lipid extracts from 6-week-old leaves of line 57 confirmed the presence of TAG molecular species containing VLCFAs, which were not detected in the wild type (FIG. 3E-3F). The presence of long and VLCFAs in neutral lipid extracts of soil-grown line 57 was also confirmed by ESI-MS/MS (FIG. 3G). Interestingly, the level of TAGs with VLCFAs (e.g., C24:0) in leaves of soil-grown plants of line 57 was considerably higher (about 8-10 mol %) than wild type (about 2 mol %) (FIG. 4I). Using an independent method, the inventors also confirmed the levels of TAG in transgenic soil-grown plants by transmethylation of TLC-separated TAG and GC-FID analysis of the resulting fatty acid methyl esters (FIG. 5F-5G).

EXAMPLE 8

An Abundance of Oil Droplets in the Leaves of Transgenic Lines

Figure 4D:
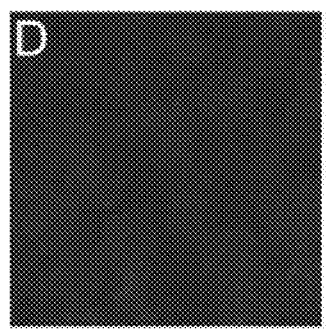
Figure 4E:
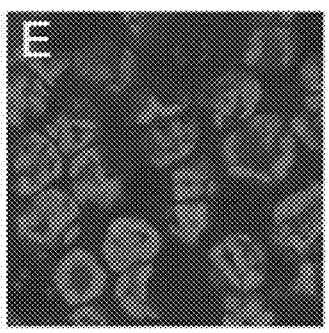
Figure 4F:
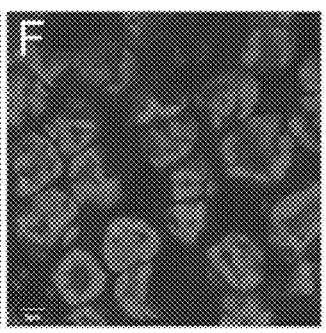

Leaves of 6-week-old TAG-accumulating line 57 and of wild type were compared by confocal microscopy following Nile Red staining and by transmission electron microscopy (TEM). Oil droplets were abundant in line 57 and were distributed in the proximity of the chloroplasts (FIG. 4A, B, C). In contrast, few or no oil droplets were observed in the wild-type leaf sample (FIG. 4D, 4E, 4F).

Figure 4G:
Figure 4H:
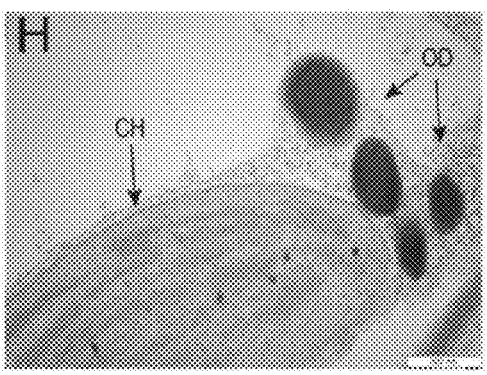

The inventors used TEM to analyze the location of oil droplets in leaf sections. In line 57, large and distinct electron dense oil droplets were observed outside the chloroplast in mesophyll cells, most likely associated with the ER (FIG. 4H). No oil droplets were observed in cells of wild-type sections (FIG. 4G). The shape of chloroplasts and distribution of starch granules were similar in both wild-type and transgenic lines.

EXAMPLE 9

Epidermal Surface Lipids are Reduced in the Transgenic Lines

The inventors suspected that the group of lipids specifically affected by the ectopic accumulation of TAGs with VLCFAs in leaves might be epidermal surface lipids. To test this hypothesis, leaf epidermal cell sections of DGTT2 transgenic line 57 and wild-type plants were examined by TEM. Plants of line 57 had leaves with a noticeably less osmium-dense cuticle than wild type plants (FIG. 5A-5B). Line 57 plants also contained very distinct and large numbers of presumed oil droplets in epidermal and mesophyll cells, including guard cells. Similar oil droplet-like structures were not observed in epidermal cells of wild-type plants. Leaves of transgenic line 57 and wild-type plants were further examined by scanning electron microscopy (SEM) (FIG. 5C-5D). By comparison, line 57 leaves produced relatively fewer rod-like wax crystals on the surface of epidermal cells (FIG. 5D).

To observe quantitative and qualitative changes in wax composition, the rosette leaf waxes of lines 14, 22 and 57 and wild type (6-week-old) were subjected to GC-MS analysis. A considerable change in the wax composition was observed. More specifically a decrease in nonacosane (C29 alkane) was detected that was the most abundant leaf wax constituent, and triacontanol (C30 1-alcohol) in the DGTT2 transgenic lines (FIG. 5E). However, no statistically significant differences were detected between wild type and DGTT2 transgenic lines in the total abundances of waxes (Table 3).

TABLE 3

Total amounts of identified leaf wax and cutin constituents of DGTT2-expressing lines

|  | Wild type | Line 14 | Line 22 | Line 57 |
| --- | --- | --- | --- | --- |
| Wax | 2.91 ± 0.29 | 2.13 ± 0.41 | 2.34 ± 0.30 | 2.28 ± 0.40 |
| Cutin | 5.24 ± 0.17 | 3.25 ± 0.26*** | 3.89 ± 0.31*** | 2.31 ± 0.21*** |

Total leaf wax and cutin are expressed as nmol/mg dry weight;
***significant at $p < 0.001$ compared with wild type (WT) by one-way ANOVA with post hoc Dunnett's test (n = 4; average ± SD).

Figure 6E:
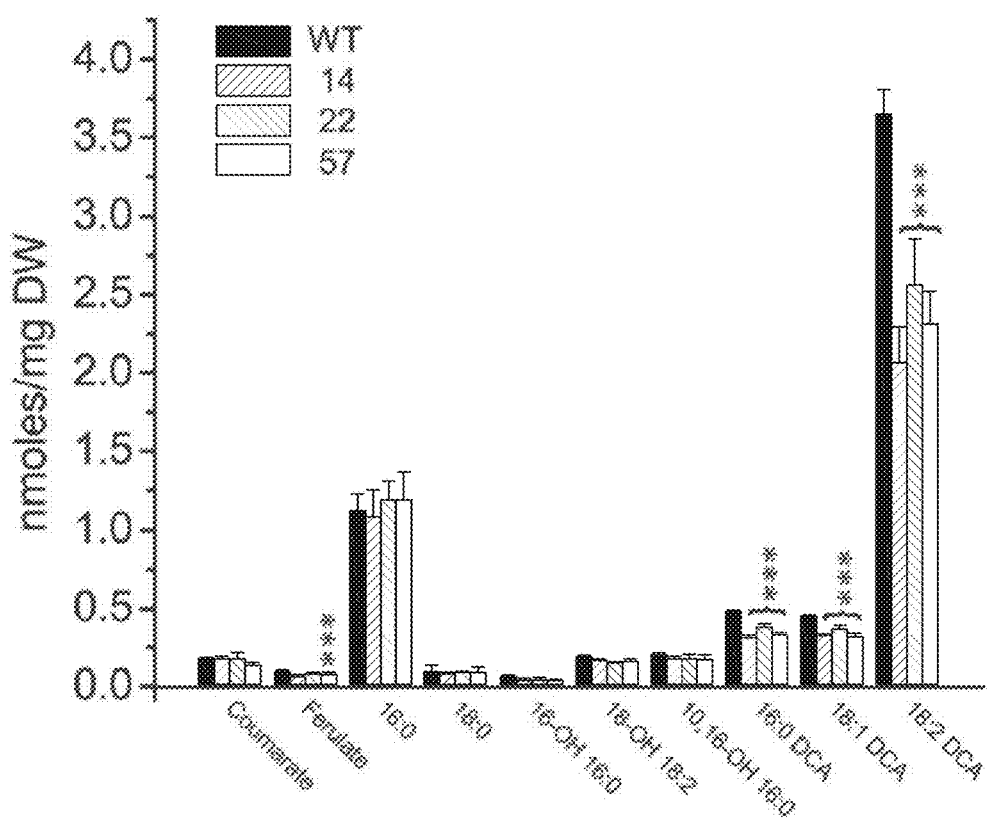
Figure 6G:
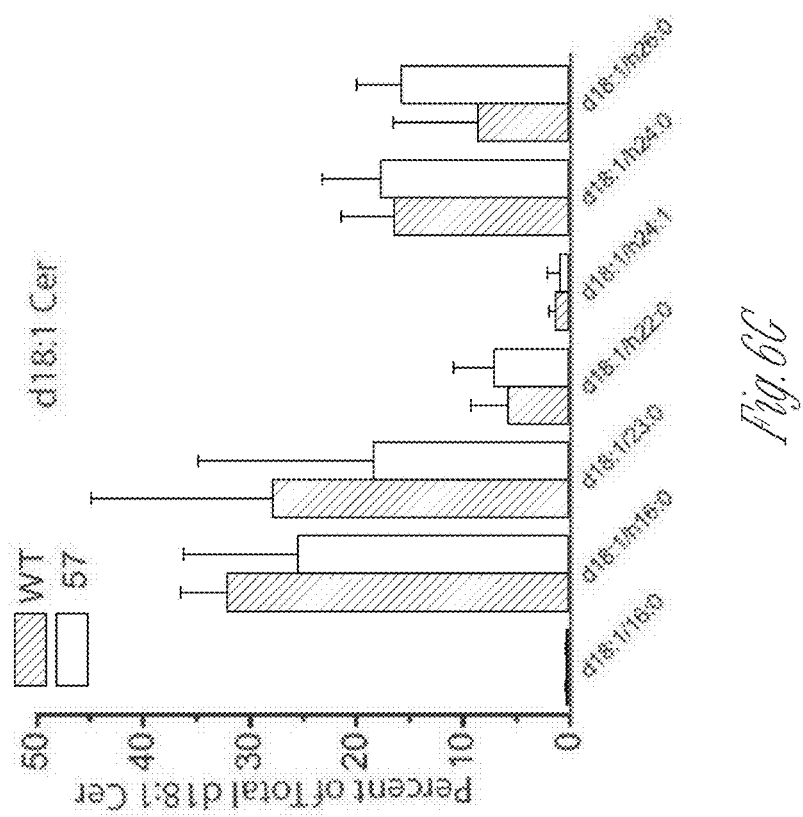
Figure 6F:
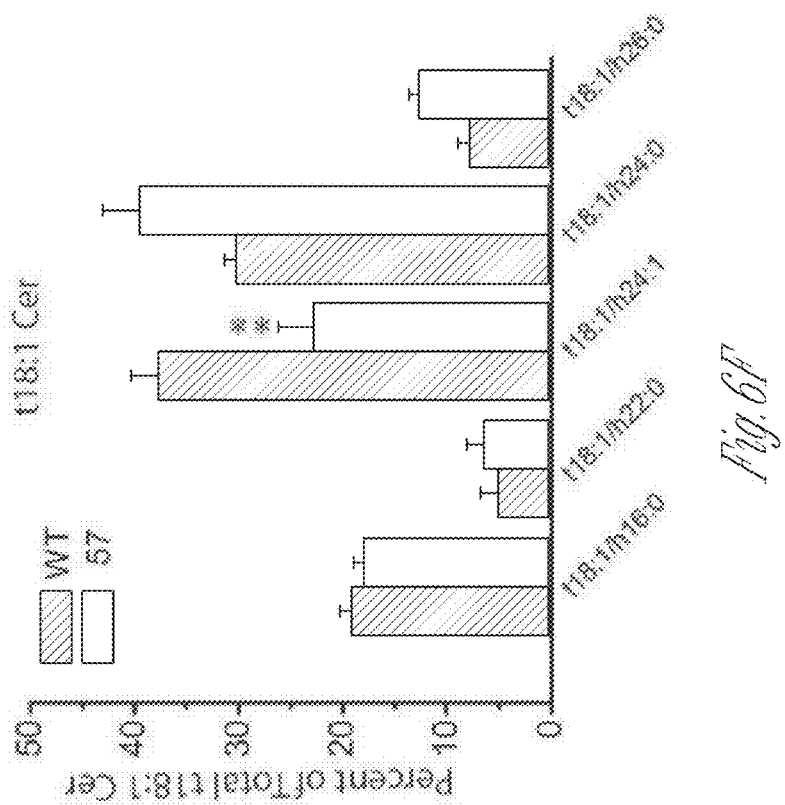
Figure 6I:
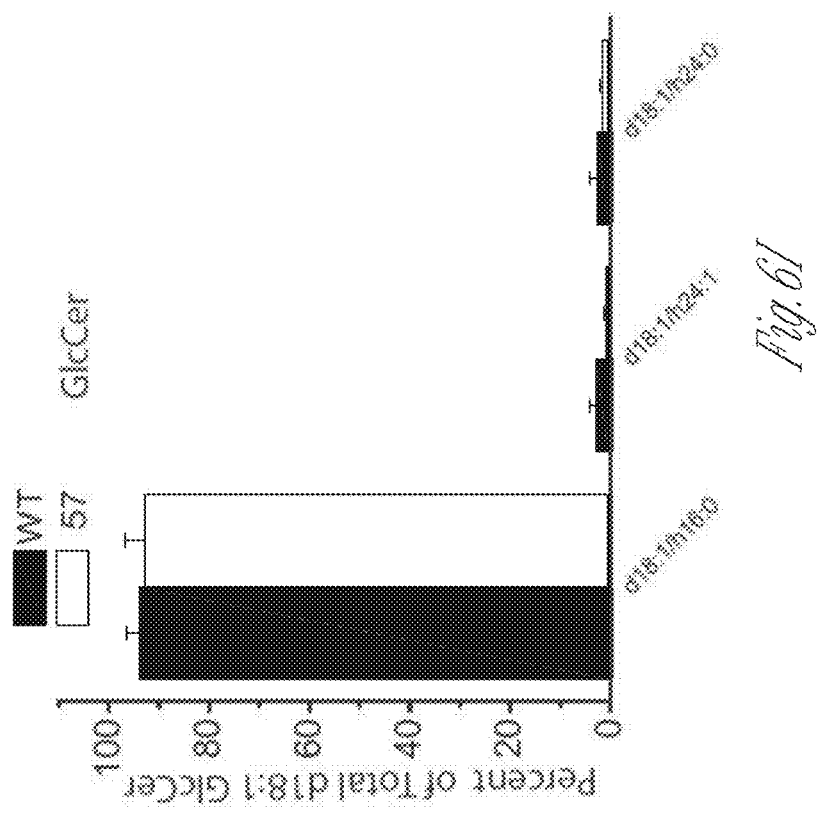
Figure 6H:
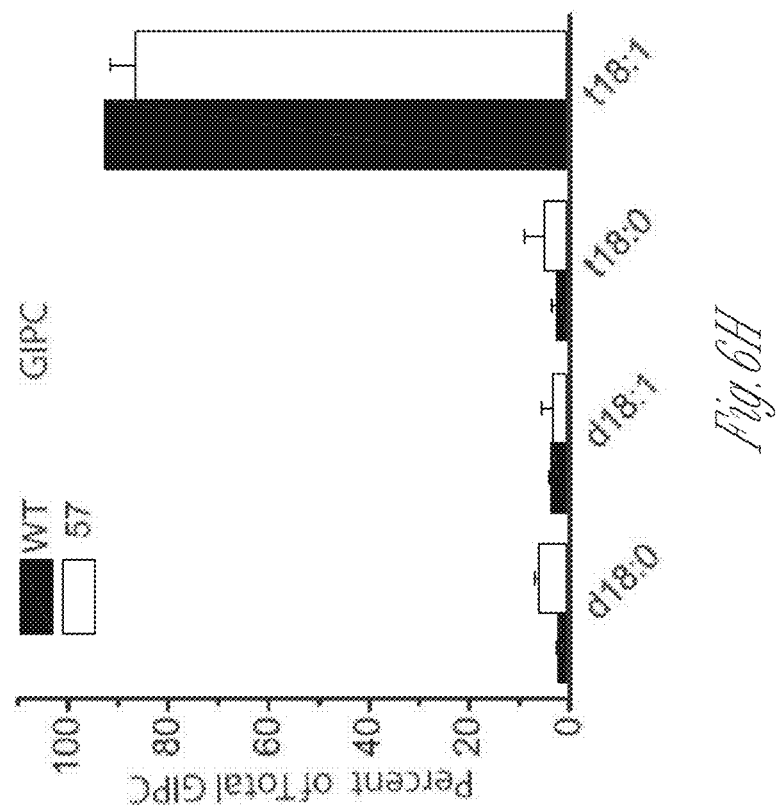

Changes in cutin and cutin-associated features were observed in the transgenic lines. Alteration of cutin content and composition is often associated with changes in the cuticular ledge ultrastructure of guard cells (Kosma & Jenks, Eco-physiological and molecular-genetic determinants of plant cuticle function in drought and salt tolerant crops. In Advances in Molecular Breeding Toward Drought and Salt Tolerant Crops., M. A. Jenks, P. M. Hasegawa, and S. M. Jain, eds (Netherlands: Springer), pp. 91-120 (2007); Li et al., Proc Natl Acad Sci USA 104, 18339-18344 (2007). Stomata of leaves of line 57 and wild type were therefore examined using SEM and TEM. SEM showed that leaves of line 57 had an altered stomatal structure, with wider stomatal openings (FIGS. 6A-6B). TEM images revealed smaller and thinner cuticular ledges in guard cells of line 57 (FIGS. 6C-6D). These observations led us to investigate leaf cutin monomer composition. Ectopic production of DGTT2 resulted in a 25-37% reduction in total-identified cutin monomer content (Table 3). In particular, the α,ω-dicarboxylic acid (DCA) content of DGTT2-transgenic lines was lower, with slight reductions in 16:0 DCA and 18:1 DCA amounts (22-37% and 18-30% reductions, respectively p<0.001, n=4) and particularly large reductions in 18:2 DCA content (30-44% reduction p<0.001, n=4; FIG. 6E).

EXAMPLE 10

Composition of Sphingolipids are Altered in DGTT2 Lines

Figure 7A:
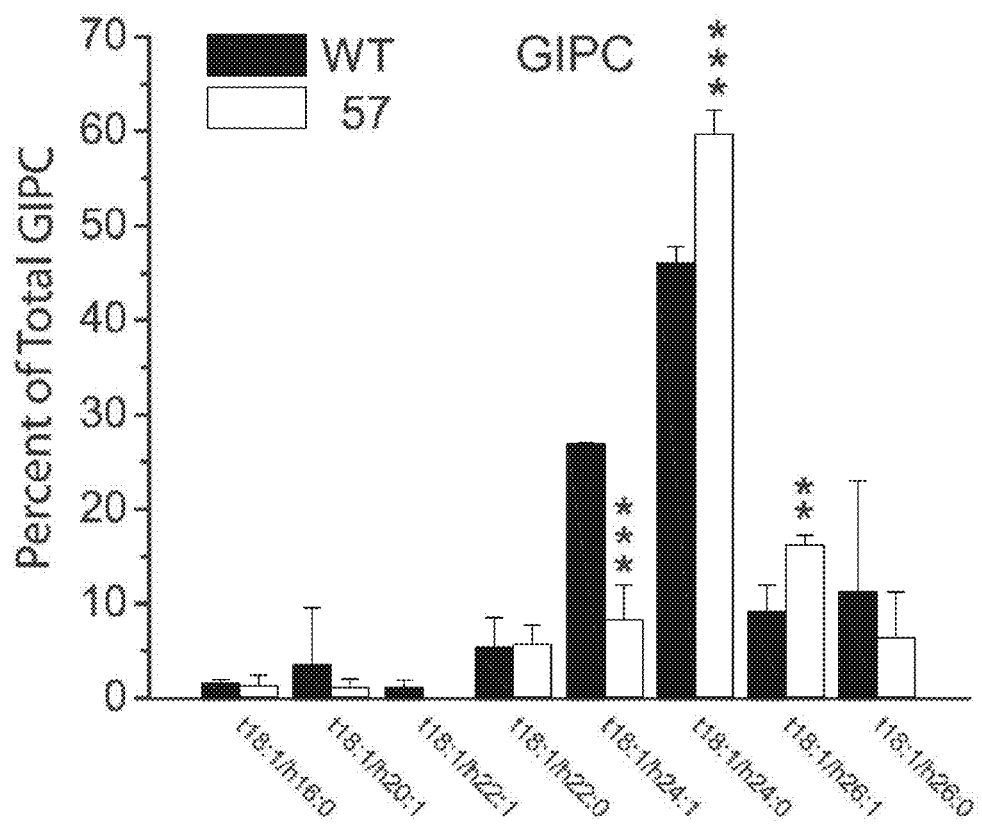

DGTT2 accepts a broad range of acyl-CoA substrates. However, expression of DGTT2 could result in reduced sphingolipid content in the leaves. The inventors analyzed sphingolipid content in wild type and transgenic lines using ESI-high resolution/accurate mass spectrometry to identify glycosyl inositolphosphoceramide (GIPC) lipids. Normalization of GIPC lipid abundances against an internal standard (d18:1/12:0 lactosyl ceramide) demonstrated that in wild-type plants the t18:1/h24:0 and t18:1/h24:1 molecular species were the most abundant (FIG. 7A), constituting 46.2%±1.65% and 19.5%±12.8% of all GIPC lipids respectively. Notably, line 57 (FIG. 7A) exhibited 29.5% and 76.6% increases in levels of t18:1/h24:0 GIPC (p<0.001, n=3) and t18:1/h26:1 (p<0.01, n=3) relative to wild-type plants, respectively, and a concomitant 56.7% decrease in the level of t18:1/h24:1 GIPC (p<001, n=3). These data suggest that DGTT2 production in the leaves of transgenic plants reduces 24:1 fatty acid content in GIPC lipids, while enriching the GIPC content of 24:0.

Figure 7B:
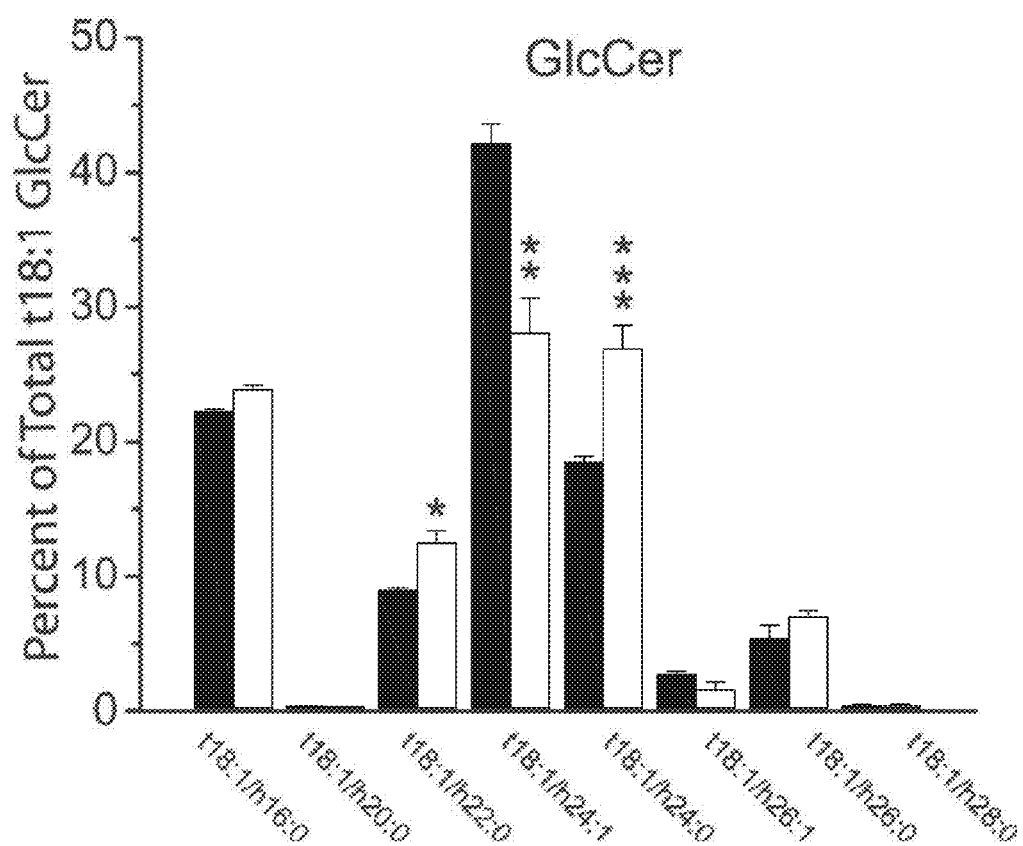

To determine whether DGTT2-dependent modulation of sphingolipid 24:1 and 24:0 fatty acid levels was specific to GIPC lipids or distributed across other sphingolipid classes, the less abundant glucosylceramide (GlcCer) and ceramide (Cer) lipids were also analyzed. As shown in FIG. 7B, the presence of DGTT2 altered the content of t18:1 GlcCer lipids, as line 57 exhibited 39.8% (p<0.01, n=3) and 46.1% (p<0.01, n=3) higher levels of h22:0 and h24:0 fatty acids, respectively, compared to wild type. As observed for the GIPC lipids, h24:1 species of t18:1 GlcCer were reduced in the line 57 by 33.5% (p<0.01, n=3) relative to wild type. Only three molecular species of d18:1 GlcCer were detected (FIG. 6I), which contained h16:0, h24:0, and h24:1 fatty acids. Additionally, line 57 also contained 39.3% decreased levels (p<0.01, n=3) of h24:1 fatty acid in t18:1 Cer relative to wild type (FIG. 6F), while h26:0 increased 66%. However, no statistically significant differences were detected between wild type and line 57 in the total abundances of these lipids (FIG. 6F-I). Together, these results indicate that decreases in C24:1 of sphingolipids reflect channeling of VLCFAs into TAG (FIG. 3D, 3G).

EXAMPLE 11

Limited Changes in Global Expression of Genes in DGTT2 Lines

To evaluate possible compensatory mechanisms in the transgenic lines, microarray experiments were conducted with RNA extracts from the leaves of 6-week-old soil-grown plants. A two factor mixed model ANOVA analysis was employed to account for the effects of genotype and chip, and P values were calculated for the wild type vs. line 57. Since no meaningful hits could be identified after a false discovery rate correction, 15 genes were selected using the unadjusted p value threshold of <0.002 and fold change>2 or <−2 (Table 4).

TABLE 4

Differentially expressed genes identified in DGTT2 plant lines and wild type plants using NimbleGen microarray analysis at a p value threshold of <0.002 and fold change >2 or <−2

| Probeset ID | Gene name | Description (Arabidopsis.org) | p-value (57 vs. WT) | stepup FDR (57 vs. WT) | Log2 (Ratio T) 57 vs. WT | Fold-Change (57 vs. WT) |
|---|---|---|---|---|---|---|
| AT5G35935.1 | N/A | Transposable element gene | 4.06E−07 | 0.00739889 | 5.7343 | 53.2348 |
| AT4G10690.1 | N/A | Transposable element gene | 1.84E−05 | 0.167326 | 2.18811 | 4.55707 |
| AT5G37300.1 | AT5G37300 | Wax ester synthase (WS) and diacylglycerol acyltransferase (DGAT) | 0.00031769 | 0.35823 | 1.9511 | 3.86669 |
| AT3G30720.1 | AT3G30720 | QUA-QU1NE STARCH | 0.00019769 | 0.35823 | 1.88535 | 3.69443 |
| AT5G52390.1 | AT5G52390 | PAR1 protein | 0.0001984 | 0.35823 | 1.57068 | 2.97045 |
| AT4G15210.1 | AT4G15210 | ATBETA-AMY | 0.00197562 | 0.444417 | 1.51976 | 2.86743 |
| AT4G08300.1 | AT4G08300 | Nodulin MtN21/EamA-like transporter family protein | 0.00162795 | 0.423754 | 1.41472 | 2.66608 |
| AT1G65450.1 | AT1G65450 | HXXXD-type acyl-transferase family protein | 0.00086168 | 0.405123 | 1.18481 | 2.27334 |
| AT2G37390.1 | AT2G37390 | Chloroplast-targeted copper chaperone protein | 0.0007635 | 0.405123 | 1.1454 | 2.21208 |
| AT5G58390.1 | AT5G58390 | Peroxidase superfamily protein | 0.00010327 | 0.316785 | 1.03803 | 2.05342 |
| AT3G46250.1 | N/A | Pseudogene | 0.00045219 | 0.35823 | −1.01506 | −2.02099 |
| AT2G23210.1 | AT2G23210 | UDP-Glycosyltransferase superfamily protein | 0.00010156 | 0.316785 | −1.17768 | −2.26213 |
| AT2G06740.1 | N/A | Transposable element gene | 0.00113698 | 0.405123 | −1.19879 | −2.29548 |
| AT3G28917.1 | AT3G28917 | MINI ZINC FINGER 2 | 0.00037374 | 0.35823 | −1.22747 | −2.34156 |
| AT5G29034.1 | N/A | Transposable element gene | 0.0010216 | 0.405123 | −1.57872 | −2.98705 |

Of the 15 genes selected from the microarray study, 10 were up-regulated and 5 down-regulated (Table 5).

TABLE 5

Changes in the gene expression in the leaves of DGTT2 plants.

| Locus | Gene Name | Annotation | Functional Category | Fold Change |
|---|---|---|---|---|
| Up-Regulated | | | | |
| At5g37300 | WSD1 | wax ester synthase (WS) and diacylglycerol acyltransferase (DGAT) | Lipid metabolism | 3.86 |
| At3g30720 | | Qua-Quine Starch (QQS) | Starch metabolism | 3.69 |
| AT4g15210 | ATBETA-AMY | Cytosolic beta-amylase expressed in rosette leaves and inducible by sugar | Starch metabolism | 2.86 |
| At1g65450 | | HXXXD-type acyl-transferase family protein | Lipid metabolism | 2.27 |
| AT2g37390 | NSKR2 | Sodium potassium root defective 2 | Metal ion binding | 2.21 |
| AT5g58390 | | Peroxidase superfamily protein | Peroxidase activity | 2.05 |
| AT5g52390 | | PAR1 protein | Unknown | 2.97 |
| AT4g08300 | | Nodulin Mt-N21/EamA-like transporter family protein | Unknown | 2.66 |
| Down-Regulated | | | | |
| At3g28917 | MIF2 | mini zinc finger 2 | DNA binding, biological process unknown | −2.34 |
| At2g23210 | | UDP-Glycosyltransferase superfamily protein | transferase activity | −2.26 |

Two up-regulated genes were predicted to encode enzymes with a known involvement, or a possible involvement, in TAG biosynthesis, including a bifunctional enzyme WSD1 (wax ester synthase and diacylglycerol acyltransferase), At5g37300 (Li et al., Plant Physiol 148, 97-107 (2008) and a gene encoding an HXXXD-type acyl-transferase, At1g65450. The inventors also identified changes in expression of the qua-quine starch (QQS) regulatory gene, At3g30720, and cytosolic beta-amylase encoding gene, At4g15210. Both proteins are involved in starch metabolism (Li et al., Plant J 58, 485-498 (2009). One of the down-regulated genes with unknown function was predicted to encode a mini zinc finger protein, At3g28917, and another a UDP-glycosyltransferase, superfamily protein, At2g23210.

To validate the microarray analysis, the transcript levels of the four genes were quantified relevant to oil biosynthesis and starch metabolism, using q-RT-PCR. For this experiment RNA was isolated from an independent set of wild-type and line 57 plants. When normalized to wild-type values, the transcript levels for the WSD1-encoding gene were 3.5-fold higher, for the HXXXD-type acyl-transferase protein-encoding gene 4.4-fold, for the QQS gene 4.3-fold, and for the cytosolic beta-amylase-encoding gene 3.0-fold elevated in line 57, thus confirming the microarray results (see FIG. 8C-8F).

EXAMPLE 12

Ectopic Production of DGTT2 Results in TAG Accumulation in *Arabidopsis*

As explained above, most of the DGTT2-producing *Arabidopsis* lines examined developed distinct seedling phenotypes, such as accelerated hypocotyl elongation and pale green cotyledons. The increased hypocotyl length may be due to excess storage compounds such as TAG in the seeds that may accelerate cell elongation compared to wild type. The reduction in chlorophyll content in the DGTT2 seedlings may be related to the reduction in the major plastid lipids, limiting the extent of the photosynthetic membrane. The fact that this phenotype is only visible at the seedling stages, when leaves need to rapidly expand and when demands on membrane lipid biosynthesis are high, supports this hypothesis. The acyl-group supply may be limited and TAG accumulation in leaves diverts acyl groups away from other pathways, such as plastid glycerolipid biosynthesis, without a compensatory increase in acyl synthesis. This hypothesis is supported by the microarray results, which revealed no significant induction of genes encoding enzymes necessary for fatty acid biosynthesis (Tables 4 and 5).

In general, plants accumulate TAG in seeds as stored energy that can be subsequently used to fuel germination and seedling establishment. As demonstrated herein accumulation of TAG with VLCFA, such as C20:0 and longer, in green seedlings and leaves of soil grown plants can be achieved by expression of DGTT2, even though VLCFA-containing glycerolipids do not normally accumulate in green tissues of *Arabidopsis*. This observation was unexpected because *Chlamydomonas* TAG primarily contains C16:0 and C18:1 fatty acids, but no TAG species containing VLCFAs (Fan et al., 2011). Following the ectopic production of DGTT2 in the leaves of *Arabidopsis*, most likely the availability of particular acyl-CoA species as well as the substrate preference of DGTT2 for VLCFAs leads to the observed composition of the TAG produced in the transgenic lines. It is interesting to note that the amount of TAG accumulated in DGTT2 transgenic seedlings was higher than that of soil grown plants (FIG. 7G), while the relative abundance of major chloroplast lipids such as MGDG and DGDG was reduced (FIG. 7G-7K). These seedlings had increased levels of 16:3-containing molecular species of MGDG but fewer 18:3-containing species, similar to mutants affected in ER-to-plastid lipid trafficking (Xu et al., EMBO J 22, 2370-2379 (2003)), suggesting that fatty acid intermediates normally transported from the ER to the chloroplast as part of the eukaryotic pathway of thylakoid lipid biosynthesis are instead channeled into TAG. Compared to seedlings, the lower levels of TAG that accumulated in the leaves of soil-grown DGTT2 transgenic plants may perhaps be explained by fatty acid catabolism in older leaves (Yang and Ohlrogge, Plant Physiol 150, 1981-1989 (2009)).

EXAMPLE 11

Growth, Starch and Heating Value of DGTT2 Lines

Figure 8A:
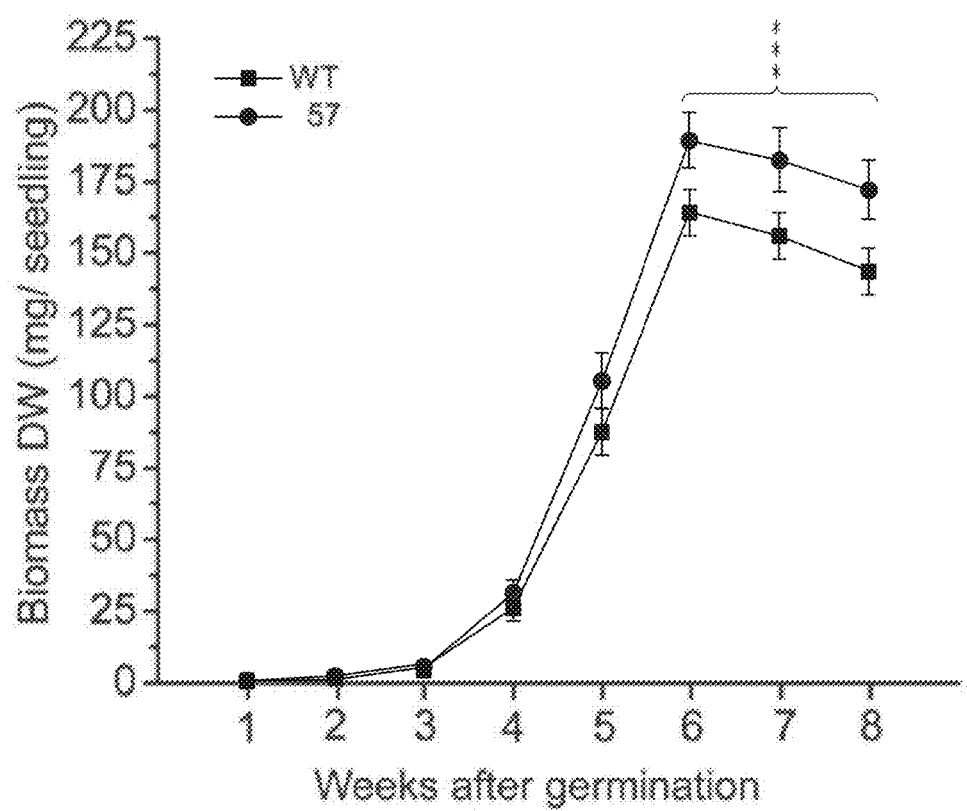

The dry weight of the aerial parts of soil-grown transgenic line 57 and wild-type plants was measured on a weekly basis. The overall morphology of the leaves and shoots from the DGTT2 transgenic line was unchanged. Transgenic line 57 gained a considerably higher biomass than wild type (105.6 and 87.6 mg DW per seedling, p<0.001, n=3) during the first 5 weeks after germination and DW values continued to be higher until the end of the experiment (FIG. 8A). The growth rate of transgenic line 57 and wild-type plants slowed after the $8^{th}$ week.

Figure 8B:
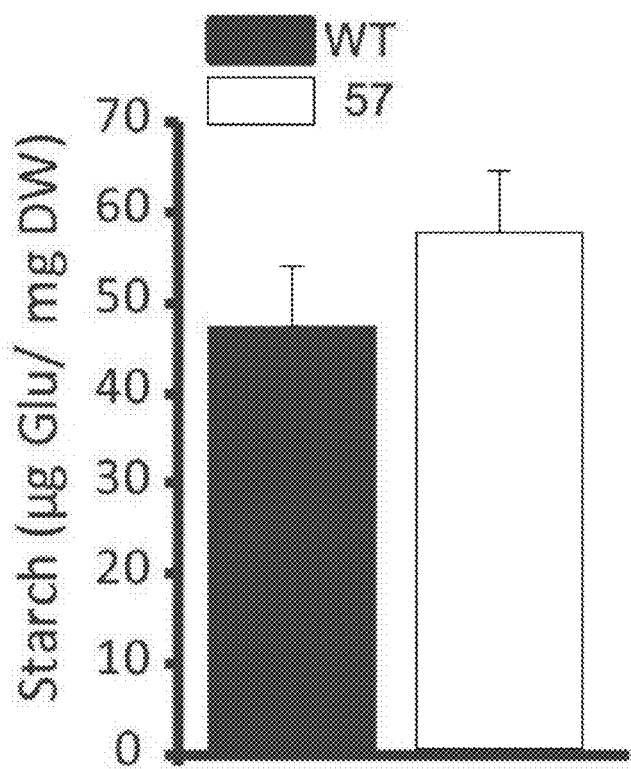
Figure 8C:
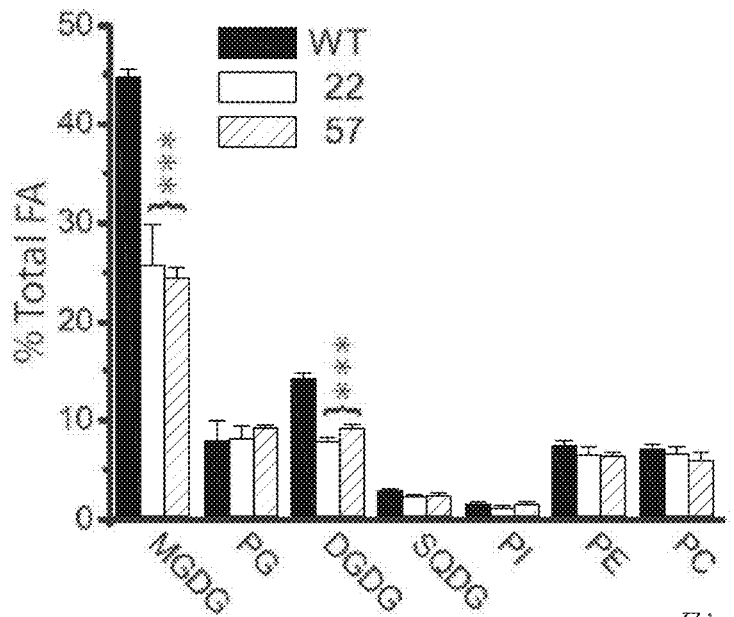
Figure 8D:
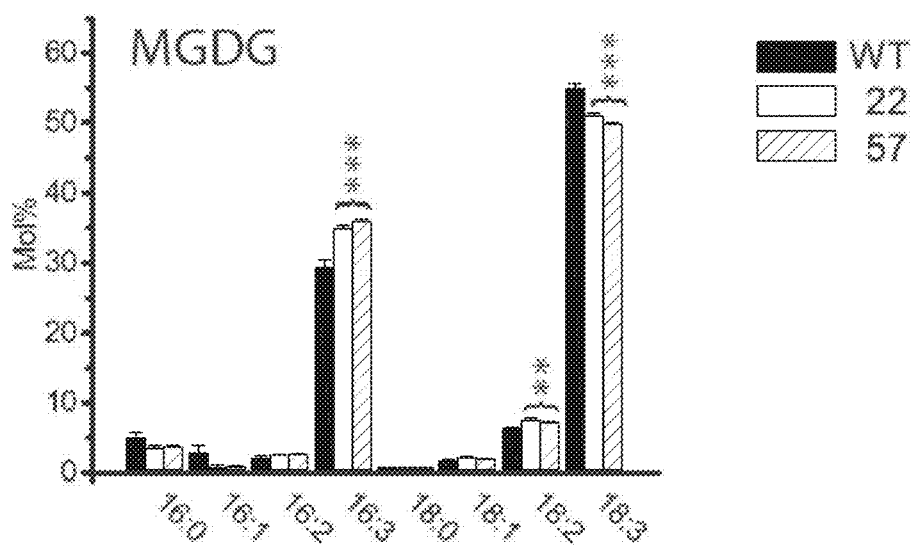
Figure 8E:
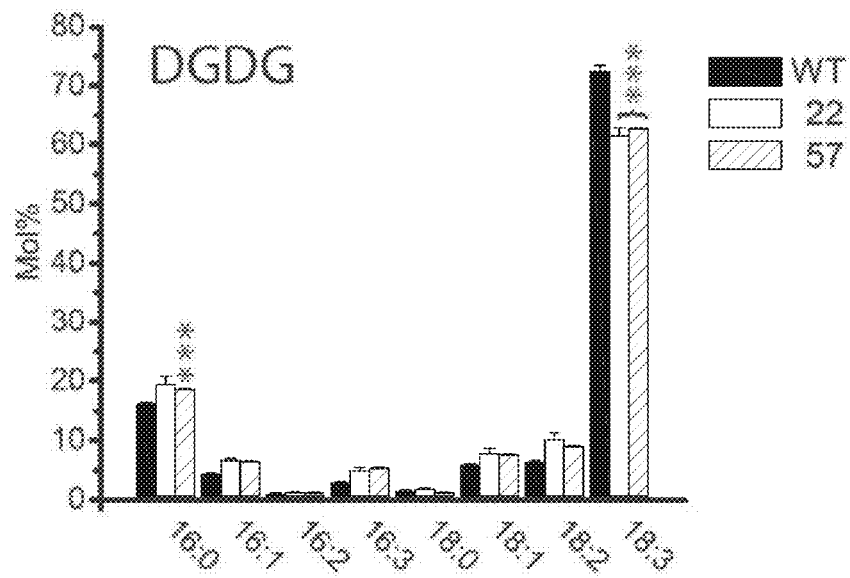
Figure 8F:
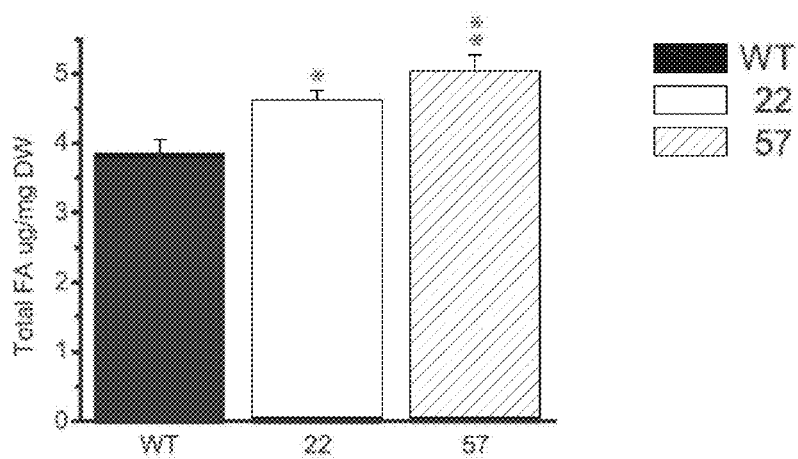
Figure 8C:
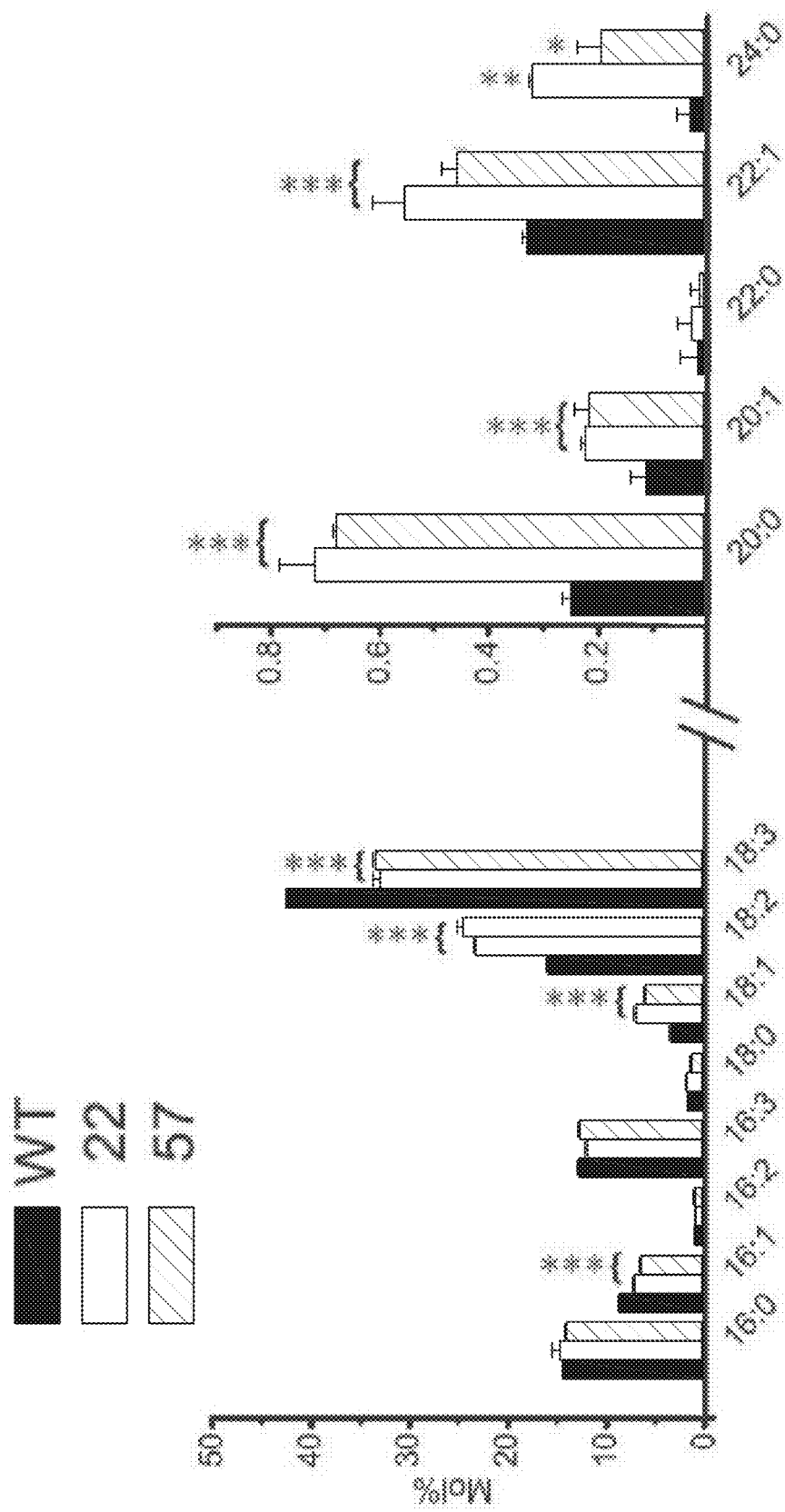

The increased transcript levels of the QQS gene and cytosolic beta-amylase encoding gene in transgenic line 57 from the microarray experiments led us to investigate the starch content of DGTT2-transgenic plants. Contrary to expectation, given the increase in the expression of the genes encoding QQS and beta-amylase, six-week-old plants of line 57 accumulated 18.7% more starch than wild-type plants (58.0 and 47.1 µg Glu per mg DW (p<0.01, n=5), respectively) (FIG. 8B). Heating values were calculated for 6-week-old line 57 and wild-type plants based on an elemental analysis of dry biomass in the presence of oxygen. Consistent with the increase in fatty acid content, a slight increase was observed for line 57 (14.1±0.2 MJ/kg DW, compared to wild type 13.9±0.4 MJ/kg DW; see Table 2), but this difference was not statistically significant.

EXAMPLE 12

Caterpillars Feeding on DGTT2 Lines Gained More Weight

Figure 9A:
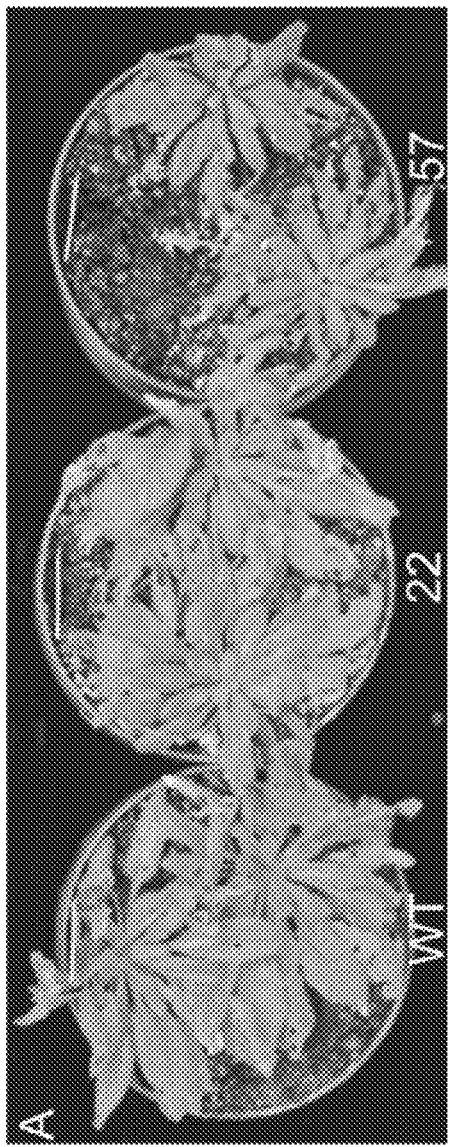
FIG. 9A-9I illustrates results of *Spodoptera exigua* feeding assays and assessment of the 18:3-derived phytohormone, jasmonoyl-L-isoleucine (JA-Ile).
Figure 9B:
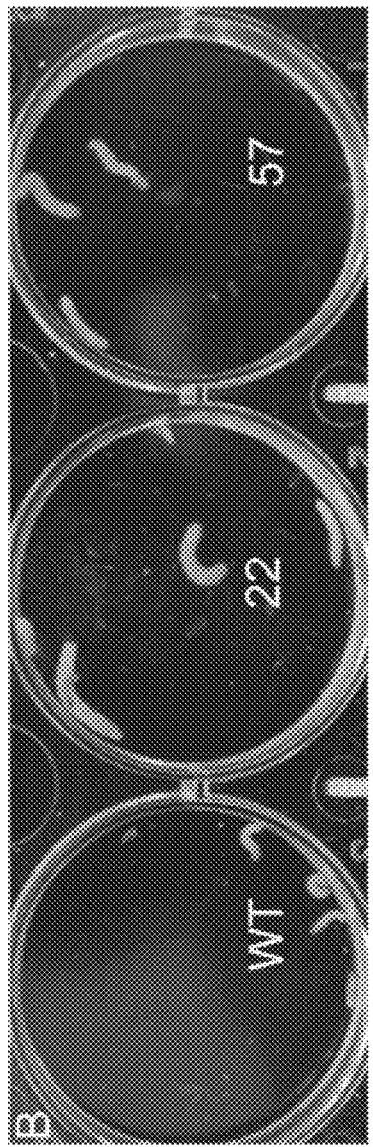
Figure 9C:
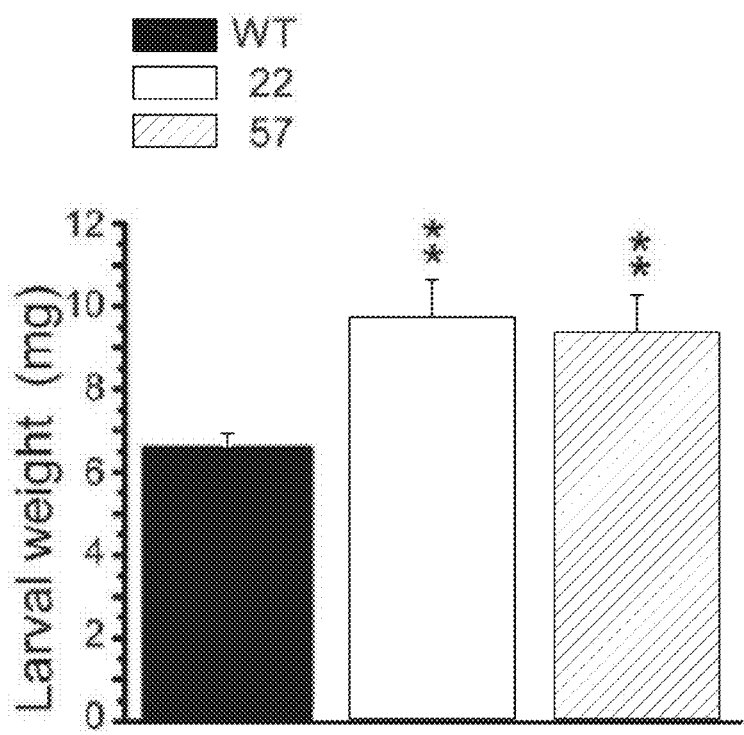

Increased TAG accumulation or decreased wax and cutin in vegetative tissue may result in an unusual diet for phytophagous organisms and may perhaps affect the nutritional value of the plants. To test this hypothesis, the inventors conducted a "no choice" insect-feeding assay, in which the generalist lepidopteran herbivore *Spodoptera exigua* was reared on wild type and transgenic lines 22 and 57 (FIGS. 9A-9B). Newly hatched larvae were caged in pots containing 6-week-old plants of either two transgenic lines (22 and 57) or wild type and were allowed to feed and grow for 14 days. At the end of the feeding trial, larvae were recovered and their body mass was determined. No visible difference in plant consumption was observed between DGTT2-producing lines and wild type during the 14 day trial (FIG. 9A). However, insects grown on DGTT2-producing lines were heavier (9.75±3.42 mg larval weight) than larvae reared on wild-type plants (6.57±1.39 mg larval weight) (p<0.01, n=90; FIGS. 9B and 9C).

Figure 9D:
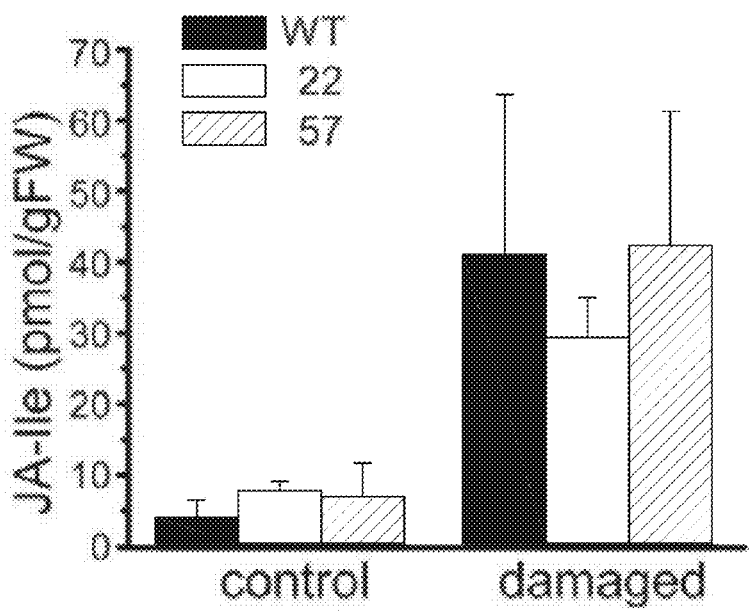
Figure 9E:
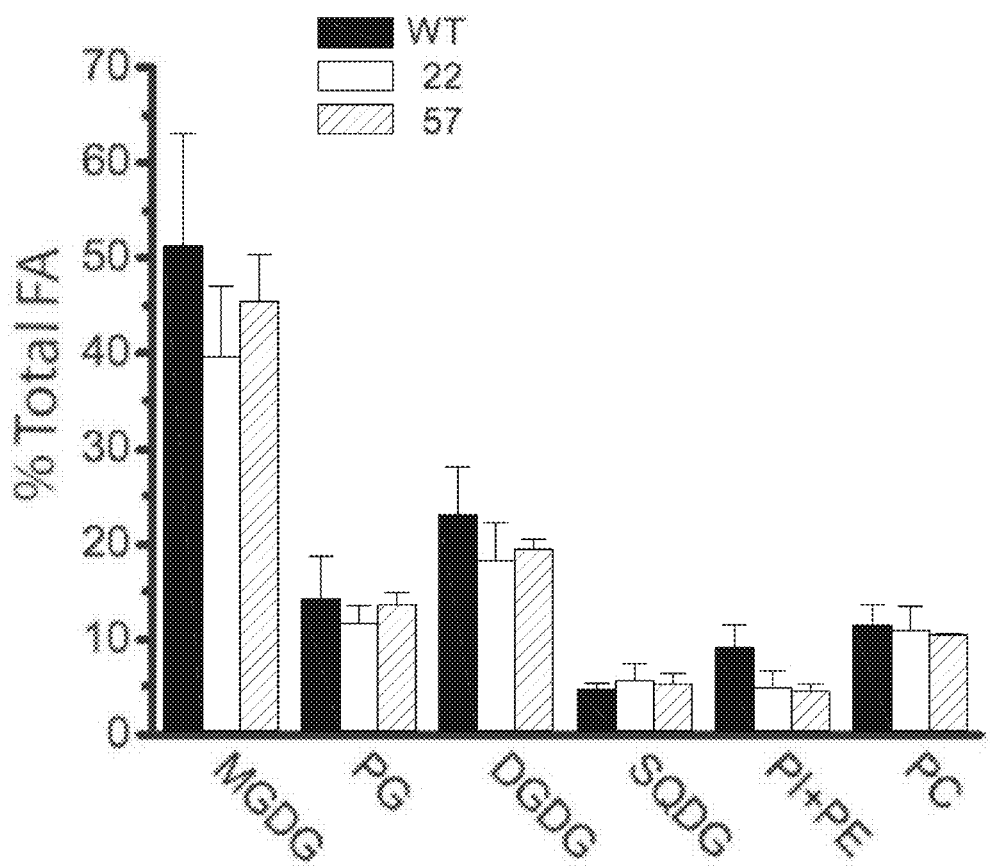
Figure 9F:
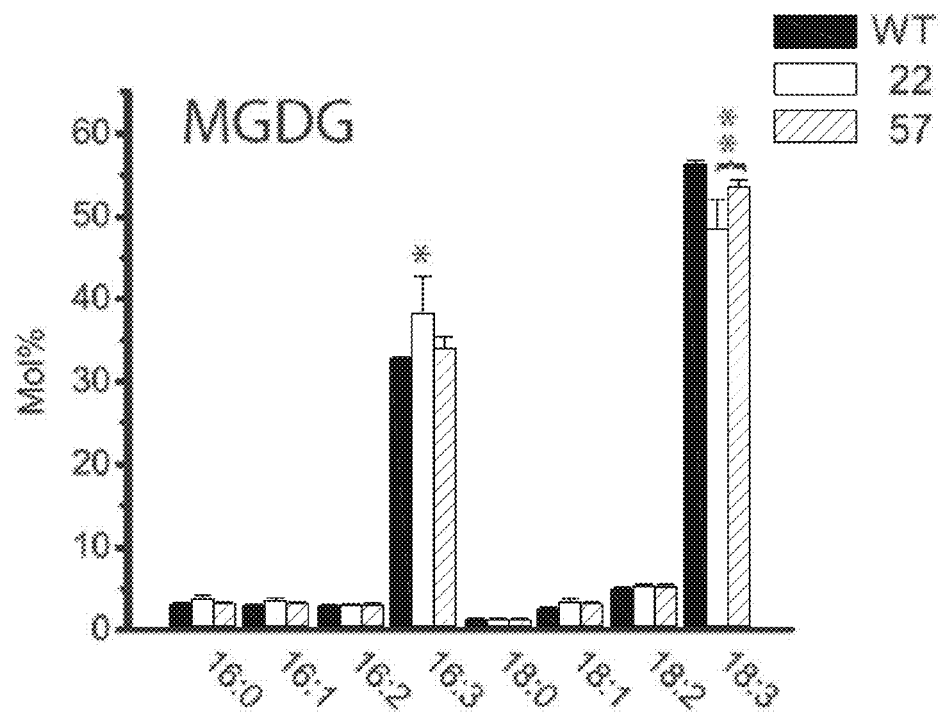
Figure 9G:
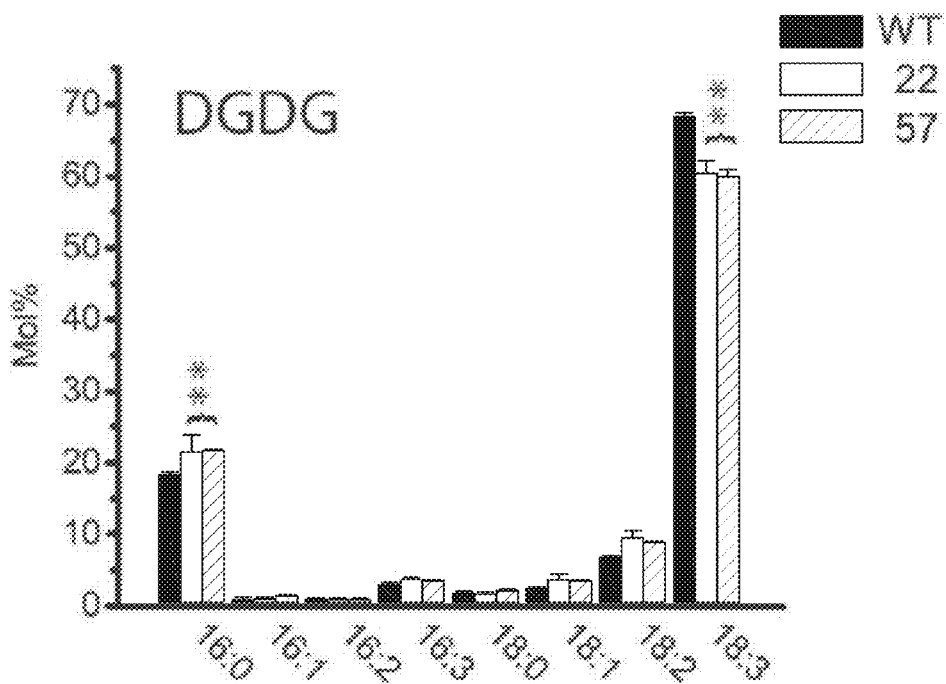
Figure 9H:
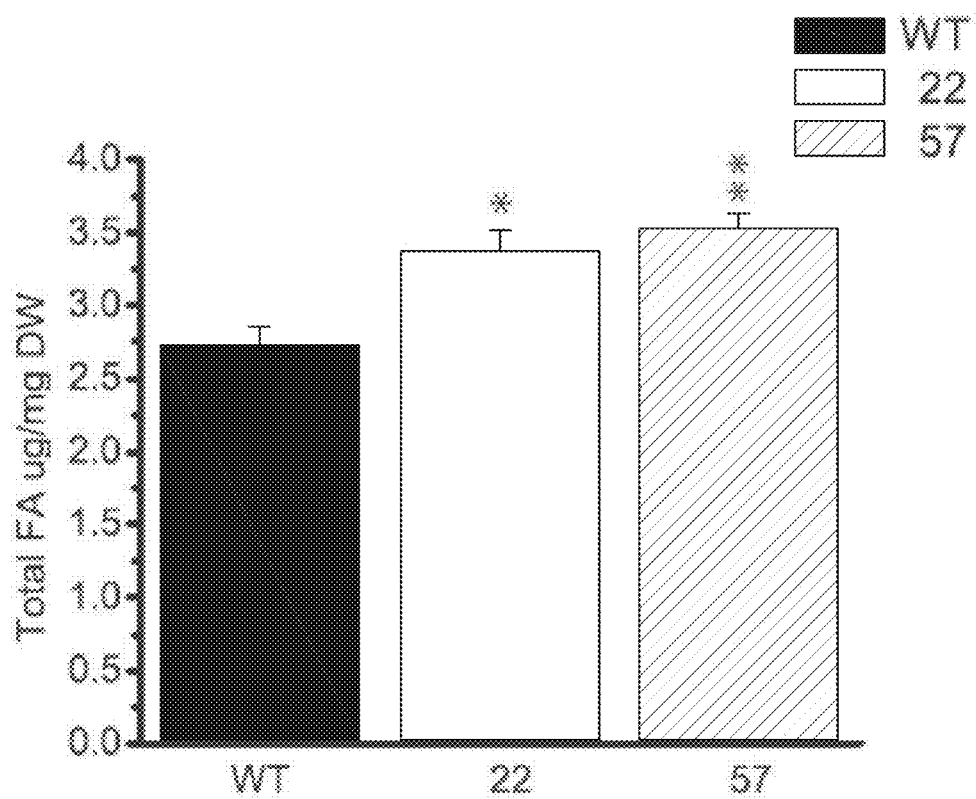
Figure 9I:
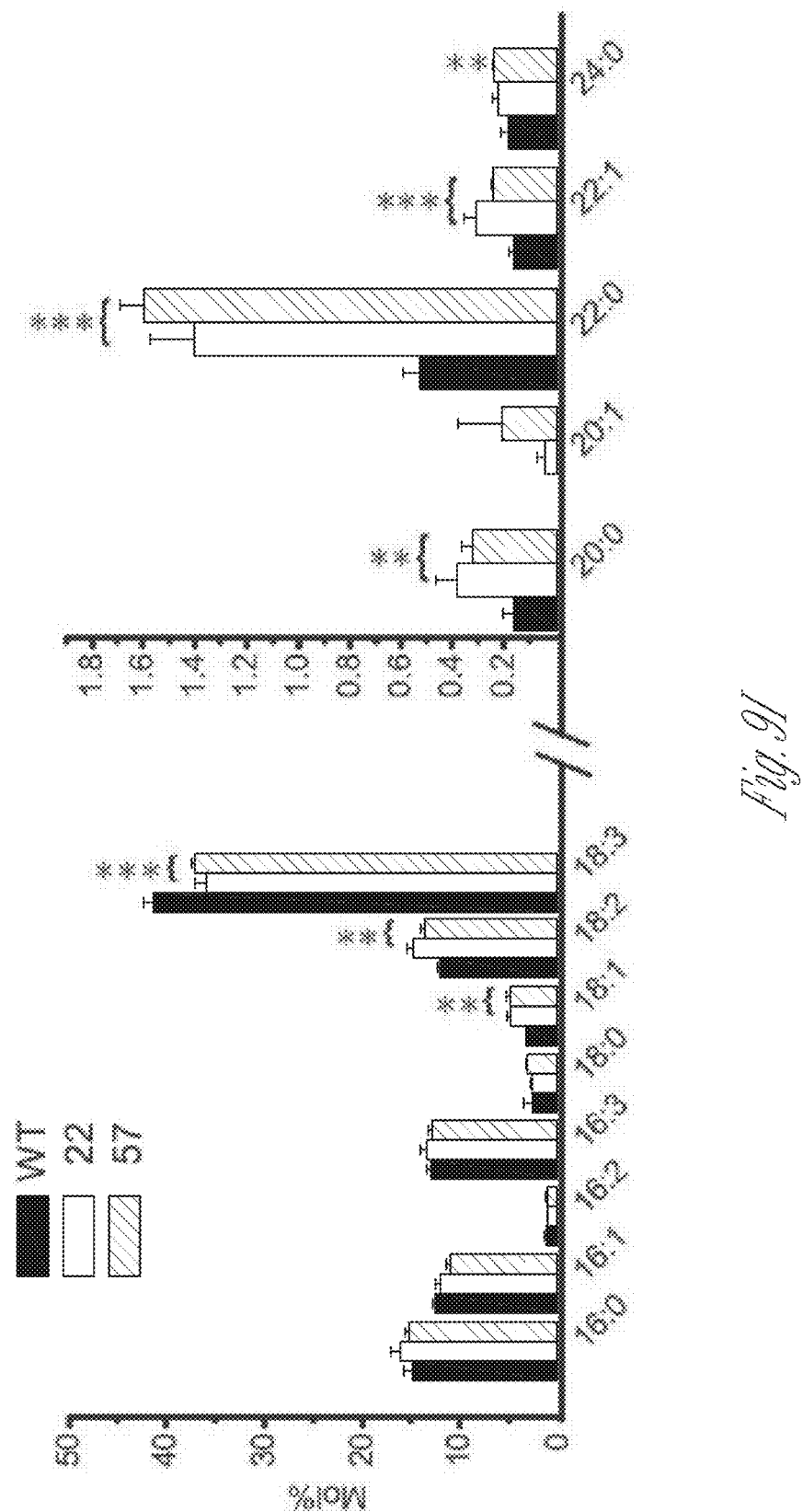
Figure 10A:
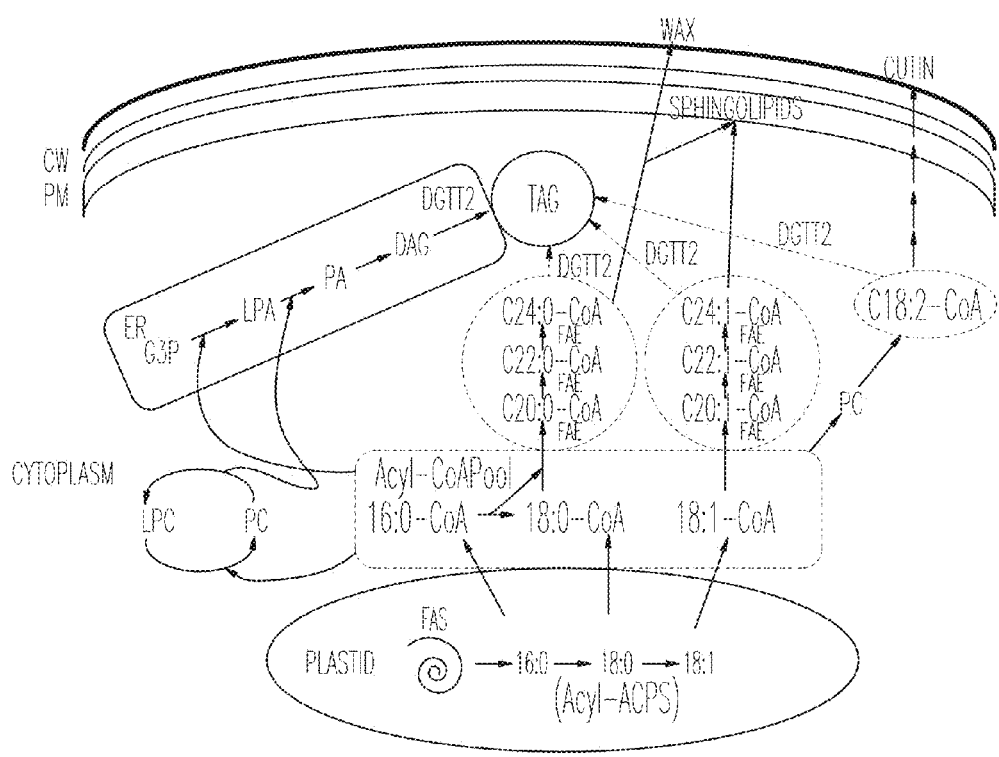
FIG. 10A-10E shows a schematic overview of altered diversion of acyl-CoAs groups from other pathways by DGTT2 in *Arabidopsis* leaves, and the diacylglycerol (DAG) and phosphatidic acid (PA) composition of DGTT2 and wild type plants.
Figure 10B:
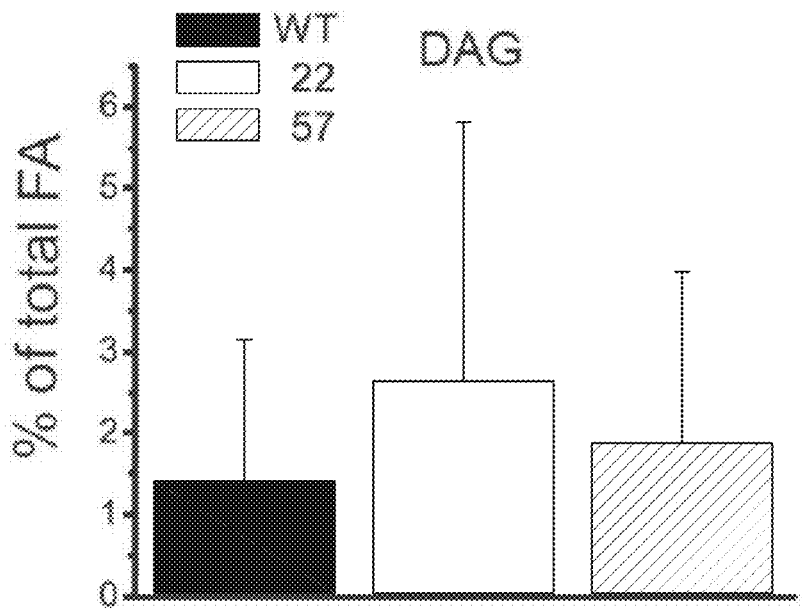
Figure 10C:
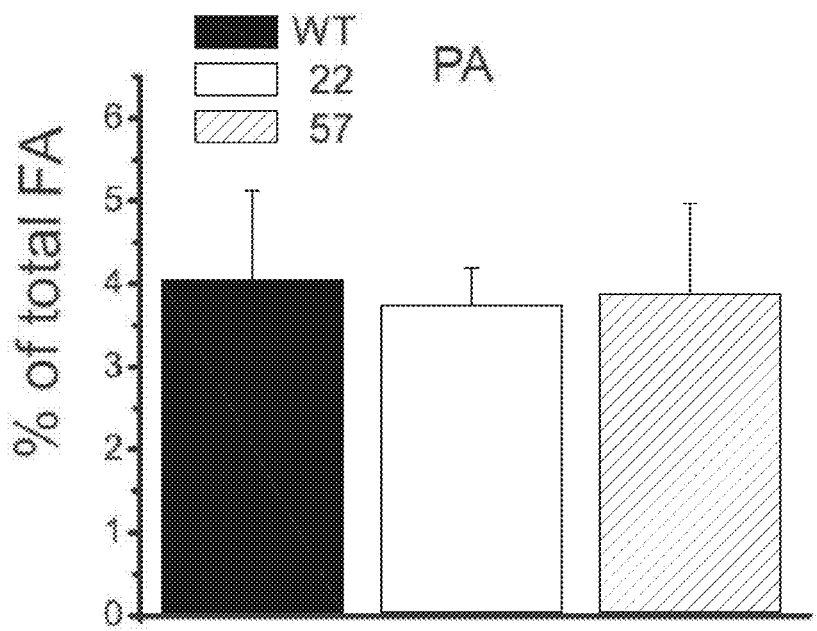
Figure 10D:
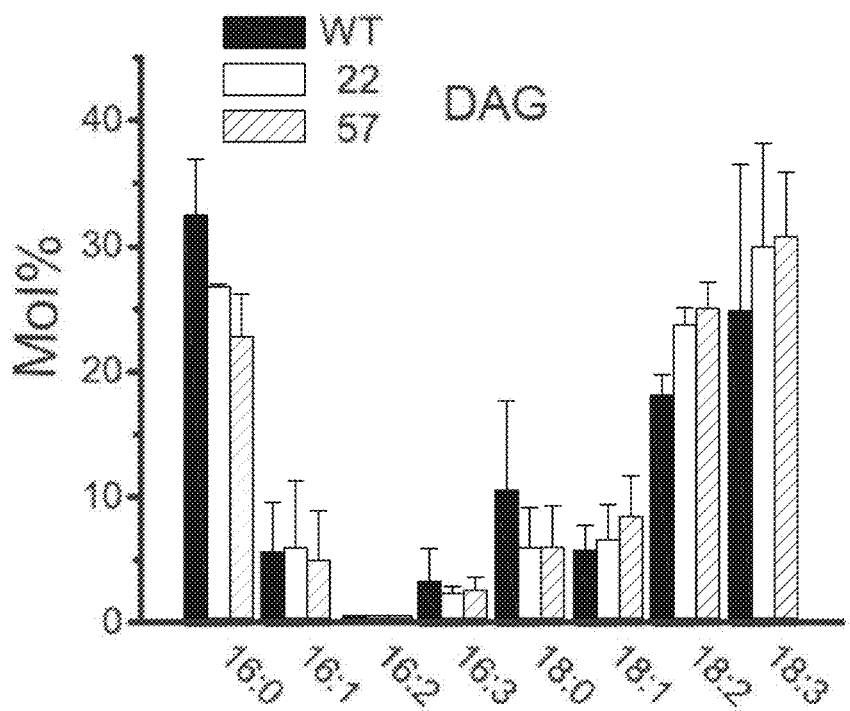
Figure 10E:
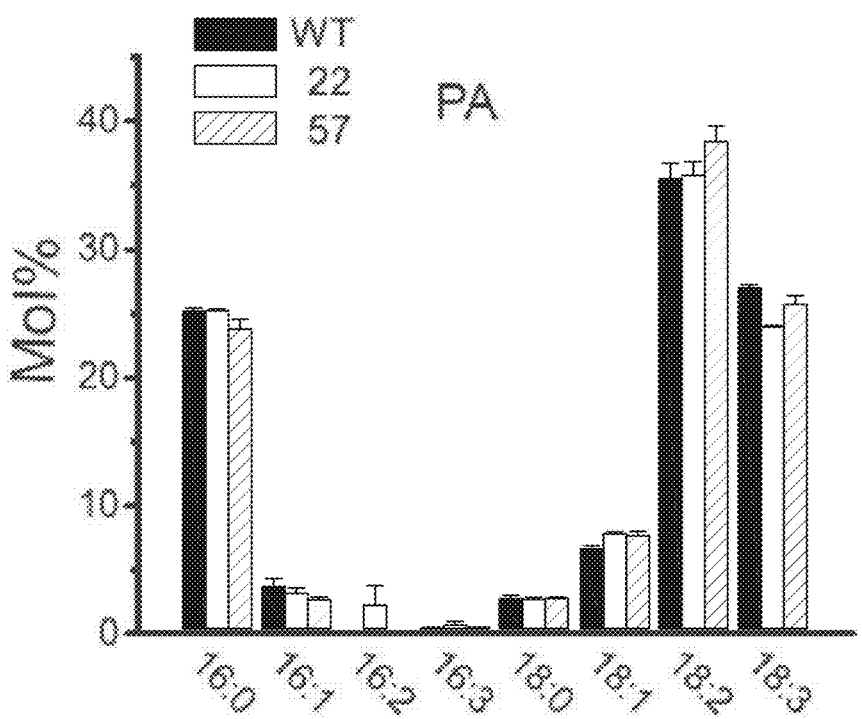

Active plant defense responses to insect herbivory are controlled by wound-induced production of the 18:3-derived phytohormone, jasmonoyl-L-isoleucine (JA-Ile) (Koo & Howe, Proc Natl Acad Sci USA 108, 9298-9303(2012). The altered lipid content of DGTT2-producing plants raised the possibility that increased larvae performance was caused by reduced levels of JA-Ile in the transgenic lines. To test this idea, JA-Ile levels were quantified in leaf tissue from insect-fed and control undamaged plants (FIG. 9D). Insect feeding increased the JA-Ile content in the damaged leaves of the wild type and two transgenic lines. In both control and damaged leaves, the amount of JA-Ile in DGTT2-producing lines was comparable to that observed in the wild type.

REFERENCES

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

Banilas, G., Karampelias, M., Makariti, I., Kourti, A., and Hatzopoulos, P. (2011). The olive DGAT2 gene is developmentally regulated and shares overlapping but distinct expression patterns with DGAT1. J Exp Bot 62, 521-532.

Bonaventure, G., Beisson, F., Ohlrogge, J., and Pollard, M. (2004). Analysis of the aliphatic monomer composition of polyesters associated with *Arabidopsis* epidermis: occurrence of octadeca-cis-6, cis-9-diene-1,18-dioate as the major component. Plant J 40, 920-930.

Boyle, N. R., Page, M. D., Liu, B., Blaby, I. K., Casero, D., Kropat, J., Cokus, S., Hong-Hermesdorf, A., Shaw, J., Karpowicz, S. J., Gallaher, S., Johnson, S., Benning, C., Pellegrini, M., Grossman, A., and Merchant, S. S. (2012). Three acyltransferases and a nitrogen responsive regulator are implicated in nitrogen starvation-induced triacylglycerol accumulation in *Chlamydomonas*. J Biol Chem.

Busik, J. V., Reid, G. E., and Lydic, T. A. (2009). Global analysis of retina lipids by complementary precursor ion and neutral loss mode tandem mass spectrometry. Methods Mol Biol 579, 33-70.

Cases, S., Smith, S. J., Zheng, Y. W., Myers, H. M., Lear, S. R., Sande, E., Novak, S., Collins, C., Welch, C. B., Lusis, A. J., Erickson, S. K., and Farese, R. V., Jr. (1998). Identification of a gene encoding an acyl CoA:diacylglycerol acyltransferase, a key enzyme in triacylglycerol synthesis. Proc Natl Acad Sci USA 95, 13018-13023.

Chao, D. Y., Gable, K., Chen, M., Baxter, I., Dietrich, C. R., Cahoon, E. B., Guerinot, M. L., Lahner, B., Lu, S., Markham, J. E., Morrissey, J., Han, G., Gupta, S. D., Harmon, J. M., Jaworski, J. G., Dunn, T. M., and Salt, D. E. (2011). Sphingolipids in the root play an important role in regulating the leaf ionome in *Arabidopsis thaliana*. Plant Cell 23, 1061-1081.

Chapman, K. D., and Ohlrogge, J. B. (2012). Compartmentation of triacylglycerol accumulation in plants. J Biol Chem 287, 2288-2294.

Chen, M., Markham, J. E., Dietrich, C. R., Jaworski, J. G., and Cahoon, E. B. (2008). Sphingolipid long-chain base hydroxylation is important for growth and regulation of sphingolipid content and composition in *Arabidopsis*. Plant Cell 20, 1862-1878.

Chen, M., Cahoon, E. B., Saucedo-Garcia, M., Plasencia, J., and Gavilanes-Ruiz, M. (2009). Plant sphingolipids:

Structure, synthesis and function. In Lipids in Photosynthesis: Essential and Regulatory Functions, H. Wada and N. Murata, eds (Dordrecht, Netherlands: Springer), pp. 77-115.

Clough, S. J., and Bent, A. F. (1998). Floral dip: a simplified method for *Agrobacterium*-mediated transformation of *Arabidopsis thaliana*. Plant J 16, 735-743.

Deng, X. D., Gu, B., Li, Y. J., Hu, X. W., Guo, J. C., and Fei, X. W. (2012). The Roles of acyl-CoA: Diacylglycerol Acyltransferase 2 Genes in the Biosynthesis of Triacylglycerols by the Green Algae *Chlamydomonas reinhardtii*. Mol Plant online.

Durrett, T. P., Benning, C., and Ohlrogge, J. (2008). Plant triacylglycerols as feedstocks for the production of biofuels. Plant J 54, 593-607.

Durrett, T. P., McClosky, D. D., Tumaney, A. W., Elzinga, D. A., Ohlrogge, J., and Pollard, M. (2010). A distinct DGAT with sn-3 acetyltransferase activity that synthesizes unusual, reduced-viscosity oils in *Euonymus* and transgenic seeds. Proc Natl Acad Sci USA 107, 9464-9469.

Fan, J., Andre, C., and Xu, C. (2011). A chloroplast pathway for the de novo biosynthesis of triacylglycerol in *Chlamydomonas reinhardtii*. FEBS Lett 585, 1985-1991.

Franke, R., Briesen, I., Wojciechowski, T., Faust, A., Yephremov, A., Nawrath, C., and Schreiber, L. (2005). Apoplastic polyesters in *Arabidopsis* surface tissues—a typical suberin and a particular cutin. Phytochemistry 66, 2643-2658.

Gietz, R. D., Schiestl, R. H., Willems, A. R., and Woods, R. A. (1995). Studies on the transformation of intact yeast cells by the LiAc/SS-DNA/PEG procedure. Yeast 11, 355-360.

Gaur, S., and Reed, T. (1995). An atlas of thermal data for biomass and other fuels. NREL/TB-433-7965, UC Category: 1310, DE95009212, National Renewable laboratory, Golden Colo., USA.

Goodson, C., Roth, R., Wang, Z. T., and Goodenough, U. (2011). Structural correlates of cytoplasmic and chloroplast lipid body synthesis in *Chlamydomonas reinhardtii* and stimulation of lipid body production with acetate boost. Eukaryot Cell 10, 1592-1606.

Guiheneuf, F., Leu, S., Zarka, A., Khozin-Goldberg, I., Khalilov, I., and Boussiba, S. (2011). Cloning and molecular characterization of a novel acyl-CoA: diacylglycerol acyltransferase 1-like gene (PtDGAT1) from the diatom *Phaeodactylum tricornutum*. FEBS J 278, 3651-3666.

Haimi, P., Uphoff, A., Hermansson, M., and Somerharju, P. (2006). Software tools for analysis of mass spectrometric lipidome data. Analytical chemistry 78, 8324-8331.

Halim, R., Danquah, M. K., and Webley, P. A. (2012). Extraction of oil from microalgae for biodiesel production: A review. Biotechnol Adv 30, 709-732.

Harris, E. H. (1989). The *Chlamydomonas* Source Book. (New York: Academic Press).

Hernandez, M. L., Whitehead, L., He, Z., Gazda, V., Gilday, A., Kozhevnikova, E., Vaistij, F. E., Larson, T. R., and Graham, I. A. (2012). A cytosolic acyltransferase contributes to triacylglycerol synthesis in sucrose-rescued *Arabidopsis* seed oil catabolism mutants. Plant Physiol 160, 215-225.

Irizarry, R. A., Bolstad, B. M., Collin, F., Cope, L. M., Hobbs, B., and Speed, T. P. (2003a). Summaries of Affymetrix GeneChip probe level data. Nucleic Acids Res 31, e15.

Irizarry, R. A., Hobbs, B., Collin, F., Beazer-Barclay, Y. D., Antonellis, K. J., Scherf, U., and Speed, T. P. (2003b). Exploration, normalization, and summaries of high density oligonucleotide array probe level data. Biostatistics 4, 249-264.

Jako, C., Kumar, A., Wei, Y., Zou, J., Barton, D. L., Giblin, E. M., Covello, P. S., and Taylor, D. C. (2001). Seed-specific over-expression of an *Arabidopsis* cDNA encoding a diacylglycerol acyltransferase enhances seed oil content and seed weight. Plant Physiol 126, 861-874.

Kalscheuer, R., and Steinbuchel, A. (2003). A novel bifunctional wax ester synthase/acyl-CoA: diacylglycerol acyltransferase mediates wax ester and triacylglycerol biosynthesis in *Acinetobacter calcoaceticus* ADP1. J Biol Chem 278, 8075-8082.

Kalscheuer, R., Luftmann, H., and Steinbuchel, A. (2004). Synthesis of novel lipids in *Saccharomyces cerevisiae* by heterologous expression of an unspecific bacterial acyltransferase. Appl Environ Microbiol 70, 7119-7125.

King, A., Nam, J. W., Han, J., Hilliard, J., and Jaworski, J. G. (2007). Cuticular wax biosynthesis in *petunia* petals: cloning and characterization of an alcohol-acyltransferase that synthesizes wax-esters. Planta 226, 381-394.

Koo, A. J., and Howe, G. A. (2012). Catabolism and deactivation of the lipid-derived hormone jasmonoyl-isoleucine. Front Plant Sci 3, 19.

Koo, A. J., Cooke, T. F., and Howe, G. A. (2011). Cytochrome P450 CYP94B3 mediates catabolism and inactivation of the plant hormone jasmonoyl-L-isoleucine. Proc Natl Acad Sci USA 108, 9298-9303.

Kosma, D. K., and Jenks, M. A. (2007). Eco-physiological and molecular-genetic determinants of plant cuticle function in drought and salt tolerant crops. In Advances in Molecular Breeding Toward Drought and Salt Tolerant Crops., M. A. Jenks, P. M. Hasegawa, and S. M. Jain, eds (Netherlands: Springer), pp. 91-120.

Kosma, D. K., Bourdenx, B., Bernard, A., Parsons, E. P., Lu, S., Joubes, J., and Jenks, M. A. (2009). The impact of water deficiency on leaf cuticle lipids of *Arabidopsis*. Plant Physiol 151, 1918-1929.

Kunst, L., and Samuels, L. (2009). Plant cuticles shine: advances in wax biosynthesis and export. Curr Opin Plant Biol 12, 721-727.

La Russa, M., Bogen, C., Uhmeyer, A., Doebbe, A., Filippone, E., Kruse, O., and Mussgnug, J. H. (2012). Functional analysis of three type-2 DGAT homologue genes for triacylglycerol production in the green microalga *Chlamydomonas reinhardtii*. J Biotechnol online Laby, R. J., Kim, D., and Gibson, S. I. (2001). The rami mutant of *Arabidopsis* exhibits severely decreased beta-amylase activity. Plant Physiol 127, 1798-1807.

Lardizabal, K., Effertz, R., Levering, C., Mai, J., Pedroso, M. C., Jury, T., Aasen, E., Gruys, K., and Bennett, K. (2008). Expression of Umbelopsis ramanniana DGAT2A in seed increases oil in soybean. Plant Physiol 148, 89-96.

Li-Beisson, Y., Shorrosh, B., Beisson, F., Andersson, M. X., Arondel, V., Bates, P. D., Baud, S., Bird, D., Debono, A., Durrett, T. P., Franke, R. B., Graham, I. A., Katayama, K., Kelly, A. A., Larson, T., Markham, J. E., Miguel, M., Molina, I., Nishida, I., Rowland, O., Samuels, L., Schmid, K. M., Wada, H., Welti, R., Xu, C., Zallot, R., and Ohlrogge, J. (2010). Acyl-lipid metabolism. *Arabidopsis* Book 8, e0133.

Li, F., Wu, X., Lam, P., Bird, D., Zheng, H., Samuels, L., Jetter, R., and Kunst, L. (2008). Identification of the wax ester synthase/acyl-coenzyme A: diacylglycerol acyltransferase WSD1 required for stem wax ester biosynthesis in *Arabidopsis*. Plant Physiol 148, 97-107.

Li, L., Foster, C. M., Gan, Q., Nettleton, D., James, M. G., Myers, A. M., and Wurtele, E. S. (2009). Identification of the novel protein QQS as a component of the starch metabolic network in *Arabidopsis* leaves. Plant J 58, 485-498.

Li, Y., Beisson, F., Koo, A. J., Molina, I., Pollard, M., and Ohlrogge, J. (2007). Identification of acyltransferases required for cutin biosynthesis and production of cutin with suberin-like monomers. Proc Natl Acad Sci USA 104, 18339-18344.

Lung, S. C., and Weselake, R. J. (2006). Diacylglycerol acyltransferase: A key mediator of plant triacylglycerol synthesis. Lipids 41, 1073-1088.

Markham, J. E., Li, J., Cahoon, E. B., and Jaworski, J. G. (2006). Separation and identification of major plant sphingolipid classes from leaves. J Biol Chem 281, 22684-22694.

Merrill, A. H., Jr., Sullards, M. C., Allegood, J. C., Kelly, S., and Wang, E. (2005). Sphingolipidomics: high-throughput, structure-specific, and quantitative analysis of sphingolipids by liquid chromatography tandem mass spectrometry. Methods 36, 207-224.

Milcamps, A., Tumaney, A. W., Paddock, T., Pan, D. A., Ohlrogge, J., and Pollard, M. (2005). Isolation of a gene encoding a 1,2-diacylglycerol-sn-acetyl-CoA acetyltransferase from developing seeds of *Euonymus alatus*. J Biol Chem 280, 5370-5377.

Miller, R., Wu, G., Deshpande, R. R., Vieler, A., Gartner, K., Li, X., Moellering, E. R., Zauner, S., Cornish, A. J., Liu, B., Bullard, B., Sears, B. B., Kuo, M. H., Hegg, E. L., Shachar-Hill, Y., Shiu, S. H., and Benning, C. (2010). Changes in transcript abundance in *Chlamydomonas reinhardtii* following nitrogen deprivation predict diversion of metabolism. Plant Physiol 154, 1737-1752.

Molina, I., Bonaventure, G., Ohlrogge, J., and Pollard, M. (2006). The lipid polyester composition of *Arabidopsis thaliana* and *Brassica napus* seeds. Phytochemistry 67, 2597-2610.

Murashige, T., and Skoog, F. (1962). A revised medium for rapid growth and bio assays with tobacco tissue cultures. Physiol. Plant. 15, 473-497.

Oakes, J., Brackenridge, D., Colletti, R., Daley, M., Hawkins, D. J., Xiong, H., Mai, J., Screen, S. E., Val, D., Lardizabal, K., Gruys, K., and Deikman, J. (2011). Expression of fungal diacylglycerol acyltransferase2 genes to increase kernel oil in maize. Plant Physiol 155, 1146-1157.

Routaboul, J. M., Benning, C., Bechtold, N., Caboche, M., and Lepiniec, L. (1999). The TAG1 locus of *Arabidopsis* encodes for a diacylglycerol acyltransferase. Plant Physiol Biochem 37, 831-840.

Saha, S., Enugutti, B., Rajakumari, S., and Rajasekharan, R. (2006). Cytosolic triacylglycerol biosynthetic pathway in oilseeds. Molecular cloning and expression of peanut cytosolic diacylglycerol acyltransferase. Plant Physiol 141, 1533-1543.

Sandager, L., Gustaysson, M. H., Stahl, U., Dahlqvist, A., Wiberg, E., Banas, A., Lenman, M., Ronne, H., and Stymne, S. (2002). Storage lipid synthesis is non-essential in yeast. J Biol Chem 277, 6478-6482.

Sanjaya, Durrett, T. P., Weise, S. E., and Benning, C. (2011). Increasing the energy density of vegetative tissues by diverting carbon from starch to oil biosynthesis in transgenic *Arabidopsis*. Plant Biotechnol J 9, 874-883.

Sherman, F. (2002). Getting started with yeast. Methods in enzymology 350, 3-41.

Shockey, J. M., Gidda, S. K., Chapital, D. C., Kuan, J. C., Dhanoa, P. K., Bland, J. M., Rothstein, S. J., Mullen, R. T., and Dyer, J. M. (2006). Tung tree DGAT1 and DGAT2 have nonredundant functions in triacylglycerol biosynthesis and are localized to different subdomains of the endoplasmic reticulum. Plant Cell 18, 2294-2313.

Tamura, K., Peterson, D., Peterson, N., Stecher, G., Nei, M., and Kumar, S. (2011). MEGA5: molecular evolutionary genetics analysis using maximum likelihood, evolutionary distance, and maximum parsimony methods. Mol Biol Evol 28, 2731-2739.

Wagner, M., Hoppe, K., Czabany, T., Heilmann, M., Daum, G., Feussner, I., and Fulda, M. (2010). Identification and characterization of an acyl-CoA:diacylglycerol acyltransferase 2 (DGAT2) gene from the microalga *O. tauri*. Plant Physiol Biochem 48, 407-416.

Xu, C., Fan, J., Riekhof, W., Froehlich, J. E., and Benning, C. (2003). A permease-like protein involved in ER to thylakoid lipid transfer in *Arabidopsis*. EMBO J 22, 2370-2379.

Yang, Z., and Ohlrogge, J. B. (2009). Turnover of fatty acids during natural senescence of *Arabidopsis*, Brachypodium, and switchgrass and in *Arabidopsis* beta-oxidation mutants. Plant Physiol 150, 1981-1989.

Yen, C. L., Stone, S. J., Koliwad, S., Harris, C., and Farese, R. V., Jr. (2008). Thematic review series: glycerolipids. DGAT enzymes and triacylglycerol biosynthesis. J Lipid Res 49, 2283-2301.

Zou, J., Wei, Y., Jako, C., Kumar, A., Selvaraj, G., and Taylor, D. C. (1999). The *Arabidopsis thaliana* TAG1 mutant has a mutation in a diacylglycerol acyltransferase gene. Plant J 19, 645-653.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to summarize features of the invention.

Statements:

1. A construct comprising a nucleic acid encoding a polypeptide with at least 40% sequence identity with an amino acid sequence selected from the group of SEQ ID NO:1, 3, 5, and 7, that is operably linked to a heterologous promoter operable in at least one plant tissue.
2. The construct of Statement 1, wherein the polypeptide has at least about 50% sequence identity, at least 55% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity with an amino acid sequence selected from the group of SEQ ID NO:1, 3, 5, and 7.
3. The construct of Statement 1 or 2, wherein the nucleic acid has at least about 50% sequence identity or complementarity with any of the SEQ ID NO:2, 4, or 6.
4. The construct of any of Statements 1-3, wherein the nucleic acid has at least about 50% sequence identity, at least 55% sequence identity, at least about 60% sequence identity, at least 70% sequence identity, at least about 80% sequence identity, at least 90% sequence identity, at least about 95% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity or complementarity with any of the SEQ ID NO:2, 4, or 6.

5. The construct of any of Statements 1-4, wherein the polypeptide is a Diacylglycerol Acyltransferase Type Two enzyme.

6. The construct of any of Statements 1-5, wherein the polypeptide is a Diacylglycerol Acyltransferase Type Two enzyme selected from the group of DGTT1, DGTT2, DGTT3 and DGTT4.

7. The construct of any of Statements 1-6, wherein the polypeptide is a Diacylglycerol Acyltransferase Type Two enzyme is DGTT2 or DGTT3.

8. The construct of any of Statements 1-7, wherein the polypeptide is a Diacylglycerol Acyltransferase Type Two enzyme with at least 50% of DGTT2 or DGTT3 activity as measured in an assay of microsomal protein conversion of labeled monoacyl-CoA to labeled triacylglycerols.

9. The construct of any of Statements 1-8, wherein the polypeptide increases expression of a protein selected from the group of wax ester synthase (WS), diacylglycerol acyltransferase (DGAT), Qua-Quine Starch (QQS), Cytosolic beta-amylase, HXXXD-type acyl-transferase, Sodium potassium root defective 2, Peroxidase superfamily protein, PARI protein, Nodulin Mt-N21/EamA-like transporter, and any combination thereof.

10. The construct of any of Statements 1-9, wherein the polypeptide decreases expression of mini zinc finger 2, UDP-Glycosyltransferase superfamily protein, or a combination thereof.

11. The construct of any of Statements 1-10, wherein the promoter is a constitutive promoter, a developmental promoter, or an inducible promoter.

12. The construct of any of Statements 1-11, wherein the promoter is selected from the group of CaMV 35S promoter, a CaMV 19S promoter, a nos promoter, an Adh1 promoter, a sucrose synthase promoter, an α-tubulin promoter, a ubiquitin promoter, an actin promoter, a PEPCase promoter, a GAL4/UAS promoter, an R gene promoter, a poplar xylem-specific secondary cell wall specific cellulose synthase 8 promoter, a cauliflower mosaic virus promoter, an OLE (Oleosin) promoter, a Z10 promoter from a gene encoding a 10 kD zein protein, a Z27 promoter from a gene encoding a 27 kD zein protein, a light inducible promoter derived from the pea rbcS gene, an actin promoter from rice, a phaseolin promoter, or any combination thereof.

13. A plant cell comprising the construct of any of Statements 1-12.

14. A plant seed comprising the construct of any of Statements 1-12.

15. A plant comprising the construct of any of Statements 1-12.

16. A reproductively competent plant comprising the construct of any of Statements 1-12.

17. A plant comprising the construct of any of Statements 1-12, wherein the plant has lipid in its tissues or seeds.

18. A plant of Statement 15, 16, or 17, or comprising the construct of any of Statements 1-12, wherein the plant has lipid in its vegetative tissues.

19. The plant of any of Statements 15-18, wherein the plant has lipid comprising triacylglycerol.

20. A plant of any of Statements 15-18, or 19, or comprising the construct of any of Statements 1-12, wherein the plant has at least 1% lipid per dry weight of tissue.

21. A plant of any of Statements 15-18, or 19, or comprising the construct of any of Statements 1-12, wherein the plant has at least 1% lipid, or at least 2% lipid, or at least 3% lipid, or at least 4% lipid, or at least 5% lipid, or at least 6% lipid, or at least 7% lipid, or at least 8% lipid, or at least 9% lipid, or at least 10% lipid, or at least 11% lipid, or at least 12% lipid, or at least 13% lipid, or at least 14% lipid, or at least 15% lipid, or at least 16% lipid, or at least 17% lipid, or at least 18% lipid, or at least 19% lipid, or at least 20% lipid per dry weight of tissue.

22. The plant of any of Statements 15-18, or 19, or comprising the construct of any of Statements 1-12, wherein the plant has about 1% to about 30% lipid per dry weight of tissue, or about 5% to about 25% lipid per dry weight of tissue, or about 10% to about 20% lipid per dry weight of tissue.

23. The plant of any of Statements 15-22, wherein the plant is an oleaginous plant.

24. The plant of any of Statements 15-23, wherein the plant is selected from the group of an oleaginous plant, an *Arabidopsis* plant, corn, sugar beets, soybean, sugar cane, potato, grasses (e.g., *miscanthus*, switchgrass, and the like), rice, a beet species, a grape species, an *Arabidopsis* species, a *Brassica* species, a *Brassica napus* plant, an algae species, an oilseed rape species, a sunflower, a soybean species, a flax species, an olive species, an alfalfa species, an oat species, a wheat species, a poplar, an aspen, a willow, and similar plant species.

25. The plant of any of Statements 15-24, wherein the plant has less cutin and more fatty acids than an wild type plant of the same species.

26. An isolated lipid from tissues of the plant of any of Statements 1-12, 15-24, or 25.

27. An isolated lipid from vegetative tissues of the plant of any of Statements 1-12, 15-24, or 25.

28. The isolated lipid of Statement 26 or 27, containing trace amounts of the construct of any of Statements 1-12.

29. A method, comprising transfecting at least one plant cell with the construct of any of Statements 1-12 and growing the at least one plant cell into a population of plant cells.

30. A method, comprising transfecting a plant tissue with the construct of any of Statements 1-12 and growing the tissue into a whole plant.

31. The method of Statement 29 or 30, wherein the population of plant cells or tissues of the whole plant has at least 1% lipid per dry weight of cell population or per dry weight of tissue.

32. A method of any of Statements 29-31, wherein the population of plant cells or tissues of the whole plant has at least 1% lipid, or at least 2% lipid, or at least 3% lipid, or at least 4% lipid, or at least 5% lipid, or at least 6% lipid, or at least 7% lipid, or at least 8% lipid, or at least 9% lipid, or at least 10% lipid, or at least 11% lipid, or at least 12% lipid, or at least 13% lipid, or at least 14% lipid, or at least 15% lipid, or at least 16% lipid, or at least 17% lipid, or at least 18% lipid, or at least 19% lipid, or at least 20% lipid per dry weight of tissue or of cell population.

33. The method of any of Statements 29-32, wherein the population of plant cells or tissues of the whole plant has at about 1% to about 30% lipid per dry weight of tissue, or about 5% to about 25% lipid per dry weight of tissue, or about 10% to about 20% lipid per dry weight of tissue.

34. A method, comprising,
   a) providing at least one plant cell that comprises the construct of any of Statements 1-12;
   b) culturing the at least one plant cell in media that supports regeneration of plant tissue, to thereby generate at least one transformed plant tissue;
   c) generating at least one plant from the at least one transformed plant tissue to thereby generate at least one transformed plant; and
   d) growing the at least one transformed plant.
35. The method of statement 34, wherein the at least one transformed plant is a reproductively competent plant.
36. The method of Statement 34 or 35, further comprising growing the at least one transformed plant to generate at least one transformed plant with seeds.
37. The method of any of Statements 34-36, wherein the at least one transformed plant has transformed seeds comprising the construct of any of Statements 1-12.
38. The method of any of Statement 34-37, further comprising isolating one or more seeds from the least one transformed plant with seeds.
39. The method of any of Statements 34-37, wherein the at least one transformed plant has at least 1% lipid per dry weight of tissue.
40. The method of any of Statements 34-39, wherein the at least one transformed plant has at least 1% lipid per dry weight of vegetative tissue.
41. The method of any of Statements 34-40, wherein the at least one transformed plant has at least 1% lipid, or at least 2% lipid, or at least 3% lipid, or at least 4% lipid, or at least 5% lipid, or at least 6% lipid, or at least 7% lipid, or at least 8% lipid, or at least 9% lipid, or at least 10% lipid, or at least 11% lipid, or at least 12% lipid, or at least 13% lipid, or at least 14% lipid, or at least 15% lipid, or at least 16% lipid, or at least 17% lipid, or at least 18% lipid, or at least 19% lipid, or at least 20% lipid per dry weight of cell population or per dry weight of tissue.
42. The method of any of Statements 34-41, wherein the at least one transformed plant has at about 1% to about 30% lipid per dry weight of tissue, or about 5% to about 25% lipid per dry weight of tissue, or about 10% to about 20% lipid per dry weight of tissue.
43. The method of any of Statements 34-42, further comprising isolating increased lipid from the tissues or seeds of the plant.
44. A method, comprising,
   a) providing a plant tissue that comprises the construct of any of Statements 1-12;
   b) growing the tissue into a whole plant; and
   c) isolating lipid from the tissues or seeds of the plant.
45. The method of statement 44, wherein the plant is a reproductively competent plant.
46. The method of any of Statements 31-33, 39-44, or 45, wherein the lipid comprises triacylglycerol.
47. The method of any of Statements 31-33, 39-45, or 46, wherein the lipid is vegetable lipid.
48. The method of any of Statements 31-33, 39-44, or 47, or 47, wherein the lipid is isolated from a tissue is selected from the group of a plant leaf, plant stem, plant stalk, or a combination thereof.
49. The method of Statement 48, wherein the tissue is from an oleaginous plant.
50. The method of Statement 48 or 49, wherein the tissue is from a plant selected from the group of an oleaginous plant, an *Arabidopsis* plant, corn, sugar beets, soybean, sugar cane, potato, grasses (e.g., *miscanthus*, switchgrass, and the like), rice, a beet species, a grape species, an *Arabidopsis* species, a *Brassica* species, a *Brassica napus* plant, an algae species, an oilseed rape species, a sunflower, a soybean species, a flax species, an olive species, an alfalfa species, an oat species, a wheat species, a poplar, an aspen, a willow, or a combination thereof.
51. The method of any of Statements 48-50, wherein the tissue is from a plant selected form the group of a rice plant, a *Miscanthus* plant, oilseed rape plant, sunflower plant, soybean plant, flax plant, olive plant, alfalfa plant, oat plant, a switchgrass plant.
52. The method of any of Statements 29-51, further comprising manufacturing a biofuel from a lipid in the plant cells or the plant.
53. A biofuel comprising the lipid of any of Statements 26-28.

The specific methods, plants, seeds, and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a plant" or "a nucleic acid" or "a polypeptide" includes a plurality of such plants, nucleic acids or polypeptides (for example, a series of plants, a solution of nucleic acids or polypeptides, or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A plant seed or plant comprising a nucleic acid construct comprising a nucleic acid encoding a diacylglycerol acyltransferase polypeptide with at least 95% sequence identity with SEQ ID NO: 3 that is operably linked to a heterologous promoter operable in leaves, wherein the leaves of a plant grown from the plant seed, or the leaves of the plant contain oil droplets than wild type plants.

2. The plant seed or plant of claim 1, wherein the plant seed or plant is reproductively competent.

3. The plant seed or plant of claim 1, wherein the plant has at least 11% lipid per dry weight of tissue.

4. The plant seed or plant of claim 1, wherein the plant seed is an oleaginous plant seed or wherein the plant an oleaginous plant.

5. The plant seed or plant of claim 1, wherein the plant seed or plant is selected from an oleaginous, *Arabidopsis*, corn, sugar beet, soybean, sugar cane, potato, grass, rice, beet, grape, *Brassica, Brassica napus,* algal, oilseed rape, sunflower, soybean, flax, olive, alfalfa, oat, wheat, poplar, aspen, and willow plant seed or plant.

6. A method comprising:
(a) transfecting a plant tissue or plant cell with a nucleic acid construct comprising a nucleic acid encoding a diacylglycerol acyltransferase polypeptide with at least 95% sequence identity with SEQ ID NO: 3 that is operably linked to a heterologous promoter operable in plant tissues;
(b) growing the tissue or the cell into a whole plant comprising leaves that contain more oil droplets than wild type plants; and
(c) isolating lipid from vegetative tissues or leaves of the whole plant.

7. The method of claim 6, wherein the plant tissue or plant cell is an oleaginous plant tissue or plant cell, a corn tissue or cell, a sugar beet tissue or cell, a soybean tissue or cell, a sunflower tissue or cell, a sugar cane tissue or cell, a potato tissue or cell, a flax tissue or cell, a grass tissue or cell, a Miscanthus tissue or cell, a switchgrass tissue or cell, a rice tissue or cell, a poplar tissue or cell, an aspen tissue or cell, a willow tissue or cell, a beet species tissue or cell, a grape species tissue or cell, an *Arabidopsis* species tissue or cell, a *Brassica* species tissue or cell, a *Brassica napus* plant tissue or plant cell, an algae species tissue or cell, an oilseed rape species tissue or cell, a soybean species tissue or cell, a flax species tissue or cell, an olive species tissue or cell, an alfalfa species tissue or cell, an oat species tissue or cell, or a wheat species tissue or cell.

8. The method of claim 6, where.in the whole plant is a reproductively competent plant.

9. The method of claim 6, wherein the whole has at least 1% lipid per dry weight of tissue.

10. The method of claim 6, further comprising isolating lipid from seeds of the whole plant.

11. The method of claim 6, further comprising manufacturing a biofuel from a lipid in the whole plant or its tissues.

12. A method comprising:
  (a) growing a plant from a seed with a nucleic acid construct comprising a nucleic acid encoding a diacylglycerol acyltransferase polypeptide with at 95% sequence identity with SEQ ID NO: 3 that is operably linked to a heterologous promoter operable in plant tissues to thereby generate a plant comprising leaves that contain more oil droplets than wild type plants; and
  (b) harvesting lipid or oil from vegetative tissues of the plant.

13. The method of claim 12, wherein the plant has at least 11% lipid per dry weight of tissue.

14. The method of claim 12, further comprising manufacturing a biofuel from the lipid or oil harvested.

15. The plant seed or plant of claim 1, wherein the plant has more starch in vegetative tissues than wild type plants.

16. The plant seed or plant of claim 1, wherein the plant has more very long fatty acids than wild type plants.

* * * * *

UNITED STATES PATENT AND TRADEMARK OFFICE
CERTIFICATE OF CORRECTION

PATENT NO. : 10,392,629 B2
APPLICATION NO. : 14/598953
DATED : August 27, 2019
INVENTOR(S) : Benning et al.

Page 1 of 1

It is certified that error appears in the above-identified patent and that said Letters Patent is hereby corrected as shown below:

On the Title Page

Page 2, Column 1, Line 22, delete "Restricticon" and insert --Restriction-- therefor Page 3, Column 1, Line 24, delete "uonymus" and insert --Euonymus-- therefor Page 4, Column 1, Line 42, delete "DramaticIncrease" and insert --Dramatic Increase-- therefor In the Claims Column 102, Line 66, Claim 8, delete "where.in" and insert --wherein-- therefor Column 103, Line 1, Claim 9, after "whole", insert --plant--

Signed and Sealed this
Seventh Day of April, 2020

Andrei Iancu
*Director of the United States Patent and Trademark Office*

SEQUENCE LISTING

<160> NUMBER OF SEQ ID NOS: 39

<210> SEQ ID NO 1
<211> LENGTH: 320
<212> TYPE: PRT
<213> ORGANISM: Chlamydomonas reinhardtii

<400> SEQUENCE: 1

Met Gln Ser Lys Arg Cys Ala Glu Leu Ala Ser Gly Ala Leu Trp Pro
1               5                   10                  15

Met Asp Arg Asp Gln Met Arg Asp Arg Asp Pro Trp Lys Leu Arg Asp
                20                  25                  30

Arg Ala Ile Ser Gln Ala Trp Val Trp Pro Leu Leu Ile Gly Thr Leu
            35                  40                  45

Leu Tyr Val Gln Ser Thr Thr Leu Thr Ile Ala Phe Leu Leu Trp His
        50                  55                  60

Ile Trp Lys Val Met Ala Ser Tyr Phe Pro Gly Ala Arg Leu Ile Lys
65                  70                  75                  80

Thr Ala Asp Leu Asp Pro Ala Gly Arg Tyr Ile Phe Val Ser His Pro
                85                  90                  95

His Gly Val Ile Ala Ile Ser Asp Trp Leu Ala Phe Ala Thr Glu Ala
            100                 105                 110

Leu Gly Phe Ser Lys Leu Phe Pro Gly Leu Asp Leu Arg Cys Ala Thr
        115                 120                 125

Leu Ala Ser Asn Phe Trp Val Pro Gly Leu Arg Glu Tyr Ile Leu Ser
    130                 135                 140

His Gly Met Cys Gly Val Gly Arg Asp Thr Leu Ala Arg Val Leu Thr
145                 150                 155                 160

Gly Lys Pro Gly Arg Ala Val Val Leu Val Val Gly Gly Ala Ser Glu
                165                 170                 175

Ala Leu Leu Ala Ala Glu Gly Thr Tyr Asp Leu Val Leu Arg Asn Arg
            180                 185                 190

Lys Gly Phe Val Arg Leu Ala Leu Gln Thr Gly Ala Ser Leu Val Pro
        195                 200                 205

Val Leu Ser Tyr Gly Glu Thr Asp Thr Phe His Thr Tyr Ile Pro Pro
    210                 215                 220

Pro Cys Ser Arg Ala Ala Ala Val Met Lys Val Leu Lys Gln Val Phe
225                 230                 235                 240

Gly Phe Ser Thr Pro Leu Cys Trp Gly Thr Gly Leu Phe Gly Gly Trp
                245                 250                 255

Gly Met Leu Ala Leu Gln Val Pro Leu Thr Val Val Gly Ala Pro
            260                 265                 270

Ile Gln Val Asp Lys Val Ser Ser Pro Thr Glu Ala Glu Val Ala Ala
        275                 280                 285

Leu His Lys Thr Tyr Thr Glu Ala Leu Gln Lys Leu Trp Asp Asp Thr
    290                 295                 300

Val Asp Lys Tyr Gly Lys Gly Val Lys Arg Pro Leu Ala Ile Val Gln

<210> SEQ ID NO 2
<211> LENGTH: 962
<212> TYPE: DNA
<213> ORGANISM: Chlamydomonas reinhardtii

<400> SEQUENCE: 2

```
atgcaaagta agcgttgtgc agagctggcc tctggggctc tgtggcccat ggaccgcgac      60
cagatgcgcg accgcgaccc atggaagctg cgcgaccgag ctataagcca agcatgggtg     120
tggcctctgc tcatcggcac attgctttac gtgcagagca ccacgctcac aattgccttc     180
ctgctgtggc atatctggaa ggttatggcc tcttacttcc ccggcgcccg cctgattaag     240
accgccgacc tggatccggc tggccgctat atattcgtga ccacccgca cggcgtcatc      300
gccatttccg actggctggc atttgccaca gaggcgctgg gcttctccaa actgttccca     360
ggcctggacc tgcgctgcgc cacgctggct tcaaacttct gggtgcctgg tttgcgtgag     420
tacatcctat cgcacggcat gtgcggcgtg gggcgagaca ctctggcgcg cgtgctgaca     480
ggaaagccgg ccgtgcggt tgtgttggtg gtgggcggcg cgtctgaggc gctgttggcg     540
gcggagggaa cttatgacct ggtgctgcgc aaccgcaagg gctttgtgcg cctggcgctg     600
cagaccggcg ccagtctggt gccggtgctg tcgtacggtg agacagacac cttccacacc     660
tacatcccgc cgccctgcag ccgggcgcc gcggtcatga aggtgctgaa gcaggtgttt      720
ggcttctcca cgcccctgtg ctggggcacc ggactgttcg ggggctgggg catgctagcg     780
ctgcaggtgc cgctcactgt ggtggtgggg caccatac aggtggacaa ggtgtccagt       840
cccacggagg ctgaggtggc ggcgctgcat aagacctaca cggaggcact gcagaagctg     900
tgggatgaca cagtggacaa gtacggcaag ggtgtcaagc ggccgctggc catcgtgcaa     960
tg                                                                    962
```

<210> SEQ ID NO 3
<211> LENGTH: 324
<212> TYPE: PRT
<213> ORGANISM: Chlamydomonas reinhardtii

<400> SEQUENCE: 3

```
Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
            20                  25                  30

Leu Thr Leu Phe Ile Tyr Cys Gly Trp Met His Val Leu Ala Leu
        35                  40                  45

Val Ile Leu Ser Phe Trp Tyr Arg Trp Ala Leu Val Thr Val Leu Leu
    50                  55                  60

Leu Tyr Ser Thr Leu Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Tyr Ile Phe
            100                 105                 110

Ala Glu Phe Pro His Gly Val Phe Pro Met Gly Pro Leu Ile Gly Ala
        115                 120                 125

Thr Glu Cys Gln Ile Met Phe Pro Gly Phe Asp Ile Phe Gly Leu Ala
    130                 135                 140
```

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys
            165                 170                 175

Gln Gly Ser Val Ala Val Ile Val Gly Gly Ile Ala Glu Met Tyr Met
            180                 185                 190

Gln Ser Pro Thr Lys Glu Gln Ile Met Leu Lys Asp Arg Lys Gly Phe
            195                 200                 205

Val Arg Val Ala Val Glu Glu Gly Val Asp Gly Ile Val Pro Val
210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
            245                 250                 255

Val Ala Tyr Leu Pro Leu Pro Arg Arg Arg Asn Ile Tyr Met Val Cys
            260                 265                 270

Gly Lys Pro Val Pro Val Thr Arg Thr Ala Arg Asp Asp Pro Lys Phe
            275                 280                 285

Glu Glu Val Val Asp Ala Thr His Ala Ala Val Met Ala Ala Leu Gln
290                 295                 300

Glu Ala Tyr Asp Arg His Lys Thr Glu Tyr Gly Trp Ala Asp Arg Pro
305                 310                 315                 320

Leu Val Ile Ser

<210> SEQ ID NO 4
<211> LENGTH: 1322
<212> TYPE: DNA
<213> ORGANISM: Chlamydomonas reinhardtii

<400> SEQUENCE: 4

```
ggatttgcaa ctttcgatat agttacgatt tgcgtgggac cgccccattc acctaagaag     60
cgggcctatt ggccgcccca cccgctggta aattgcgagt ggggcgcgcg tcctagctgg    120
atttaggcca tctgtttttg attaaaattg caagtccgtg tgtcgcgctc ccctaaacgt    180
tggcgcgcca taatggcgat tgataaagca ccgacaaatg tgcgaatttg agcgatggc    240
gtcacggaga agggcaagca aagcatcttc tcatcgctgg tggctatgtt gacgctcttc    300
atctactgtg ctggatgca tgtgctgctg gcgcttgtga tcctgtcctt ctggtaccgc    360
tgggcgctgg tgacggtgct gctgctgtac tccacccctgc tgctgccgcc taagccggtg    420
ctgtggggac cggtctgtcg ctcctggatc ttccagacct ggcgggagta cttcaagttc    480
tcttacgtgt ttgatgaggt gctggactcg aagaagaagt acatcttcgc ggagttcccg    540
cacggtgtct cccccatggg cccactcatt ggcgccacag aatgccagat catgtttccc    600
ggctttgaca tcttcgggct ggcggcgaat gtggtgttca cggtccccct ctggcggcat    660
ttcgtggcgt ggctgggctc cgtgccggcc accacgcgc acttcaagcg ggtgctgaag    720
caaggaagcg tggcggtcat cgtgggaggc atcgcagaga tgtacatgca gagccccacg    780
aaggagcaga tcatgttgaa ggaccgcaag ggctttgttc gtgtggcggt ggaggagggc    840
gtggatggcg catcgtgcc ggtctaccac tttggcaact cgaggtgct ggacttcggc    900
ccccaggcca tggccagtgt gtcccgccgg ctgcgtgcgg ccctgggctt cctgtacgga    960
gtggcctacc tgccctgcc caggcgccg aacatttaca tggtgtgcgg caagcccgtt   1020
cccgtcacgc gcaccgcccg cgacgacccc aagtttgagg aggtggttga cgccactcac   1080
```

```
gccgctgtga tgcggcccct gcaggaggcc tacgaccgcc acaagaccga gtacggctgg   1140
gccgaccgac cgctggtcat cagctgagcg gcggcggtt gaatggctgg gatctgttgc    1200
tggtgctgat ttgtaagtgt ggcttggcgc aatacaggcg gcggcagcag tgcggcggc    1260 agcacccagg gtagcaggag ctgcgcagcc gaaagtgaag cgctgggag agttgtgcgt    1320 gc                                                                 1322
```

<210> SEQ ID NO 5
<211> LENGTH: 346
<212> TYPE: PRT
<213> ORGANISM: Chlamydomonas reinhardtii

<400> SEQUENCE: 5

```
Met Ala Gly Gly Lys Ser Asn Gly Thr Gly Ala Ala Asp Ala His Val
1               5                   10                  15

Arg Thr Ser His Leu Thr Leu Lys Ala Gly Glu Asp Pro Pro Pro Asn
            20                  25                  30

Val Arg Ile Tyr Ser Asp Gly Ile Lys Pro Asp Ala Arg Gln Asn Leu
        35                  40                  45

Leu Val Gln Ile Leu Ala Gly Ile Thr Met Ser Ile Tyr Val Gly Phe
    50                  55                  60

Met Asn Tyr Phe Met Leu Leu Val Leu Ser Tyr Trp Ser Arg Ile
65                  70                  75                  80

Cys Arg Tyr Val Val Leu Ala Leu Leu Gly Thr Leu Ala Leu Pro Cys
                85                  90                  95

Lys Pro Val Leu Trp Pro Ala Phe Asn Lys Leu Trp Ile Phe Lys Thr
            100                 105                 110

Trp Arg His Tyr Phe His Tyr Ser Phe Leu Ile Glu Glu Pro Leu Asp
        115                 120                 125

Pro Asn Lys Arg Tyr Ile Phe Val Glu Phe Pro His Gly Ala Phe Pro
    130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Val Phe Tyr Ile Pro Phe
                165                 170                 175

Trp Arg His Phe Ile Thr Trp Ile Gly Ser Val Pro Ala Thr Pro Gly
            180                 185                 190

Asn Phe Lys Arg Leu Leu Lys Lys Gly Ser Val Ala Val Val Val Gly
        195                 200                 205

Gly Ile Ala Glu Met Tyr Met Gly Asn Lys Lys Glu Arg Ile Lys
    210                 215                 220

Leu Val Gly Arg Arg Gly Phe Ala Arg Ile Ala Leu Glu Glu Gln Val
225                 230                 235                 240

Asp Gly Ile Val Cys Val Tyr Tyr Phe Gly Gln Ser Gln Val Leu Asp
                245                 250                 255

Phe Gly Pro Ser Trp Leu Ala Asp Phe Ser Arg Arg Met Arg Thr Ser
            260                 265                 270

Phe Gly Tyr Leu Thr Gly Trp Met Gly Leu Pro Val Pro Arg Pro Ile
        275                 280                 285

Pro Ile Tyr Met Val Asn Gly Lys Pro Ile Pro Val Pro Lys Val Ala
    290                 295                 300

Arg Asp Ser Pro Glu Phe Asp Lys Glu Val Asp Lys Leu Leu Asp Ala
305                 310                 315                 320

Thr Ile Thr Glu Leu Gly Glu Met Tyr Asn Arg His Arg Gly Glu Tyr
```

325                 330                 335
Gly Trp Gly Asp Arg Pro Leu Ser Ile Glu
            340                 345

<210> SEQ ID NO 6
<211> LENGTH: 1956
<212> TYPE: DNA
<213> ORGANISM: Chlamydomonas reinhardtii

<400> SEQUENCE: 6

| | | |
|---|---|---|
| gcttaccaat actgtttgca atcgtatacg tgcggcgcag cgtgcgggat acgtcccata | 60 |
| aacaccactg cataatccgc gttagccaac gagcttcccc agcgccccg cgcgtgcact | 120 |
| ggcggctttc ggcactagcc aagcctttag gcgtagactg ggcgcctgag gcgcggacac | 180 |
| acagccgcac cgagacgttg agcgtttcat ccgagctcac tcacgcgcat cgccggcggg | 240 |
| acactgcgca cggagcccgc gcgcgtggac acctgggccc ctgcacgaag ggcccctgcg | 300 |
| agacggaagc agatggcagg tggaaagtca acggcacgg gcgcggcgga cgcgcacgtg | 360 |
| cgtacctcgc acttgaccct gaaagctggg gaggacccgc ccccgaatgt tcgcatctac | 420 |
| agtgacggca tcaagccgga cgcgcggcag aacctgcttg ttcagatcct ggccggcatc | 480 |
| acgatgtcga tttatgtagg cttcatgaac tatttcatgc tgctggtggt gctctcctac | 540 |
| tggagccgca tctgccgcta tgtggtcctg gcgctgctag gcacactggc gctgccctgc | 600 |
| aagcccgtgc tgtggcctgc cttcaacaag ctgtggatct tcaagacctg gcgtcactac | 660 |
| ttccactaca gtttcctgat tgaggagccg cttgaccccca caagcgcta catctttgtc | 720 |
| gagttcccgc acggcgcgtt ccccattggt cccatcgtgg cgggcacgct catgcagact | 780 |
| ctgttcccgc acatgatgat ctacagcgtg ccgcctccg tcgtgttcta catccccttc | 840 |
| tggcgccatt tcatcacgtg gatcggctcg gtgcccgcaa cgcccggcaa cttcaagcgg | 900 |
| ctgctgaaga agggcagtgt ggcggtggtg gtgggcggca ttgccgagat gtacatgggc | 960 |
| aacaagaaga aggagcgcat taagctagtg ggccgccgcg gcttcgcacg catcgcgctg | 1020 |
| gaggagcagg tggacggcat tgtgtgcgtg tactacttcg gtcagagcca agtgctggac | 1080 |
| ttcgggccct cctggctggc ggactttagc cgccgcatgc gcaccagctt cggctacctc | 1140 |
| acgggatgga tggggctgcc ggtgccgcgg cccatcccca tctacatggt gaatgggaag | 1200 |
| cccatcccgg tgcccaaggt ggctcgtgac tcgcccgagt tcgacaagga ggtggataag | 1260 |
| ctgcttgacg ccaccatcac ggagctgggc gagatgtaca acaggcacag aggcgagtac | 1320 |
| ggctggggcg accgcccgct gtccatcgag tagatgccca acaagtggat tggcacagtg | 1380 |
| gtgcccttga atggcatgg ccagagtgaa agcgggatgg atcgttggag atggttatgg | 1440 |
| agggaggaa ggaatatctt gaaaaggcca cgcggatggg ttcgtgaggc atgcagggcc | 1500 |
| tttcggggttg gatggggggtc gcactagtcg cacgtgccgc gtgggcacgt gtgtgccgta | 1560 |
| aaccttttat ggtatggtgt gtcaagacta gtctagacgt accgatggct atatggtagc | 1620 |
| tcagctatgc gaaaagctgc gaaacgggct ggcattgcct ttgggtgaac gtgcaagtgt | 1680 |
| tgtgtttaga tgcaaggcag gtggatgcag ttgtaggtgt agcagacctt tacatcagca | 1740 |
| cagttggcta gataggtcgc gtcagccaag gagggagctc tgcgtttgat tgggttgatg | 1800 |
| ctgccagcag gcggcattaa aatggacgtg gcaagggagc aatagagcct ttgaaagaat | 1860 |
| gccatatcct gaagacacac gtgcatgacg caagggtccc gttgctgagc tcctgacttg | 1920 |
| atcatcccctt ggatgctgtc acgcaatgtg cttcaa | 1956 |

<210> SEQ ID NO 7
<211> LENGTH: 327
<212> TYPE: PRT
<213> ORGANISM: Chlamydomonas reinhardtii

<400> SEQUENCE: 7

```
Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Val Leu Leu Pro Ser
            20                  25                  30

Ala Leu Ala Leu Phe Tyr Leu Phe Gly Ala Thr Ser Pro Ser Ala Trp
        35                  40                  45

Leu Leu Leu Ala Ala Phe Leu Ala Leu Thr Phe Thr Pro Leu Gln Leu
    50                  55                  60

Thr Thr Gly Ala Leu Ser Glu Arg Phe Val Gln Phe Ser Val Ala Arg
65                  70                  75                  80

Ala Ala Ala Tyr Phe Pro Thr Arg Val Val Thr Asp Pro Glu Ala
                85                  90                  95

Phe Arg Thr Asp Arg Gly Tyr Leu Phe Gly Phe Cys Pro His Ser Ala
            100                 105                 110

Leu Pro Ile Ala Leu Pro Ile Ala Phe Ala Thr Thr Ser Pro Leu Leu
        115                 120                 125

Pro Lys Glu Leu Arg Gly Arg Thr His Gly Leu Ala Ser Ser Val Cys
    130                 135                 140

Phe Ser Ala Pro Ile Val Arg Gln Leu Tyr Trp Trp Leu Gly Val Arg
145                 150                 155                 160

Pro Ala Thr Arg Gln Ser Ile Ser Gly Leu Leu Arg Ala Arg Lys Val
                165                 170                 175

Ala Val Leu Val Pro Gly Gly Val Gln Glu Val Leu Asn Met Glu His
            180                 185                 190

Gly Lys Glu Val Ala Tyr Leu Ser Ser Arg Thr Gly Phe Val Arg Leu
        195                 200                 205

Ala Val Gln His Gly Ala Pro Leu Val Pro Val Trp Ala Phe Gly Gln
    210                 215                 220

Thr Arg Ala Tyr Ser Trp Phe Arg Pro Gly Pro Pro Leu Val Pro Thr
225                 230                 235                 240

Trp Leu Val Glu Arg Ile Ser Arg Ala Ala Gly Ala Val Pro Ile Gly
                245                 250                 255

Met Phe Gly Gln Tyr Gly Thr Pro Met Pro His Arg Glu Pro Leu Thr
            260                 265                 270

Ile Val Val Gly Arg Pro Ile Pro Val Pro Glu Leu Ala Pro Gly Gln
        275                 280                 285

Leu Glu Pro Glu Pro Glu Val Leu Ala Ala Leu Leu Lys Arg Phe Thr
    290                 295                 300

Asp Asp Leu Gln Ala Leu Tyr Asp Lys His Lys Ala Gln Phe Gly Lys
305                 310                 315                 320

Gly Glu Glu Leu Val Ile Met
                325
```

<210> SEQ ID NO 8
<211> LENGTH: 52
<212> TYPE: DNA
<213> ORGANISM: Artificial Sequence
<220> FEATURE:
<223> OTHER INFORMATION: A synthetic oligonucleotide

<400> SEQUENCE: 8
gcgcaagctt agcatgggtc atcatcacca tcaccatgcg attgataaag ca          52

<210> SEQ ID NO 9
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 9
gcgcgcgcat gctcagctga tgaccagcgg                                    30

<210> SEQ ID NO 10
<211> LENGTH: 54
<212> TYPE: DNA
<213> ORGANISM: Artificial Sequence
<220> FEATURE:
<223> OTHER INFORMATION: A synthetic oligonucleotide

<400> SEQUENCE: 10
gcgcgcaagc ttagcatggg tcatcatcac catcaccatg caggtggaaa gtca        54

<210> SEQ ID NO 11
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 11
gcgcgcctcg agctactcga tggacagcgg                                    30

<210> SEQ ID NO 12
<211> LENGTH: 54
<212> TYPE: DNA
<213> ORGANISM: Artificial Sequence
<220> FEATURE:
<223> OTHER INFORMATION: A synthetic oligonucleotide

<400> SEQUENCE: 12
gcgcgcaagc ttagcatggg tcatcatcac catcaccatc cgctcgcaaa gctg        54

<210> SEQ ID NO 13
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 13
gcgcgcgcat gcctacatta tgaccagctc                                    30

<210> SEQ ID NO 14
<211> LENGTH: 55
<212> TYPE: DNA
<213> ORGANISM: Artificial Sequence
<220> FEATURE:
<223> OTHER INFORMATION: A synthetic oligonucleotide

<400> SEQUENCE: 14
gcgcgcaagc ttagcatggg tcatcatcac catcaccatc cgcgggatcc gccgg       55

<210> SEQ ID NO 15
<211> LENGTH: 30

```
<212> TYPE: DNA
<213> ORGANISM: Artificial Sequence
<220> FEATURE:
<223> OTHER INFORMATION: A synthetic oligonucleotide

<400> SEQUENCE: 15
gcgcgcctcg agtcagcaca cctccagcgg                                       30

<210> SEQ ID NO 16
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 16
cctaggatcc atggcgattg ataaagc                                          27

<210> SEQ ID NO 17
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 17
cccggaattc tagctgatga ccag                                             24

<210> SEQ ID NO 18
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 18
tgtgacaatg gtaccggtat gg                                               22

<210> SEQ ID NO 19
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 19
gccctgggag catcatctc                                                   19

<210> SEQ ID NO 20
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 20
ttgataaagc accgacaaat gtg                                              23

<210> SEQ ID NO 21
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 21
```
gatgctttgc ttgcccttct                                              20

<210> SEQ ID NO 22
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 22
accgatcggc ctttgttg                                                18

<210> SEQ ID NO 23
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 23
tggagaatct gggagcattg a                                            21

<210> SEQ ID NO 24
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 24
ggttcatttt gcctcacact tct                                          23

<210> SEQ ID NO 25
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 25
cccatgatat gaccctcatt ttg                                          23

<210> SEQ ID NO 26
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 26
gcagcttaaa cgtctcaaag aaga                                         24

<210> SEQ ID NO 27
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 27
cccaccaaac atcgaccata a                                            21

<210> SEQ ID NO 28
<211> LENGTH: 24
<212> TYPE: DNA
<213> ORGANISM: Artificial Sequence

```
<220> FEATURE:
<223> OTHER INFORMATION: A synthetic oligonucleotide

<400> SEQUENCE: 28
tcttccgacc taacaaggag tttc                                              24

<210> SEQ ID NO 29
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 29
ccaacgcctt tctcagcttc t                                                 21

<210> SEQ ID NO 30
<211> LENGTH: 320
<212> TYPE: PRT
<213> ORGANISM: Chlamydomonas reinhardtii

<400> SEQUENCE: 30
```

Met Gln Ser Lys Arg Cys Ala Glu Leu Ala Ser Gly Ala Leu Trp Pro
1               5                   10                  15

Met Asp Arg Asp Gln Met Arg Asp Arg Asp Pro Trp Lys Leu Arg Asp
            20                  25                  30

Arg Ala Ile Ser Gln Ala Trp Val Trp Pro Leu Leu Ile Gly Thr Leu
        35                  40                  45

Leu Tyr Val Gln Ser Thr Thr Leu Thr Ile Ala Phe Leu Leu Trp His
    50                  55                  60

Ile Trp Lys Val Met Ala Ser Tyr Phe Pro Gly Ala Arg Leu Ile Lys
65                  70                  75                  80

Thr Ala Asp Leu Asp Pro Ala Gly Arg Tyr Ile Phe Val Ser His Pro
                85                  90                  95

His Gly Val Ile Ala Ile Ser Asp Trp Leu Ala Phe Ala Thr Glu Ala
            100                 105                 110

Leu Gly Phe Ser Lys Leu Phe Pro Gly Leu Asp Leu Arg Cys Ala Thr
        115                 120                 125

Leu Ala Ser Asn Phe Trp Val Pro Gly Leu Arg Glu Tyr Ile Leu Ser
    130                 135                 140

His Gly Met Cys Gly Val Gly Arg Asp Thr Leu Ala Arg Val Leu Thr
145                 150                 155                 160

Gly Lys Pro Gly Arg Ala Val Val Leu Val Gly Gly Ala Ser Glu
                165                 170                 175

Ala Leu Leu Ala Ala Glu Gly Thr Tyr Asp Leu Val Leu Arg Asn Arg
            180                 185                 190

Lys Gly Phe Val Arg Leu Ala Leu Gln Thr Gly Ala Ser Leu Val Pro
        195                 200                 205

Val Leu Ser Tyr Gly Glu Thr Asp Thr Phe His Thr Tyr Ile Pro Pro
    210                 215                 220

Pro Cys Ser Arg Ala Ala Ala Val Met Lys Val Leu Lys Gln Val Phe
225                 230                 235                 240

Gly Phe Ser Thr Pro Leu Cys Trp Gly Thr Gly Leu Phe Gly Gly Trp
                245                 250                 255

Gly Met Leu Ala Leu Gln Val Pro Leu Thr Val Val Gly Ala Pro
            260                 265                 270

Ile Gln Val Asp Lys Val Ser Ser Pro Thr Glu Ala Glu Val Ala Ala

```
                275                 280                 285
Leu His Lys Thr Tyr Thr Glu Ala Leu Gln Lys Leu Trp Asp Asp Thr
290                 295                 300

Val Asp Lys Tyr Gly Lys Gly Val Lys Arg Pro Leu Ala Ile Val Gln
305                 310                 315                 320
```

<210> SEQ ID NO 31
<211> LENGTH: 324
<212> TYPE: PRT
<213> ORGANISM: Chlamydomonas reinhardtii

<400> SEQUENCE: 31

```
Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
                20                  25                  30

Leu Thr Leu Phe Ile Tyr Cys Gly Trp Met His Val Leu Leu Ala Leu
                35                  40                  45

Val Ile Leu Ser Phe Trp Tyr Arg Trp Ala Leu Val Thr Val Leu Leu
        50                  55                  60

Leu Tyr Ser Thr Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Tyr Ile Phe
                100                 105                 110

Ala Glu Phe Pro His Gly Val Phe Pro Met Gly Pro Leu Ile Gly Ala
                115                 120                 125

Thr Glu Cys Gln Ile Met Phe Pro Gly Phe Asp Ile Phe Gly Leu Ala
                130                 135                 140

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys
                165                 170                 175

Gln Gly Ser Val Ala Val Ile Val Gly Gly Ile Ala Glu Met Tyr Met
                180                 185                 190

Gln Ser Pro Thr Lys Glu Gln Ile Met Leu Lys Asp Arg Lys Gly Phe
                195                 200                 205

Val Arg Val Ala Val Glu Glu Gly Val Asp Gly Ile Pro Val
                210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
                245                 250                 255

Val Ala Tyr Leu Pro Leu Pro Arg Arg Arg Asn Ile Tyr Met Val Cys
                260                 265                 270

Gly Lys Pro Val Pro Val Thr Arg Thr Ala Arg Asp Asp Pro Lys Phe
                275                 280                 285

Glu Glu Val Val Asp Ala Thr His Ala Ala Val Met Ala Ala Leu Gln
                290                 295                 300

Glu Ala Tyr Asp Arg His Lys Thr Glu Tyr Gly Trp Ala Asp Arg Pro
305                 310                 315                 320

Leu Val Ile Ser
```

```
<210> SEQ ID NO 32
<211> LENGTH: 346
<212> TYPE: PRT
<213> ORGANISM: Chlamydomonas reinhardtii

<400> SEQUENCE: 32

Met Ala Gly Gly Lys Ser Asn Gly Thr Gly Ala Ala Asp Ala His Val
1               5                   10                  15

Arg Thr Ser His Leu Thr Leu Lys Ala Gly Glu Asp Pro Pro Pro Asn
            20                  25                  30

Val Arg Ile Tyr Ser Asp Gly Ile Lys Pro Asp Ala Arg Gln Asn Leu
        35                  40                  45

Leu Val Gln Ile Leu Ala Gly Ile Thr Met Ser Ile Tyr Val Gly Phe
    50                  55                  60

Met Asn Tyr Phe Met Leu Leu Val Val Leu Ser Tyr Trp Ser Arg Ile
65                  70                  75                  80

Cys Arg Tyr Val Val Leu Ala Leu Leu Gly Thr Leu Ala Leu Pro Cys
                85                  90                  95

Lys Pro Val Leu Trp Pro Ala Phe Asn Lys Leu Trp Ile Phe Lys Thr
            100                 105                 110

Trp Arg His Tyr Phe His Tyr Ser Phe Leu Ile Glu Glu Pro Leu Asp
        115                 120                 125

Pro Asn Lys Arg Tyr Ile Phe Val Glu Phe Pro His Gly Ala Phe Pro
    130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Phe Tyr Ile Pro Phe
                165                 170                 175

Trp Arg His Phe Ile Thr Trp Ile Gly Ser Val Pro Ala Thr Pro Gly
        180                 185                 190

Asn Phe Lys Arg Leu Leu Lys Lys Gly Ser Val Ala Val Val Val Gly
    195                 200                 205

Gly Ile Ala Glu Met Tyr Met Gly Asn Lys Lys Lys Glu Arg Ile Lys
210                 215                 220

Leu Val Gly Arg Arg Gly Phe Ala Arg Ile Ala Leu Glu Glu Gln Val
225                 230                 235                 240

Asp Gly Ile Val Cys Val Tyr Tyr Phe Gly Gln Ser Gln Val Leu Asp
                245                 250                 255

Phe Gly Pro Ser Trp Leu Ala Asp Phe Ser Arg Arg Met Arg Thr Ser
            260                 265                 270

Phe Gly Tyr Leu Thr Gly Trp Met Gly Leu Pro Val Pro Arg Pro Ile
        275                 280                 285

Pro Ile Tyr Met Val Asn Gly Lys Pro Ile Pro Val Pro Lys Val Ala
    290                 295                 300

Arg Asp Ser Pro Glu Phe Asp Lys Glu Val Asp Lys Leu Leu Asp Ala
305                 310                 315                 320

Thr Ile Thr Glu Leu Gly Glu Met Tyr Asn Arg His Arg Gly Glu Tyr
                325                 330                 335

Gly Trp Gly Asp Arg Pro Leu Ser Ile Glu
            340                 345

<210> SEQ ID NO 33
<211> LENGTH: 327
<212> TYPE: PRT
<213> ORGANISM: Chlamydomonas reinhardtii
```

<400> SEQUENCE: 33

Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Val Leu Leu Pro Ser
            20                  25                  30

Ala Leu Ala Leu Phe Tyr Leu Phe Gly Ala Thr Ser Pro Ser Ala Trp
        35                  40                  45

Leu Leu Leu Ala Ala Phe Leu Ala Leu Thr Phe Thr Pro Leu Gln Leu
    50                  55                  60

Thr Thr Gly Ala Leu Ser Glu Arg Phe Val Gln Phe Ser Val Ala Arg
65              70                  75                  80

Ala Ala Ala Tyr Phe Pro Thr Arg Val Val Val Thr Asp Pro Glu Ala
                85                  90                  95

Phe Arg Thr Asp Arg Gly Tyr Leu Phe Gly Phe Cys Pro His Ser Ala
            100                 105                 110

Leu Pro Ile Ala Leu Pro Ile Ala Phe Ala Thr Thr Ser Pro Leu Leu
        115                 120                 125

Pro Lys Glu Leu Arg Gly Arg Thr His Gly Leu Ala Ser Ser Val Cys
    130                 135                 140

Phe Ser Ala Pro Ile Val Arg Gln Leu Tyr Trp Trp Leu Gly Val Arg
145                 150                 155                 160

Pro Ala Thr Arg Gln Ser Ile Ser Gly Leu Arg Ala Arg Lys Val
            165                 170                 175

Ala Val Leu Val Pro Gly Gly Val Gln Glu Val Leu Asn Met Glu His
            180                 185                 190

Gly Lys Glu Val Ala Tyr Leu Ser Ser Arg Thr Gly Phe Val Arg Leu
        195                 200                 205

Ala Val Gln His Gly Ala Pro Leu Val Pro Val Trp Ala Phe Gly Gln
    210                 215                 220

Thr Arg Ala Tyr Ser Trp Phe Arg Pro Gly Pro Pro Leu Val Pro Thr
225                 230                 235                 240

Trp Leu Val Glu Arg Ile Ser Arg Ala Ala Gly Ala Val Pro Ile Gly
            245                 250                 255

Met Phe Gly Gln Tyr Gly Thr Pro Met Pro His Arg Glu Pro Leu Thr
            260                 265                 270

Ile Val Val Gly Arg Pro Ile Pro Val Pro Glu Leu Ala Pro Gly Gln
        275                 280                 285

Leu Glu Pro Glu Pro Glu Val Leu Ala Ala Leu Leu Lys Arg Phe Thr
    290                 295                 300

Asp Asp Leu Gln Ala Leu Tyr Asp Lys His Lys Ala Gln Phe Gly Lys
305                 310                 315                 320

Gly Glu Glu Leu Val Ile Met
                325

<210> SEQ ID NO 34
<211> LENGTH: 413
<212> TYPE: PRT
<213> ORGANISM: Chlamydomonas reinhardtii

<400> SEQUENCE: 34

Met Thr Pro Arg Asp Pro Pro Val Pro Arg Pro Pro Gly Val Arg
1               5                   10                  15

Gln Tyr Thr Asp Gly Arg Ser Ala Ser Tyr Val Leu Pro Leu Pro Tyr
            20                  25                  30

```
Arg Leu Leu Ala Gln Leu Thr Leu Gly Leu Tyr Val Gly Phe Pro Tyr
             35                  40                  45

Ile Leu Leu Gly Leu Leu Leu Gly Thr Ala Ala Gly Ser Arg Ala Ala
 50                  55                  60

Ala Ala Ala Leu Ala Leu Thr Leu Gly Ser Leu Leu Val Pro Ala Pro
 65                  70                  75                  80

Pro His Ile Arg Gln Gly Met Leu Asp Ser Ala Leu Phe Arg Leu Trp
                 85                  90                  95

Arg Ala Tyr Phe Asn Tyr Ser Tyr Ala Tyr Asp Gln Leu Pro Asp Phe
                100                 105                 110

Asn Arg Pro His Ile Phe Val Asn Ser Pro His Gly Ala Phe Pro Leu
            115                 120                 125

Ser Gln Ile Leu Cys Ile Ser Leu Ser Asn Ile Val Trp Pro Gly Phe
130                 135                 140

Pro Val His Ser Leu Ala Ala Ser Val Leu Trp Tyr Ile Pro Leu Trp
145                 150                 155                 160

Arg His Met Lys Ala Ala Leu Gly Ala Ala Pro Ala Ser Arg Asp Asn
                165                 170                 175

Ala Arg Met Leu Leu Arg His Arg Gly Ser Val Ala Val Leu Ala Gly
            180                 185                 190

Gly Ile Ala Glu Met Tyr Thr Ser Ser Pro Ser Arg Ala Ala Ala Ala
        195                 200                 205

Thr Glu Pro Asp Glu Ala Ala Ala Gly Gly Ala Ile Asp Thr Thr
        210                 215                 220

Glu Ala Ala Gly Ala Thr Gly Ser Ser Ser Thr Thr Thr Ser Pro Pro
225                 230                 235                 240

Gln Pro Lys Glu Gln Gln Arg Asp Gly Glu Gln Arg Gln Gly Pro Arg
                245                 250                 255

Lys Gly Leu Lys Gly Leu Leu Lys Gly Pro Lys Asp Asp Pro Asp Pro
            260                 265                 270

Ala Ala Glu Glu Glu Gln Gly Leu Gly Leu Ala Pro Glu Arg Ile Lys
        275                 280                 285

Leu Leu Gly Arg Arg Gly Phe Val Arg Leu Ala Val Glu Met Gly Val
290                 295                 300

Pro Ile Val Pro Ile Tyr His Met Gly Asn Ser Lys Ile Leu Thr Phe
305                 310                 315                 320

Gly Pro Gln Ser Leu Gln Leu Ser Arg Leu Arg Met Ala Leu
                325                 330                 335

Gly Ala Val Phe Gly Val Trp Gly Leu Pro Val Pro Arg Pro Gln Pro
            340                 345                 350

Leu Met Met Cys Val Gly Ser Pro Ile Pro Val Pro Tyr Val Asp Pro
        355                 360                 365

Ala Ala Glu Pro Glu Arg Phe Glu Ala Val Val Ala Ala Val His Gly
            370                 375                 380

Gln Val Val Ala Ala Phe Gln Asp Leu Tyr Asn Arg Tyr Arg Val Gln
385                 390                 395                 400

Tyr Gly Cys Gly Trp Glu Arg Arg Pro Leu Glu Val Cys
                405                 410

<210> SEQ ID NO 35
<211> LENGTH: 314
<212> TYPE: PRT
<213> ORGANISM: Arabidopsis thaliana

<400> SEQUENCE: 35
```

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65              70                  75                  80

Ala Cys Asn Tyr Phe Pro Val Ser Leu Tyr Val Glu Asp Tyr Glu Ala
                85                  90                  95

Phe Gln Pro Asn Arg Ala Tyr Val Phe Gly Tyr Glu Pro His Ser Val
            100                 105                 110

Leu Pro Ile Gly Val Val Ala Leu Cys Asp Leu Thr Gly Phe Met Pro
        115                 120                 125

Ile Pro Asn Ile Lys Val Leu Ala Ser Ser Ala Ile Phe Tyr Thr Pro
    130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Arg Gly Phe Val Arg Ile Ala Met Glu Gln
        195                 200                 205

Gly Ser Pro Leu Val Pro Val Phe Cys Phe Gly Gln Ala Arg Val Tyr
    210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Val Gly Lys Pro Ile Glu Val
            260                 265                 270

Thr Lys Thr Leu Lys Pro Thr Asp Glu Glu Ile Ala Lys Phe His Gly
    275                 280                 285

Gln Tyr Val Glu Ala Leu Arg Asp Leu Phe Glu Arg His Lys Ser Arg
    290                 295                 300

Val Gly Tyr Asp Leu Glu Leu Lys Ile Leu
305                 310

<210> SEQ ID NO 36
<211> LENGTH: 322
<212> TYPE: PRT
<213> ORGANISM: Vernicia fordii

<400> SEQUENCE: 36

Met Gly Met Val Glu Val Lys Asn Glu Glu Glu Val Thr Ile Phe Lys
1               5                   10                  15

Ser Gly Glu Ile Tyr Pro Thr Asn Ile Phe Gln Ser Val Leu Ala Leu
            20                  25                  30

Ala Ile Trp Leu Gly Ser Phe His Phe Ile Leu Phe Leu Val Ser Ser
        35                  40                  45

Ser Ile Phe Leu Pro Phe Ser Lys Phe Leu Leu Val Ile Gly Leu Leu

```
                 50                  55                  60

Leu Phe Phe Met Val Ile Pro Ile Asn Asp Arg Ser Lys Leu Gly Gln
 65                  70                  75                  80

Cys Leu Phe Ser Tyr Ile Ser Arg His Val Cys Ser Tyr Phe Pro Ile
                 85                  90                  95

Thr Leu His Val Glu Asp Ile Asn Ala Phe Arg Ser Asp Arg Ala Tyr
            100                 105                 110

Val Phe Gly Tyr Glu Pro His Ser Val Phe Pro Ile Gly Val Met Ile
        115                 120                 125

Leu Ser Leu Gly Leu Ile Pro Leu Pro Asn Ile Lys Phe Leu Ala Ser
    130                 135                 140

Ser Ala Val Phe Tyr Thr Pro Phe Leu Arg His Ile Trp Ser Trp Cys
145                 150                 155                 160

Gly Leu Thr Pro Ala Thr Arg Lys Asn Phe Val Ser Leu Leu Ser Ser
                165                 170                 175

Gly Tyr Ser Cys Ile Leu Val Pro Gly Gly Val Gln Glu Thr Phe Tyr
            180                 185                 190

Met Lys Gln Asp Ser Glu Ile Ala Phe Leu Lys Ala Arg Arg Gly Phe
        195                 200                 205

Ile Arg Ile Ala Met Gln Thr Gly Thr Pro Leu Val Pro Val Phe Cys
    210                 215                 220

Phe Gly Gln Met His Thr Phe Lys Trp Trp Lys Pro Asp Gly Glu Leu
225                 230                 235                 240

Phe Met Lys Ile Ala Arg Ala Ile Lys Phe Thr Pro Thr Ile Phe Trp
                245                 250                 255

Gly Val Leu Gly Thr Pro Leu Pro Phe Lys Asn Pro Met His Val Val
            260                 265                 270

Val Gly Arg Pro Ile Glu Val Lys Gln Asn Pro Gln Pro Thr Ala Glu
        275                 280                 285

Glu Val Ala Glu Val Gln Arg Glu Phe Ile Ala Ser Leu Lys Asn Leu
    290                 295                 300

Phe Glu Arg His Lys Ala Arg Val Gly Tyr Ser Asp Leu Lys Leu Glu
305                 310                 315                 320

Ile Phe

<210> SEQ ID NO 37
<211> LENGTH: 340
<212> TYPE: PRT
<213> ORGANISM: Ricinus communis

<400> SEQUENCE: 37

Met Gly Glu Glu Ala Asn His Asn Asn Asn Asn Asn Ile Asn Ser
 1               5                  10                  15

Asn Asp Glu Lys Asn Glu Glu Lys Ser Asn Tyr Thr Val Val Asn Ser
                 20                  25                  30

Arg Glu Leu Tyr Pro Thr Asn Ile Phe His Ala Leu Leu Ala Leu Ser
             35                  40                  45

Ile Trp Ile Gly Ser Ile His Phe Asn Leu Phe Leu Leu Phe Ile Ser
     50                  55                  60

Tyr Leu Phe Leu Ser Phe Pro Thr Phe Leu Leu Ile Val Gly Phe Phe
 65                  70                  75                  80

Val Val Leu Met Phe Ile Pro Ile Asp Glu His Ser Lys Leu Gly Arg
                 85                  90                  95

Arg Leu Cys Arg Tyr Val Cys Arg His Ala Cys Ser His Phe Pro Val
```

```
            100                 105                 110
Thr Leu His Val Glu Asp Met Asn Ala Phe His Ser Asp Arg Ala Tyr
        115                 120                 125

Val Phe Gly Tyr Glu Pro His Ser Val Phe Pro Leu Gly Val Ser Val
130                 135                 140

Leu Ser Asp His Phe Ala Val Leu Pro Leu Pro Lys Met Lys Val Leu
145                 150                 155                 160

Ala Ser Asn Ala Val Phe Arg Thr Pro Val Leu Arg His Ile Trp Thr
                165                 170                 175

Trp Cys Gly Leu Thr Ser Ala Thr Lys Lys Asn Phe Thr Ala Leu Leu
            180                 185                 190

Ala Ser Gly Tyr Ser Cys Ile Val Ile Pro Gly Gly Val Gln Glu Thr
        195                 200                 205

Phe Tyr Met Lys His Gly Ser Glu Ile Ala Phe Leu Lys Ala Arg Arg
    210                 215                 220

Gly Phe Val Arg Val Ala Met Glu Met Val Lys Pro Leu Val Pro Val
225                 230                 235                 240

Phe Cys Phe Gly Gln Ser Asn Val Tyr Lys Trp Trp Lys Pro Asp Gly
                245                 250                 255

Glu Leu Phe Met Lys Ile Ala Arg Ala Ile Lys Phe Ser Pro Ile Val
            260                 265                 270

Phe Trp Gly Val Leu Gly Ser His Leu Pro Leu Gln Arg Pro Met His
        275                 280                 285

Val Val Val Gly Lys Pro Ile Glu Val Lys Gln Asn Pro Gln Pro Thr
290                 295                 300

Val Glu Glu Val Ser Glu Val Gln Gly Gln Phe Val Ala Ala Leu Lys
305                 310                 315                 320

Asp Leu Phe Glu Arg His Lys Ala Arg Val Gly Tyr Ala Asp Leu Thr
                325                 330                 335

Leu Glu Ile Leu
            340

<210> SEQ ID NO 38
<211> LENGTH: 418
<212> TYPE: PRT
<213> ORGANISM: Saccharomyces cerevisiae

<400> SEQUENCE: 38

Met Ser Gly Thr Phe Asn Asp Ile Arg Arg Lys Glu Glu Gly
1               5                   10                  15

Ser Pro Thr Ala Gly Ile Thr Glu Arg His Glu Asn Lys Ser Leu Ser
                20                  25                  30

Ser Ile Asp Lys Arg Glu Gln Thr Leu Lys Pro Gln Leu Glu Ser Cys
            35                  40                  45

Cys Pro Leu Ala Thr Pro Phe Glu Arg Arg Leu Gln Thr Leu Ala Val
        50                  55                  60

Ala Trp His Thr Ser Ser Phe Val Leu Phe Ser Ile Phe Thr Leu Phe
65                  70                  75                  80

Ala Ile Ser Thr Pro Ala Leu Trp Val Leu Ala Ile Pro Tyr Met Ile
                85                  90                  95

Tyr Phe Phe Phe Asp Arg Ser Pro Ala Thr Gly Glu Val Val Asn Arg
                100                 105                 110

Tyr Ser Leu Arg Phe Arg Ser Leu Pro Ile Trp Lys Trp Tyr Cys Asp
            115                 120                 125
```

```
Tyr Phe Pro Ile Ser Leu Ile Lys Thr Val Asn Leu Lys Pro Thr Phe
    130                 135                 140

Thr Leu Ser Lys Asn Lys Arg Val Asn Glu Lys Asn Tyr Lys Ile Arg
145                 150                 155                 160

Leu Trp Pro Thr Lys Tyr Ser Ile Asn Leu Lys Ser Asn Ser Thr Ile
                165                 170                 175

Asp Tyr Arg Asn Gln Glu Cys Thr Gly Pro Thr Tyr Leu Phe Gly Tyr
                180                 185                 190

His Pro His Gly Ile Gly Ala Leu Gly Ala Phe Gly Ala Phe Ala Thr
            195                 200                 205

Glu Gly Cys Asn Tyr Ser Lys Ile Phe Pro Gly Ile Pro Ile Ser Leu
        210                 215                 220

Met Thr Leu Val Thr Gln Phe His Ile Pro Leu Tyr Arg Asp Tyr Leu
225                 230                 235                 240

Leu Ala Leu Gly Ile Ser Ser Val Ser Arg Lys Asn Ala Leu Arg Thr
                245                 250                 255

Leu Ser Lys Asn Gln Ser Ile Cys Ile Val Gly Gly Ala Arg Glu
                260                 265                 270

Ser Leu Leu Ser Ser Thr Asn Gly Thr Gln Leu Ile Leu Asn Lys Arg
        275                 280                 285

Lys Gly Phe Ile Lys Leu Ala Ile Gln Thr Gly Asn Ile Asn Leu Val
        290                 295                 300

Pro Val Phe Ala Phe Gly Glu Val Asp Cys Tyr Asn Val Leu Ser Thr
305                 310                 315                 320

Lys Lys Asp Ser Val Leu Gly Lys Met Gln Leu Trp Phe Lys Glu Asn
                325                 330                 335

Phe Gly Phe Thr Ile Pro Ile Phe Tyr Ala Arg Gly Leu Phe Asn Tyr
                340                 345                 350

Asp Phe Gly Leu Leu Pro Phe Arg Ala Pro Ile Asn Val Val Val Gly
            355                 360                 365

Arg Pro Ile Tyr Val Glu Lys Lys Ile Thr Asn Pro Pro Asp Asp Val
            370                 375                 380

Val Asn His Phe His Asp Leu Tyr Ile Ala Glu Leu Lys Arg Leu Tyr
385                 390                 395                 400

Tyr Glu Asn Arg Glu Lys Tyr Gly Val Pro Asp Ala Glu Leu Lys Ile
                405                 410                 415

Val Gly

<210> SEQ ID NO 39
<211> LENGTH: 325
<212> TYPE: PRT
<213> ORGANISM: Ostreococcus tauri

<400> SEQUENCE: 39

Met Ser Arg Ser Ile Val Asp His Gly Val Leu Leu Val Trp Leu Gly
1               5                   10                  15

Leu Phe His Ala Leu Val Val Val Val Ala Ile Val Ala Leu
                20                  25                  30

Glu Arg Arg Arg Ala Met Thr Val Leu Ala Ala Leu Met Ser Leu Ser
            35                  40                  45

Val Val Pro Arg Arg Ile Arg Pro Arg Trp Gly Val Thr Leu Ala Arg
        50                  55                  60

Ala Ile Thr Arg Thr Ala Lys Ser Tyr Phe Pro Cys Ala Leu Thr Phe
65              70                  75                  80
```

-continued

```
Glu Asn Glu Glu Ala Tyr Leu Lys Gly Ala Arg Lys Gly Val Gly Arg
                85                  90                  95

Leu Val Gly Leu Glu Pro His Gly Ala Leu Pro Leu Ser Val Ile Ala
            100                 105                 110

Phe Ala Asp Tyr Phe Met Phe Asp Glu Asp Gly Ile Glu Ala Arg Gly
            115                 120                 125

Met Asn His Ala Ala Ser Met Asn Ser Arg Ala Leu Ala Ser Gly Ala
    130                 135                 140

Ile Phe His Val Pro Leu Val Arg His Leu Trp Thr Trp Leu Gly Leu
145                 150                 155                 160

Glu Pro Ile Ser Arg Arg Arg Met Thr Ser Met Leu Ser Asp Gly Ser
                165                 170                 175

Thr Cys Val Ile Val Pro Gly Gly Val Ala Glu Cys Met Ala Met Glu
            180                 185                 190

Arg Gly Val Glu Thr Leu Tyr Leu Lys Arg Arg Tyr Gly Phe Val Lys
            195                 200                 205

Ile Ala Ile Gln Thr Gly Ala Ala Leu Val Pro Ala Tyr Thr Phe Gly
    210                 215                 220

Gln Thr Arg Ala Tyr Lys Tyr Trp Arg Leu Gly Pro Pro Leu Val Pro
225                 230                 235                 240

Thr Ser Val Ala Asn Trp Phe Ser Lys Thr Phe Ser Phe Ala Pro Met
                245                 250                 255

Val Phe Trp Gly Lys Trp Phe Thr Pro Ile Pro Tyr Ala Thr Pro Leu
            260                 265                 270

His Thr Val Val Gly Glu Leu Ile Glu Thr Thr Gln Asn Asp Asn Pro
        275                 280                 285

Ser Arg Glu Glu Val Gln Ala Lys Leu Asp Glu Phe Ile Val Ala Met
    290                 295                 300

Arg Ser Leu Tyr Asp Arg His Lys Ser Ala His Gly Tyr Ala Asp Val
305                 310                 315                 320

Asp Leu Val Val Cys
                325
```